United States Patent
Hogan et al.

(10) Patent No.: US 11,542,498 B2
(45) Date of Patent: *Jan. 3, 2023

(54) MICROARRAY BASED MULTIPLEX PATHOGEN ANALYSIS AND USES THEREOF

(71) Applicants: Michael Edward Hogan, Stony Brook, NY (US); Melissa Rose May, Tucson, AZ (US); Frederick Henry Eggers, Sahuarita, AZ (US)

(72) Inventors: Michael Edward Hogan, Stony Brook, NY (US); Melissa Rose May, Tucson, AZ (US); Frederick Henry Eggers, Sahuarita, AZ (US)

(73) Assignee: PathogenDx, Inc., Scottsdale, AZ (US)

( * ) Notice: Subject to any disclaimer, the term of this patent is extended or adjusted under 35 U.S.C. 154(b) by 280 days.

This patent is subject to a terminal disclaimer.

(21) Appl. No.: 15/916,062

(22) Filed: Mar. 8, 2018

(65) Prior Publication Data

US 2018/0251758 A1  Sep. 6, 2018

Related U.S. Application Data

(63) Continuation-in-part of application No. 15/388,561, filed on Dec. 22, 2016, now abandoned.

(60) Provisional application No. 62/271,371, filed on Dec. 28, 2015.

(51) Int. Cl.
| | | |
|---|---|---|
| *C40B 60/04* | (2006.01) | |
| *C12N 15/10* | (2006.01) | |
| *C12Q 1/6837* | (2018.01) | |
| *G01N 33/53* | (2006.01) | |

(52) U.S. Cl.
CPC ....... *C12N 15/1086* (2013.01); *C12Q 1/6837* (2013.01); *G01N 33/5308* (2013.01)

(58) Field of Classification Search
CPC .................................................. C12N 15/10
See application file for complete search history.

(56) References Cited

U.S. PATENT DOCUMENTS

| | | | | |
|---|---|---|---|---|
| 2004/0110129 A1* | 6/2004 | Fischer | ........... | C12Q 1/689 435/6.11 |
| 2009/0011949 A1* | 1/2009 | Hogan | ........... | B01J 19/0046 506/9 |
| 2010/0184022 A1* | 7/2010 | Colau | ........... | C12Q 1/6834 435/5 |
| 2012/0101230 A1* | 4/2012 | Wang | ........... | G01N 33/54353 525/54.11 |
| 2014/0342947 A1* | 11/2014 | Hogan | ........... | B01J 19/123 506/18 |
| 2017/0327599 A1* | 11/2017 | Hogan | ........... | B01J 19/0046 |

OTHER PUBLICATIONS

Eggers et al., Simplified, Highly Multiplex Pathogen Analysis for Agricultural, Food, Water, and Environmental Sampling, Article 1096262, Inform Magazine, 2017, 1-11. (Year: 2017).*
Press Release, PathogenDx and Emerald Scientific Announce Distribution Agreement for the PDx-C Test Kits, Cannabis Business Executive—Cannabis and Marijuana Industry News, 2017, 1-2. (Year: 2017).*
Schott, Epoxysilane, Schott Minifab, 2021, 1-2. Obtained online at: https://schott-minifab.com/what-we-do/glass-components/functional-coatings/epoxysilane-coating-e on Oct. 13, 2021. (Year: 2021).*
Sobek et al., Drop Drying On Surfaces Determines Chemical Reactivity—The Specific Case of Immobilization of Oligonucleotides on Microarrays, BMC Biophysics, 2013, 6(8), 1-13. (Year: 2013).*

* cited by examiner

*Primary Examiner* — Amy M Bunker
(74) *Attorney, Agent, or Firm* — Benjamin Aaron Adler

(57) ABSTRACT

Provided herein is a 3-dimensional lattice microarray system for DNA sequence detection and analysis. The system has a plurality of bifunctional polymer linkers, on one end of which are attached nucleic acid probes where each have a sequence complementary to signature nucleotide sequences in pathogens, plants or animals. The other end of the bifunctional polymer linker is attached to a solid support by non-covalent or covalent means. Each of the nucleic acid probes have terminal thymidine bases at the 5' and 3' ends that permit attachment of the probes to the bifunctional polymer linkers. Also provided is a method for fabricating the microarray system by first attaching the bifunctional polymer linkers to the solid support, followed by photochemical coupling of the nucleic probes to the microarray. A customizable microarray kit is provided that contains the solid support, linkers, probes, solvent mixture and instructions to use the kit.

3 Claims, 17 Drawing Sheets
Specification includes a Sequence Listing.

ITS1 Locus (Cannabis plant control)

PURIFIED DNA BACTERIA PANEL

| | Aeromonas hydrophila | Bacillus subtilis | Campylobacter ssp. | E.coli | E.coli O157:H7 | Listeria ssp. | Pseudomonas aeruginosa | Salmonella enterica | Xanthamonas ssp. |
|---|---|---|---|---|---|---|---|---|---|
| Low Pan Bacteria Control | 4434 | 15943 | 38700 | 4215 | 1745 | 14140 | 26431 | 11167 | 22152 |
| Medium Pan Bacteria Control | 7893 | 33069 | 28705 | 8349 | 3638 | 35237 | 39002 | 17682 | 24141 |
| High Pan Bacteria Control | 14934 | 23469 | 32936 | 9827 | 4327 | 16726 | 38682 | 28596 | 22072 |
| Low Bile tolerant gram negative | 5364 | 947 | 867 | 2803 | 1801 | 817 | 4852 | 4453 | 461 |
| High Bile tolerant gram negative | 55228 | 339 | 422 | 24172 | 14746 | 1482 | 36337 | 32579 | 356 |
| Total Coliform | 106 | 101 | 145 | 8276 | 9175 | 139 | 145 | 204 | 196 |
| E.coli | 104 | 121 | 127 | 55419 | 47805 | 151 | 144 | 83 | 147 |
| E.coli specific gene | 318 | 255 | 422 | 57638 | 57112 | 521 | 695 | 641 | 461 |
| E.coli Stx1 | 106 | 116 | 158 | 134 | 65535 | 151 | 142 | 196 | 145 |
| E.coli Stx2 | 100 | 100 | 126 | 169 | 52041 | 135 | 147 | 117 | 132 |
| Enterobacteriacea | 885 | 125 | 211 | 58323 | 36641 | 179 | 375 | 23847 | 204 |
| Salmonella/Enterobacter | 115 | 99 | 124 | 190 | 160 | 144 | 138 | 37520 | 144 |
| Salmonella specific gene | 189 | 175 | 217 | 208 | 392 | 212 | 211 | 8124 | 231 |
| Aeromonas | 10335 | 120 | 123 | 127 | 139 | 163 | 142 | 99 | 146 |
| Pseudomonas | 106 | 107 | 120 | 130 | 126 | 133 | 25866 | 77 | 153 |
| Pseudomonas aeruginosa | 169 | 228 | 173 | 318 | 1217 | 208 | 64437 | 135 | 424 |
| Xanthamonas | 98 | 188 | 122 | 133 | 143 | 143 | 221 | 80 | 41903 |
| Listeria | 117 | 263 | 144 | 136 | 128 | 24783 | 144 | 79 | 131 |
| Campylobacter | 148 | 120 | 65535 | 139 | 153 | 224 | 144 | 88 | 160 |
| Bacillus Group 2 | 143 | 3451.7 | 121 | 128 | 150 | 137 | 139 | 81 | 134 |

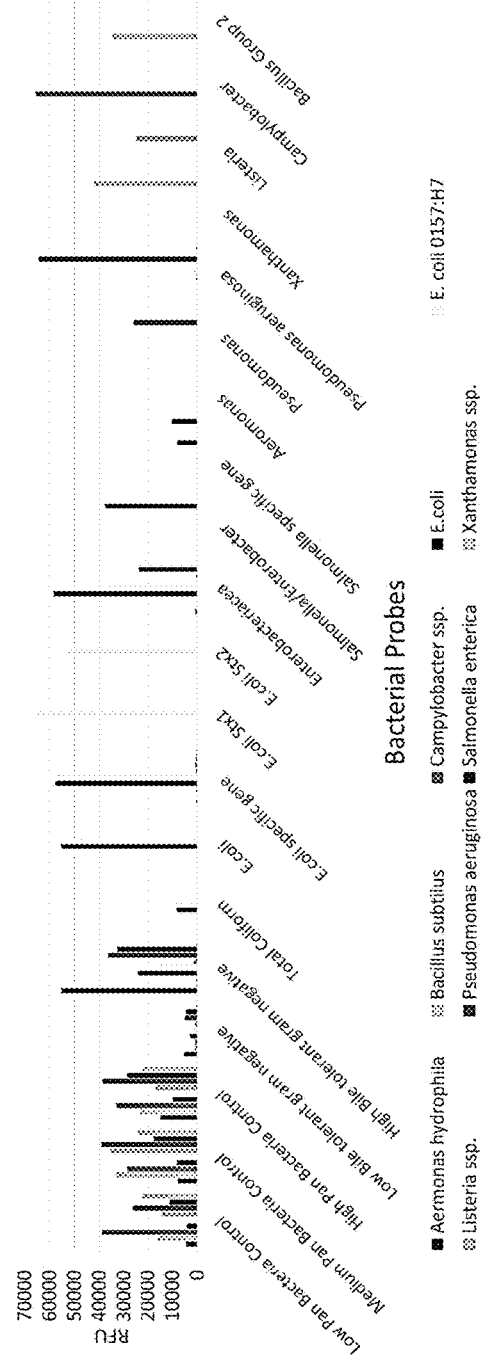

FIG. 11A

| PURIFIED DNA FUNGAL PANEL | | | | | | |
|---|---|---|---|---|---|---|
| | A. fumigatus | A. flavus | A. niger | Fusarium spp. | Penicillium spp. | Mucor spp. |
| Low Pan Fungal Control | 4269 | 6097 | 5252 | 13907 | 3929 | 30733 |
| Medium Pan Fungal Control | 27006 | 30445 | 19746 | 30972 | 30947 | 49986 |
| High Pan Fungal Control | 64940 | 64679 | 54483 | 47268 | 65535 | 63932 |
| Negative Control | 119 | 127 | 151 | 107 | 117 | 118 |
| Aspergillus fumigatus | 62018 | 232 | 114 | 604 | 126 | 228 |
| Aspergillus flavus | 210 | 65535 | 116 | 102 | 115 | 128 |
| Aspergillus niger | 113 | 235 | 24867 | 108 | 115 | 112 |
| Botrytis | 189 | 205 | 435 | 101 | 126 | 121 |
| Penicillium | 171 | 282 | 121 | 100 | 5891 | 316 |
| Fusarium solani | 112 | 131 | 174 | 16578 | 113 | 140 |
| Mucor | 118 | 152 | 113 | 150 | 113 | 29886 |

| Identification Panel | | | | | |
|---|---|---|---|---|---|
| Sample | 1 | 2 | 3 | 4 | 5 |
| Cannabis DNA control | 29348 | 18804 | 17983 | 14549 | 14960 |
| Aeromonas | 137 | 145 | 245 | 138 | 382 |
| E.coli | 132 | 145 | 144 | 124 | 389 |
| E.coli specific gene | 563 | 471 | 461 | 1205 | 6408 |
| Enterobacteriacea | 136 | 14805 | 14246 | 149 | 24701 |
| Listeria | 142 | 163 | 142 | 133 | 311 |
| Pseudomonas | 112 | 1895 | 2033 | 102 | 1579 |
| Pseudomonas aeruginosa | 153 | 1140 | 992 | 121 | 2290 |
| Salmonella/Enterobacter | 125 | 285 | 616 | 126 | 742 |
| Salmonella specific gene | 199 | 201 | 207 | 164 | 320 |
| Xanthamonas | 119 | 151 | 141 | 106 | 213 |
| Aspergillus fumigatus | 33335 | 9241 | 3861 | 3676 | 6224 |
| Aspergillus flavus | 1228 | 112 | 1198 | 136 | 2955 |
| Aspergillus niger | 129 | 119 | 161 | 142 | 691 |
| Botrytis | 159 | 142 | 182 | 120 | 181 |
| Penicillium | 154 | 182 | 153 | 100 | 2504 |
| Fusarium solani | 132 | 115 | 127 | 111 | 135 |
| Mucor | 122 | 139 | 129 | 130 | 129 |
| Candida | 286 | 173 | 415 | 108 | 129 |

|  | Cannabis Wash | Candida albicans Vitriod |
|---|---|---|
| Cannabis DNA control 1 | 1810 | 113 |
| Cannabis DNA control 2 | 9203 | 124 |
| Low Pan Fungal Control | 9526 | 14051 |
| Medium Pan Fungal Con | 21814 | 37310 |
| High Pan Fungal Control | 41190 | 65000 |
| Negative control | 45 | 131 |
| Aspergillus fumigatus | 292 | 152 |
| Aspergillus flavus | 39 | 135 |
| Aspergillus niger | 37 | 130 |
| Botrytis | 29 | 228 |
| Penicillium | 34 | 118 |
| Fusarium solani | 42 | 126 |
| Mucor | 39 | 121 |
| Candida Group 1 | 2695 | 6885 |
| Candida albicans | 37 | 10386 |
| Isaria Biofoliar | 29 | 126 |
| Myrothesium Biofoliar | 135 | 121 |
| Pythium Biofoliar | 153 | 189 |

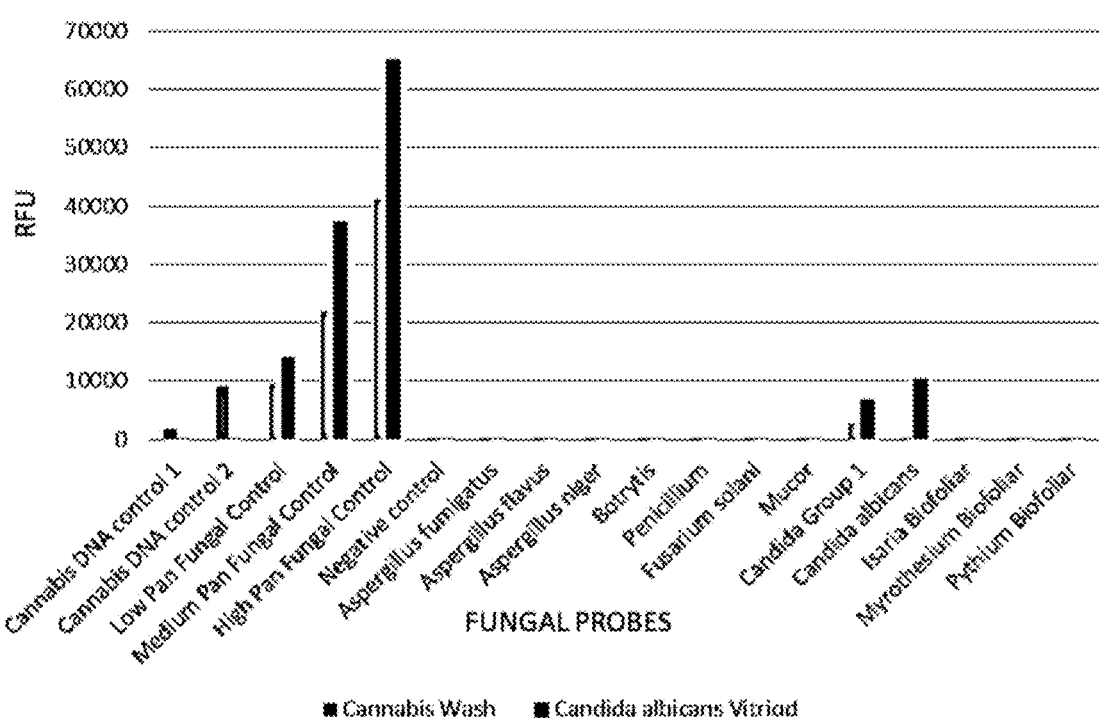

FIG. 13

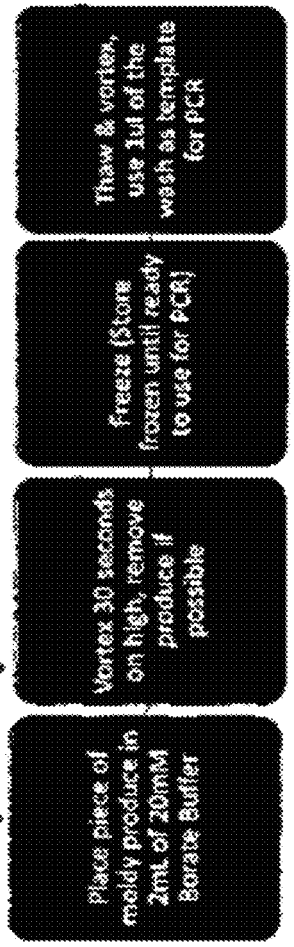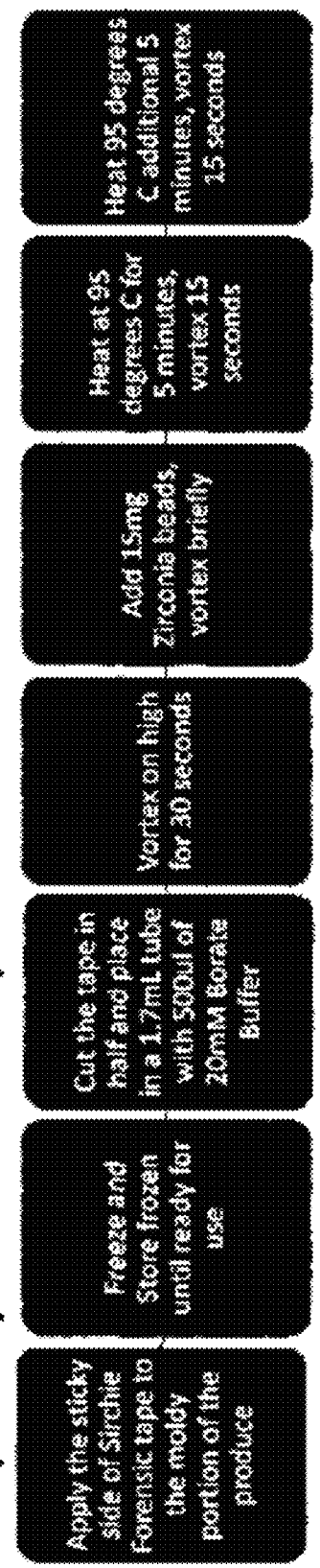
FIG. 16

MICROARRAY BASED MULTIPLEX PATHOGEN ANALYSIS AND USES THEREOF

CROSS-REFERENCE TO RELATED APPLICATIONS

This application is a continuation-In-part under 35 U.S.C. § 120 of non-provisional application U.S. Ser. No. 15/388,561, filed Dec. 22, 2016, which claims benefit of priority under 35 U.S.C. § 119(e) of provisional application U.S. Ser. No. 62/271,371, filed Dec. 28, 2015, both of which are hereby incorporated in their entireties.

BACKGROUND OF THE INVENTION

Field of the Invention

The present disclosure is in the technical field of DNA based pathogen and plant analysis. More particularly, the present disclosure is in the technical field of pathogen analysis for plant, agriculture, food and water material using a multiplex assay and a 3-dimensional lattice microarray technology for immobilizing nucleic acid probes.

Description of the Related Art

Current techniques used to identify microbial pathogens rely upon established clinical microbiology monitoring. Pathogen identification is conducted using standard culture and susceptibility tests. These tests require a substantial investment of time, effort, cost as well as labile products. Current techniques are not ideal for testing large numbers samples. Culture-based testing is fraught with inaccuracies which include both false positives and false negatives, as well as unreliable quantification of colony forming units (CFUs). There are issues with the presence of viable but non-culturable microorganisms which do not show up using conventional culture methods. Certain culture tests are very non-specific in terms of detecting both harmful and harmless species which diminishes the utility of the test to determine if there is a threat present in the sample being tested.

In response to challenges including false positives and culturing of microorganisms, DNA-based diagnostic methods such as polymerase chain reaction (PCR) amplification techniques were developed. To analyze a pathogen using PCR, DNA is extracted from a material prior to analysis, which is a time-consuming and costly step.

In an attempt to eliminate the pre-analysis extraction step of PCR, Colony PCR was developed. Using cells directly from colonies from plates or liquid cultures, Colony PCR allows PCR of bacterial cells without sample preparation. This technique was a partial success but was not as sensitive as culture indicating a possible issue with interference of the PCR by constituents in the specimens. Although this possible interference may not be significant enough to invalidate the utility of the testing performed, such interference can be significant for highly sensitive detection of pathogens for certain types of tests. Consequently, Colony PCR did not eliminate the pre-analysis extraction step for use of PCR, especially for highly sensitive detection of pathogens.

It is known that 16S DNA in bacteria and the ITS2 DNA in yeast or mold can be PCR amplified, and once amplified can be analyzed to provide information about the specific bacteria or specific mold or yeast contamination in or on plant material. Further, for certain samples such as blood, fecal matter and others, PCR may be performed on the DNA in such samples absent any extraction of the DNA. However, for blood it is known that the result of such direct PCR is prone to substantial sample to sample variation due to inhibition by blood analytes. Additionally, attempts to perform direct PCR analysis on plant matter have generally been unsuccessful, due to heavy inhibition of PCR by plant constituents.

Over time, additional methods and techniques were developed to improve on the challenges of timely and specific detection and identification of pathogens. Immuno-assay techniques provide specific analysis. However, the technique is costly in the use of chemical consumables and has a long response time. Optical sensor technologies produce fast real-time detection but such sensor lack identification specificity as they offer a generic detection capability as the pathogen is usually optically similar to its benign background. Quantitative Polymerase Chain Reaction (qPCR) technique is capable of amplification and detection of a DNA sample in less than an hour. However, qPCR is largely limited to the analysis of a single pathogen. Consequently, if many pathogens are to be analyzed concurrently, as is the case with plant, agriculture, food and water material, a relatively large number of individual tests are performed in parallel.

Biological microarrays have become a key mechanism in a wide range of tools used to detect and analyze DNA. Microarray-based detection combines DNA amplification with the broad screening capability of microarray technology. This results in a specific detection and improved rate of process. DNA microarrays can be fabricated with the capacity to interrogate, by hybridization, certain segments of the DNA in bacteria and eukaryotic cells such as yeast and mold. However, processing a large number of PCR reactions for downstream microarray applications is costly and requires highly skilled individuals with complex organizational support. Because of these challenges, microarray techniques have not led to the development of downstream applications.

It is well known that DNA may be linked to a solid support for the purposes of DNA analysis. In those instances, the surface-associated DNA is generally referred to as the "Oligonucleotide probe" (nucleic acid probe, DNA probe) and its cognate partner to which the probe is designed to bind is referred to as the Hybridization Target (DNA Target). In such a device, detection and-or quantitation of the DNA Target is obtained by observing the binding of the Target to the surface bound Probe via duplex formation, a process also called "DNA Hybridization" (Hybridization).

Nucleic acid probe linkage to the solid support may be achieved by non-covalent adsorption of the DNA directly to a surface as occurs when a nucleic acid probe adsorbs to a neutral surface such as cellulose or when a nucleic acid probe adsorbs to cationic surface such as amino-silane coated glass or plastic. Direct, non-covalent adsorption of nucleic acid probes to the support has several limitations. The nucleic acid probe is necessarily placed in direct physical contact with the surface thereby presenting steric constraints to its binding to a DNA Target as the desired (bound) Target-Probe complex is a double helix which can only form by wrapping of the Target DNA strand about the bound Probe DNA: an interaction which is fundamentally inhibited by direct physical adsorption of the nucleic acid probe upon the underlying surface.

Nucleic acid probe linkage may also occur via covalent attachment of the nucleic acid probe to a surface. This can be induced by introduction of a reactive group (such as a primary amine) into the Probe then covalent attachment of the Probe, through the amine, to an amine-reactive moiety placed upon the surface: such as an epoxy group, or an isocyanate group, to form a secondary amine or a urea linkage, respectively. Since DNA is not generally reactive with epoxides or isocyanates or other similar standard nucleophilic substitutions, the DNA Probe must be first chemically modified with "unnatural" ligands such as primary amines or thiols. While such chemistry may be readily implemented during oligonucleotide synthesis, it raises the cost of the DNA Probe by more than a factor of two, due to the cost associated with the modification chemistry. A related UV crosslinking based approach circumvents the need for unnatural base chemistry, wherein Probe DNA can be linked to the surface via direct UV crosslinking of the DNA, mediated by photochemical addition of thymine within the Probe DNA to the amine surface to form a secondary amine adduct. However, the need for high energy UV for efficient crosslinking results in substantial side reactions that can damage the nucleic acid probe beyond use. As is the case for adsorptive linkage, the covalent linkages possible between a modified nucleic acid probe and a reactive surface are very short, in the order of less than 10 rotatable bonds, thereby placing the nucleic acid probe within 2 nm of the underlying surface. Given that a standard nucleic acid probe is >20 bases in length (>10 nm long) a Probe/linker length ratio >10/1 also provides for destabilizing inhibition of the subsequent formation of the desired Target-Probe Duplex.

Previous Attempts at addressing these problems have not met with success. Attachment of nucleic acid probes to surfaces via their entrapment into a 3-Dimensional gel phase such as that created by polymerizing acrylamide and polysaccharides among others have been problematic due to the dense nature of the gel phases. While the pore size (about 10 nm) in these gels permit entrapment and/or attachment of the nucleic acid probes within the gel, the solution-phase DNA Target, which is typically many times longer than the nucleic acid probe, is blocked from penetrating the gel matrix thereby limiting use of these gel phase systems due to poor solution-phase access to the Target DNA.

Thus, the prior art is deficient in methods of DNA based pathogen analysis that interrogates a multiplicity of samples, uses fewer chemical and labile products, reduces processing steps and provides faster results while maintaining accuracy, specificity and reliability. The present invention fulfills this long-standing need and desire in the art.

SUMMARY OF THE INVENTION

The present invention is directed to a covalent 3-dimensional lattice microarray system for DNA detection and analysis. The system comprises a solid support having chemically activatable groups on its surface, a plurality of bifunctional polymer linkers covalently attached to the solid support and a plurality of nucleic acid probes covalently attached to the bifunctional polymer linkers.

The present invention is directed to an adsorptive 3-dimensional lattice microarray system for DNA detection and analysis. The system comprises a solid support having no chemically activatable groups on its surface, a plurality of bifunctional polymer linkers attached to the solid support by non-covalent adsorption and a plurality of nucleic acid probes attached covalently to the bifunctional polymer linkers.

The present invention is also directed to a method for fabricating a 3-dimensional lattice microarray system. The method comprises the steps of contacting the solid support with a formulation comprising a plurality of nucleic acid probes, a plurality of fluorescent bifunctional polymer linkers and a solvent mixture comprising water and a boiling point water-miscible liquid; performing a first attachment to attach the fluorescent bifunctional polymer linker to the solid support, evaporating the water in the sample and performing a second attachment step to covalently attach the nucleic acid probes to the fluorescent bifunctional polymer linker.

The present invention is further directed to a customizable kit comprising the solid support, a plurality of fluorescent labeled bifunctional polymer linkers, solvents and instructions for fabricating the microarray using a plurality of custom designed nucleic acid probes relevant to an end user.

BRIEF DESCRIPTION OF THE DRAWINGS

These and other features, aspects, and advantages of the embodiments of the present disclosure will become better understood when the following detailed description is read with reference to the accompanying drawings in which like characters represent like parts throughout the drawing, wherein:

FIG. 1A shows the components—unmodified nucleic acid probe, amine-functionalized (NH) bifunctional polymer linker and amine-functionalized (NH) fluorescently labeled bifunctional polymer linker in a solvent comprising water and a high boiling point water-miscible liquid, and a solid support with chemically activatable groups (X). FIG. 1B shows the first step reaction of the bifunctional polymer linker with the chemically activated solid support where the bifunctional polymer linker becomes covalently attached by the amine groups to the chemically activated groups on the solid support. FIG. 1C shows the second step of concentration via evaporation of water from the solvent to increase the concentration of the reactants—nucleic acid probes and bifunctional polymer linker. FIG. 1D shows the third step of UV crosslinking of the nucleic acid probes via thymidine base to the bifunctional polymer linker within evaporated surface, which in some instances also serves to covalently link adjacent bifunctional polymeric linkers together via crosslinking to the nucleic acid Probe.

FIG. 2A shows the components; unmodified nucleic acid probe and functionalized ($R_n$) bifunctional polymer linker and similarly functionalized fluorescent labeled bifunctional polymer linker in a solvent comprising water and a high boiling point water-miscible liquid, and a solid support, wherein the $R_n$ group is compatible for adsorbing to the solid support surface. FIG. 2B shows the first step adsorption of the bifunctional polymer linker on the solid support where the bifunctional polymer linkers become non-covalently attached by the $R_n$ groups to the solid support. FIG. 2C shows the second step of concentration via evaporation of water from the solvent to increase the concentration of the reactants—Nucleic acid probes and bifunctional polymer linker. FIG. 2D shows the third step of UV crosslinking of the nucleic acid probes via thymidine base to the bifunctional polymer linker and other nucleic acid probes within the evaporated surface which in some instances also serves to covalently link adjacent bifunctional polymeric linkers together via crosslinking to the nucleic acid Probe.

FIG. 3A shows an imaged microarray after hybridization and washing, as visualized at 635 nm. The 635 nm image is derived from signals from the (red) CY5 fluor attached to the 5' terminus of the bifunctional polymer linker (OligodT) which had been introduced during microarray fabrication as a positional marker in each microarray spot.

FIG. 3B shows a microarray imaged after hybridization and washing as visualized at 532 nm. The 532 nm image is derived from signals from the (green) CY3 fluor attached to the 5' terminus of PCR amplified DNA obtained during PCR Reaction #2 of a DNA containing sample.

FIG. 3C shows an imaged microarray after hybridization and washing as visualized with both the 532 nm and 635 nm images superimposed. The superimposed images display the utility of parallel attachment of a Cy5-labelled OligodT positional marker relative to the sequence specific binding of the CY3-labelled PCR product.

FIGS. 11A-11B shows representative microarray hybridization data obtained from purified bacterial DNA standards (FIG. 11A) and purified fungal DNA standards (FIG. 11B). In each case, the purified bacterial DNA is PCR amplified as though it were an unpurified DNA, then hybridized on the microarray via the microarray probes described above. The data show that in this microarray format, each of the bacteria can be specifically identified via room temperature hybridization and washing. Similarly, the purified fungal DNA is PCR amplified as though it were an unpurified DNA, then hybridized on the microarray via the microarray probes described above. The data show that in this microarray format, each of the fungal DNAs can be specifically identified via room temperature hybridization and washing.

FIG. 13 shows representative microarray hybridization data obtained from a representative raw *Cannabis* wash sample compared to a representative (raw) highly characterized, *candida* samples. In each case, the raw pathogen complement of each sample is PCR amplified, then hybridized on the microarray via the microarray probes described above. The data show that in this microarray format, specific fungal contaminants can be specifically identified via room temperature hybridization and washing on either raw *Cannabis* wash or cloned fungal sample.

FIG. 16 shows diagrams for sample collection and preparation from two methods. Both the tape pull and wash method are used to process samples to provide a solution for microbial detection via microarray analysis.

DETAILED DESCRIPTION OF THE INVENTION

Figure 1A:
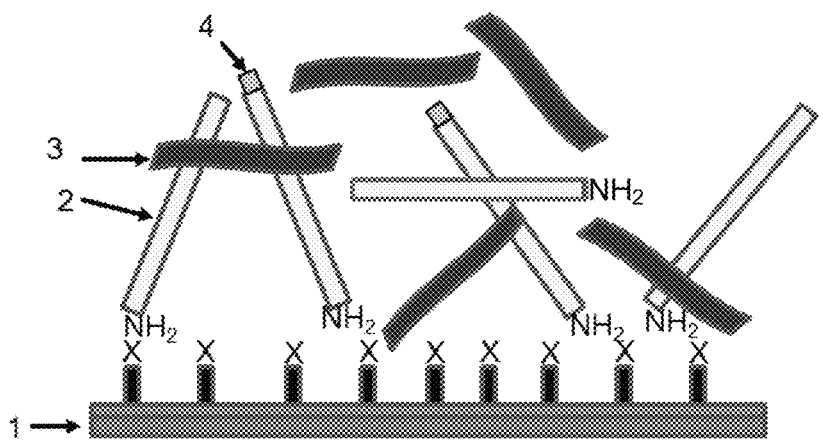
FIGS. 1A-1D illustrate a covalent microarray system comprising probes and bifunctional labels printed on an activated surface.

In one embodiment of this invention, there is provided a 3-dimensional lattice microarray system for screening a sample for the presence of a multiplicity of DNA. The system comprises a chemically activatable solid support, a bifunctional polymer linker and a plurality of nucleic acid probes designed to identify sequence determinants in plant, animal or pathogen DNA.

In this embodiment, the solid support may be made of any suitable material known in the art including but not limited to borosilicate glass, a thermoplastic acrylic resin such as poly(methylmethacrylate-VSUVT (PMMA-VSUVT), a cycloolefin polymers such as ZEONOR® 1060R, metals including, but not limited to gold and platinum, plastics including, but not limited to polyethylene terephthalate, polycarbonate, nylon, ceramics including, but not limited to $TiO_2$, and Indium tin oxide (ITO) and engineered carbon surfaces including, but not limited to graphene. The solid support has a front surface and a back surface and may be activated on the front surface with suitable chemicals which include but are not limited to epoxysilane, isocyanate, succinimide, carbodiimide, aldehyde and maleimide. These are well known in the art and one of ordinary skill in this art would be able to readily functionalize any of these supports as desired. In a preferred embodiment, the solid support is epoxysilane functionalized borosilicate glass support.

In this embodiment, the bifunctional polymer linker has a top domain and a bottom end. On the bottom end is attached a first reactive moiety that allows covalent attachment to the chemically activatable groups in the solid support. Examples of first reactive moieties include but are not limited to an amine group, a thiol group and an aldehyde group. Preferably, the first reactive moiety is an amine group. On the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. The bifunctional polymer linker may be an oligonucleotide such as OligodT, an amino polysaccharide such as chitosan, a polyamine such as spermine, spermidine, cadaverine and putrescine, a polyamino acid, with a lysine or histidine, or any other polymeric compounds with dual functional groups which can be attached to the chemically activatable solid support on the bottom end, and the nucleic acid probes on the top domain. Preferably, the bifunctional polymer linker is OligodT having an amine group at the 5' end.

In this embodiment, the bifunctional polymer linker may be unmodified. Alternatively, the bifunctional polymer linker has a color or fluorescent label attached covalently. Examples of fluorescent labels include, but are not limited to a Cy5, a DYLIGHT™ DY647, a ALEXA FLUOR® 647, a Cy3, a DYLIGHT™ DY547, or a ALEXA FLUOR® 550. These may be attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker is Cy5-labeled OligodT having an amine group attached at its 3'terminus for covalent attachment to an activated surface on the solid support.

Also in this embodiment, the present invention provides a plurality of nucleic acid probes designed with the purpose of identifying sequence determinants in plants, animals or pathogens. The nucleic acid probes are synthetic oligonucleotides and have terminal thymidine bases at their 5' and 3' end. The thymidine bases permit covalent attachment of the nucleic acid probes to the bifunctional polymer linker by any standard coupling procedures including but not limited to chemical, photochemical and thermal coupling. Preferably, covalent attachment of the nucleic acid probes to the bifunctional polymer linker is by photochemical means using ultraviolet light.

In this embodiment, the fluorescent label (fluorescent tag) attached to the bifunctional polymer linker is beneficial since it allows the user to image and detect the position of the individual nucleic acid probes ("spot") printed on the microarray. By using two different fluorescent labels, one for the bifunctional polymer linker and the second for the amplicons generated from the DNA being queried, the user can obtain a superimposed image that allows parallel detection of those nucleic acid probes which have been hybridized with amplicons. This is advantageous since it helps in identifying the plant or pathogen comprised in the sample using suitable computer and software, assisted by a database correlating nucleic acid probe sequence and microarray location of this sequence with a known DNA signature in plants, animals or pathogens. Any emitter/acceptor fluorescent label pairs known in the art may be used. For example, the bifunctional polymer linker may be labeled with emitters such as a Cy5, DYLIGHT™ DY647, or ALEXA FLUOR® 647, while the amplicons may be labeled with acceptors such as Cy3, DYLIGHT™ DY547, or ALEXA FLUOR® 550. Preferably, the emitter is Cy5 and the acceptor is Cy3.

In another embodiment of this invention, there is provided a 3-dimensional lattice microarray system for screening a sample for the presence of a multiplicity of DNA. The system comprises a solid support, a fluorescent labeled bifunctional polymer linker and a plurality of nucleic acid probes designed to identify sequence determinants in plant, animal or pathogen DNA.

In this embodiment, the solid support has a front surface and a back surface. The front surface has non-covalent adsorptive properties for specific functionalized group(s) present in the fluorescent labeled bifunctional polymer linker (described below). Examples of such solid support include, but are not limited to borosilicate glass, SiO2, metals including, but not limited to gold and platinum, plastics including, but not limited to polyethylene terephthalate, polycarbonate, nylon, ceramics including, but not limited to $TiO_2$, and Indium tin oxide (ITO) and engineered carbon surfaces including, but not limited to graphene.

In this embodiment, the fluorescent labeled bifunctional polymer linker has a top domain and a bottom end. On the bottom end is attached one or more functional groups (designated by "$R_n$") that are compatible for non-covalent adsorptive attachment with the front surface of the solid support. Examples of compatible R groups include, but are not limited to, single stranded nucleic acids (example, OligodT), amine-polysaccharide (example, chitosan), extended planar hydrophobic groups (example, digoxigenin, pyrene, Cy-5 dye).

Further in this embodiment, on the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. To the bottom end of the bifunctional polymer linker may be attached polymeric molecules including, but not limited to an oligonucleotide such as OligodT, an amino polysaccharide such as chitosan, a polyamine such as spermine, spermidine, cadaverine and putrescine, a polyamino acid, with a lysine or histidine, or OligodT that is modified at its 5' end with a digoxigenin, a pyrene or a Cy5 or any other polymeric molecules with or without chemical modification suitable for non-covalent attachment to the solid support. On the top domain of these bifunctional polymer linkers is attached, the nucleic acid probes. Preferably, the bifunctional polymer linker is OligodT.

In one aspect of this embodiment, the bifunctional polymer linker is unmodified. Alternatively, the bifunctional polymer linker may be a fluorescent labeled bifunctional polymer linker. The fluorescent label may be, but is not limited to a Cy5, a DYLIGHT™ DY647, a ALEXA FLUOR® 647, a Cy3, a DYLIGHT™ DY547, or a ALEXA FLUOR® 550 attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker is Cy5-labeled OligodT.

Also in this embodiment, the present invention provides a plurality of nucleic acid probes designed with the purpose of identifying sequence determinants in plants, animals or pathogens. The nucleic acid probes are synthetic oligonucleotides and have terminal thymidine bases at their 5' and 3' end. The thymidine bases permit covalent attachment of the nucleic acid probes to the bifunctional polymer linker by any standard coupling procedures including but not limited to chemical, photochemical and thermal coupling. Preferably, covalent attachment of the nucleic acid probes to the bifunctional polymer linker is by photochemical means using ultraviolet light.

In this embodiment, the fluorescent label (fluorescent tag) attached to the bifunctional polymer linker is beneficial since it allows the user to image and detect the position of the individual nucleic acid probes ("spot") printed on the microarray. By using two different fluorescent labels, one for the bifunctional polymer linker and the second for the amplicons generated from the DNA being queried, the user can obtain a superimposed image that allows parallel detection of those nucleic acid probes which have been hybridized with amplicons. This is advantageous since it helps in identifying the plant or pathogen comprised in the sample using suitable computer and software, assisted by a database correlating nucleic acid probe sequence and microarray location of this sequence with a known DNA signature in plants, animals or pathogens. Any emitter/acceptor fluorescent label pairs known in the art may be used. For example, the bifunctional polymer linker may be labeled with emitters such as a Cy5, DYLIGHT™ DY647, or ALEXA FLUOR® 647, while the amplicons may be labeled with acceptors such as Cy3, DYLIGHT™ DY547, or ALEXA FLUOR® 550. Preferably, the emitter is Cy5 and the acceptor is Cy3.

In yet another embodiment of this invention, there is provided a method for fabricating a 3-dimensional lattice microarray system for the purpose of screening a sample for the presence of a multiplicity of DNA in a sample. The method comprises, contacting a solid support with a formulation comprising a plurality of nucleic acid probes, a plurality of fluorescent bifunctional polymer linkers and a solvent mixture comprising water and a high boiling point, water-miscible liquid, allowing a first attachment between the fluorescent bifunctional polymer linkers and the solid support to proceed, evaporating the water in the solvent mixture thereby concentrating the nucleic acid probes and fluorescent labeled bifunctional polymer linkers, allowing a second attachment between the nucleic acid probes and the fluorescent bifunctional polymer linker, and washing the solid support with at least once to remove unattached fluorescent bifunctional polymer linkers and nucleic acid probes.

In this embodiment, the contacting step is achieved by standard printing methods known in the art including, but not limited to piezo-electric printing, contact printing, ink jet printing and pipetting, which allow an uniform application of the formulation on the activated support. For this, any suitable solid support known in the art including but not limited to borosilicate glass, a polycarbonate, a graphene, a gold, a thermoplastic acrylic resin such as poly(methylmethacrylate-VSUVT (PMMA-VSUVT) and a cycloolefin polymer such as ZEONOR® 1060R may be employed.

In one aspect of this embodiment, the first attachment of the bifunctional polymer linker to the solid support is by non-covalent means such as by adsorption or electrostatic binding. In this case, the bifunctional polymer linkers with one or more functional groups (designated by "$R_n$") on the bottom end, that are compatible for attachment with the front surface of the solid support will be used. Examples of compatible R groups include, but are not limited to, single stranded nucleic acids (example, OligodT), amine-polysaccharide (example, chitosan), extended planar hydrophobic groups (example, digoxigenin, pyrene, Cy-5 dye). In another aspect of this embodiment, the first attachment of the bifunctional polymer linker to the solid support is by covalent coupling between chemically activatable groups on the solid support and a first reactive moiety on the bottom end of the bifunctional polymer linker. Suitable chemicals including but are not limited to epoxysilane, isocyanate, succinimide, carbodiimide, aldehyde and maleimide may be used for activating the support. These are well known in the art and one of ordinary skill in this art would be able to readily functionalize any of these supports as desired. In a preferred embodiment, a borosilicate glass support that is epoxysilane functionalized is used. Examples of first reactive moieties amenable to covalent first attachment include, but are not limited to an amine group, a thiol group and an aldehyde group. Preferably, the first reactive moiety is an amine group.

In this embodiment, the bifunctional polymer linker has a second reactive moiety attached at the top domain. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. Preferably, the second reactive moiety is thymidine. In this aspect of the invention, the bifunctional polymer linker may be an oligonucleotide such as OligodT, an amino polysaccharide such as chitosan, a polyamine such as spermine, spermidine, cadaverine and putrescine, a polyamino acid, with a lysine or histidine, or any other polymeric compounds with dual functional groups which can be attached to the chemically activatable solid support on the bottom end, and the nucleic acid probes on the top domain. Preferably, the bifunctional polymer linker is OligodT having an amine group at the 5' end.

In this embodiment, the bifunctional polymer linkers are modified with a fluorescent label. Examples of fluorescent labels include but are not limited Cy5, DYLIGHT™ DY647, ALEXA FLUOR® 647, Cy3, DYLIGHT™ DY547 and ALEXA FLUOR® 550 attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker used for fabricating the microarray is Cy5-labeled OligodT.

The method of fabricating the microarray requires use of a solvent mixture comprising water and a water-miscible liquid having a boiling point above 100° C. This liquid may be any suitable water-miscible liquid with a boiling point higher than that of water, so that all the solvent is not lost during the evaporation step. This allows the molecular reactants—nucleic acid probes and bifunctional linkers to be progressively concentrated during evaporation. Such controlled evaporation is crucial to the present invention since it controls the vertical spacing between nucleic acid probes their avoiding steric hindrance during the hybridization steps thereby improving accuracy and precision of the microarray. Examples of high boiling point water-miscible solvent include but are not limited to glycerol, DMSO and propanediol. The ratio or water to high boiling point solvent is kept between 10:1 and 100:1 whereby, in the two extremes, upon equilibrium, volume of the fluid phase will reduce due to water evaporation to between $1/100$th and $1/10^{th}$ of the original volume, thus giving rise to a 100-fold to 10-fold increase in reactant concentration. In a preferred embodiment, the water-miscible solvent is propanediol and the water to propanediol ratio is 100:1.

Further in this embodiment, the nucleic acid probes used in the method of microarray fabrication are designed with terminal thymidine bases at their 5' and 3' end. The thymidine bases permit covalent attachment of the nucleic acid probes to the bifunctional polymer linker by any standard coupling procedures including but not limited to chemical, photochemical and thermal coupling during the fabrication process. Preferably, coupling of the nucleic acid probes to the fluorescent labeled bifunctional polymer linkers is by photochemical covalent crosslinking.

In yet another embodiment of this invention, there is provided a customizable microarray kit. The kit comprises a solid support, a plurality of fluorescent labeled bifunctional polymer linkers, nucleic acid probes and a solvent mixture comprising water and one or more of a water-miscible liquid having a boiling point above 100° C., and instructions to use the kit. Each of the components comprising this kit may be individually customized prior to shipping based on the goals of the end user.

In this embodiment, the solid support has a front surface and a back surface and made of any suitable material known in the art including but not limited to borosilicate glass, a polycarbonate, a graphene, a gold, a thermoplastic acrylic resin such as poly(methylmethacrylate-VSUVT (PMMA-VSUVT) and a cycloolefin polymer such as ZEONOR® 1060R.

In one aspect of this embodiment, the solid support is unmodified and has properties capable of non-covalent attachment to groups in the bifunctional polymer linker. Alternatively, the solid support is activated on the front surface with chemically activatable groups which include but are not limited to epoxysilane, isocyanate, succinimide, carbodiimide, aldehyde and maleimide. These are well known in the art and one of ordinary skill in this art would be able to readily functionalize any of these supports as desired. In a preferred embodiment, the solid support is epoxysilane functionalized borosilicate glass support.

In this embodiment, the bifunctional polymer linker has a top domain and a bottom end. In one aspect of this embodiment, to the bottom end of the bifunctional polymer linker are attached one or more functional groups (designated by "$R_n$"), which are compatible for attachment with the front surface of the solid support in a non-covalent binding. Examples of such compatible R groups include, but are not limited to, single stranded nucleic acids (example, OligodT), amine-polysaccharide (example, chitosan), extended planar hydrophobic groups (example, digoxigenin, pyrene, Cy-5 dye). Alternatively, to the bottom end of the bifunctional polymer linker are attached a first reactive moiety that allows covalent attachment to chemically activatable groups in the solid support. Examples of first reactive moieties include but are not limited to an amine group, a thiol group and an aldehyde group. Preferably, the first reactive moiety is an amine group.

Further in this embodiment, on the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. The bifunctional polymer linker may be an oligonucleotide such as OligodT, an amino polysaccharide such as chitosan, a polyamine such as spermine, spermidine, cadaverine and putrescine, a polyamino acid, with a lysine or histidine, or any other polymeric compounds with dual functional groups for attachment to the solid support from the bottom end, and the nucleic acid probes from the top domain.

In one aspect of this embodiment, the bifunctional polymer linkers are modified with a fluorescent label. Alternatively, the bifunctional polymer linker may be a fluorescent labeled bifunctional polymer linker where the fluorescent label is either of Cy5, DYLIGHT™ DY647, ALEXA FLUOR® 647, Cy3, DYLIGHT™ DY547, or ALEXA FLUOR® 550 attached to any reactive group including but not limited to, amine, thiol, aldehyde, sugar amido and carboxy on the bifunctional polymer linker. The chemistries of such reactive groups are well known in the art and one or ordinary skill can readily identify a suitable group on a selected bifunctional polymer linker for attaching the fluorescent label. Preferably, the bifunctional polymer linker is Cy5-labeled OligodT.

Also in this embodiment, the present invention provides a plurality of nucleic acid probes designed with the purpose of identifying sequence determinants in plants, animals or pathogens. The nucleic acid probes are synthetic oligonucleotides and have terminal thymidine bases at their 5' and 3' end. The thymidine bases permit covalent attachment of the nucleic acid probes to the bifunctional polymer linker by any standard coupling procedures including but not limited to chemical, photochemical and thermal coupling. Preferably, covalent attachment of the nucleic acid probes to the bifunctional polymer linker is by photochemical means using ultraviolet light.

In yet another embodiment of this invention there is provided a method for detecting the presence of one or more pathogens in a plant sample. In this embodiment, the pathogen may be a human pathogen, an animal pathogen or a plant pathogen, such as a bacterium, a fungus, a virus, a yeast, algae or a protozoan or a combination thereof. These pathogens may be present as constituents of the soil, soilless growth media, hydroponic growth media or water in which the plant sample was grown. The method comprises harvesting the pathogens from the plant sample, isolating total nucleic acids comprising pathogen DNA, performing a first amplification for generating one or more amplicons from the one or more pathogens present in the sample in a single, simultaneous step; performing a labeling amplification using as template, the one or more amplicons generated in the first amplification step to generate fluorescent labeled second amplicons; hybridizing the second amplicons with the nucleic acid probes immobilized on the fabricated self-assembled, 3-dimensional lattice microarray described above and imaging the microarray to detect the fluorescent signal, which indicates presence of the one or more pathogens in a plant sample. In this embodiment, the pathogens present on the plant surface may be harvested by washing the plant with water to recover the pathogens, followed by concentrating by filtration on a sterile 0.4 µm filter. In another aspect of this embodiment, pathogens within the plant tissue may be harvested by fluidizing the plant tissue sample and pathogens, followed by centrifuging to get a pellet of plant cells and pathogen cells. In either embodiment, the harvested sample is disrupted to release the total nucleic acids which is used in the subsequent steps without further purification.

Also in this embodiment, the sample comprising nucleic acids from pathogens (external pathogens) or nucleic acids from both pathogens and plant (internal pathogens) is used to perform a first amplification of pathogen DNA using pathogen-specific first primer pairs to obtain one or more pathogen-specific first amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. In one embodiment, the pathogen is a bacterium and the first primer pairs have sequences shown in SEQ ID NOS: 1-12. In another embodiment, the pathogen is a fungus and the first primer pairs have sequences shown in SEQ ID NOS: 13-16. An aliquot of first amplicons so generated is used as template for a second, labelling PCR amplification using fluorescent labeled second primer pairs. The second primer pairs are designed to amplify an internal flanking region in the one or more first amplicons to obtain one or more first fluorescent labeled second amplicons. In one embodiment, the pathogen is a bacterium and the second primer pairs have sequences shown in SEQ ID NOS: 19-30. In another embodiment, the pathogen is a fungus and the second primer pairs have sequences shown in SEQ ID NOS: 31-34.

Further in this embodiment, the fluorescent labeled second amplicons are hybridized on a 3-dimensional lattice microarray system having a plurality of nucleic acid probes as described in detail above. In this embodiment, the bifunctional polymer linker has a fluorescent label (that is different from the label on the second amplicon) attached whereby, imaging the microarray after hybridization and washing results in two distinct fluorescent signals—the signal from the fluorescent bifunctional polymer linker which is covalently linked to the nucleic acid probe during fabrication, which would be detected in each spot comprised in the microarray, and a second amplicon signal that would be detected only in those spots where the nucleic acid probe sequence is complementary to the second amplicon (originally derived by amplification from the pathogen DNA in the sample). Thus, superimposing the two images using a computer provides beneficial attributes to the system and method claimed in this invention since one can readily identify the plant or pathogen comprised in the sample from a database that correlates nucleic acid probe sequence and microarray location of this sequence with a known DNA signature in plants or pathogens. In a preferred embodiment, the bacterial nucleic acid probes having sequences shown in SEQ ID NOS: 37-85. and fungal nucleic acid probes having sequences shown in SEQ ID NOS: 86-125 may be used for this purpose.

Further to this embodiment is a method for detecting plant DNA. The plant may be a terrestrial plant such as a *Humulus* or a *Cannabis*, an aquatic plant, an epiphytic plant or a lithophytic plant that grows in soil, soilless media, hydroponic growth media or water. In a preferred aspect, the plant is a *Cannabis*. This method comprises the steps of performing an amplification on an unpurified complex nucleic acid sample using plant-specific first primer pairs to generate plant-specific first amplicons. In one aspect of this embodiment, the first primer pair has sequences shown in SEQ ID NOS: 17-18. Any DNA amplification methodology, including loop-mediated isothermal amplification (LAMP) or polymerase chain reaction (PCR) that can selectively amplify the DNA complement in the sample may be employed. Preferably the amplification is by PCR. The first amplicons so generated are used as template for a labeling amplification step using fluorescent labeled second primer pairs that are designed to amplify an internal flanking region in the one or more of first amplicons generated in the first amplification step to generate one or more first fluorescent labeled second amplicons. In one embodiment, the second primer pair has sequences shown in SEQ ID NOS: 35-36. The second amplicons are hybridized on a 3-dimensional lattice microarray system having a plurality of plant-specific nucleic acid probes, and the microarrays imaged and analyzed as described above for identifying pathogen DNA. In one aspect of this embodiment, the hybridization nucleic acid probes have sequences shown in SEQ ID NOS: 126-128.

In yet another embodiment of this invention, there is provided a method for simultaneously detecting resident pathogen DNA and plant DNA in a plant sample in a single assay. In this embodiment, the pathogen may be a human pathogen, an animal pathogen or a plant pathogen, which may be a bacterium, a fungus, a virus, a yeast, algae or a protozoan or a combination thereof. These pathogens may be present as constituents of the soil, soilless growth media, hydroponic growth media or water in which the plant sample was grown. The plant may be a terrestrial plant such as a *Humulus* or a *Cannabis*, an aquatic plant, an epiphytic plant or a lithophytic plant that grows in soil, soilless media, hydroponic growth media or water. Preferably, the plant is a *Cannabis*.

In this embodiment, the method comprises harvesting a plant tissue sample potentially comprising one or more pathogens, fluidizing the plant tissue sample and the one or more pathogens and isolating total nucleic acids comprising DNA from at least the plant tissue and DNA from the one or more pathogens. In one aspect of this embodiment, the step of isolating total nucleic acids comprises centrifuging the fluidized sample to get a pellet of plant cells and pathogen cells which are disrupted to release the total nucleic acids, which are used in the subsequent steps without further purification.

Further in this embodiment, a first amplification is performed on the unpurified total nucleic acid sample using one or more of a first primer pair each selective for the one or more pathogen DNA and one or more of a second primer pair selective for the plant DNA to generate one or more pathogen-specific first amplicons and one or more plant-specific second amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. In one embodiment, the pathogen is a bacterium and the first primer pairs have sequences shown in SEQ ID NOS: 1-12. In another embodiment, the pathogen is a fungus and the first primer pairs have sequences shown in SEQ ID NOS: 13-16. In either of these embodiments, the plant-specific second primer pairs have sequences shown in SEQ ID NOS: 35-36. An aliquot of the first and second amplicons so generated is used as a template for a second, labeling PCR amplification step using fluorescent labeled third primer pairs having a sequence complementary to an internal flanking region in the one or more pathogen-specific first amplicons and fluorescent labeled fourth primer pairs having a sequence complementary to an internal flanking region in the one or more plant-specific second amplicons. Any DNA amplification methodology, including loop-mediated isothermal amplification (LAMP) or polymerase chain reaction (PCR) that can selectively amplify the DNA complement in the sample may be employed. In a preferred embodiment, the amplification is by PCR. In one embodiment, the pathogen is a bacterium and the third primer pairs have sequences shown in SEQ ID NOS: 19-30. In another embodiment, the pathogen is a fungus and the third primer pairs have sequences shown in SEQ ID NOS: 31-34. In either of these embodiments, the plant-specific fourth primer pairs have sequences shown in SEQ ID NOS: 35-36. The labeling PCR step results in generation of first fluorescent labeled third amplicons and second fluorescent labeled fourth amplicons corresponding to the pathogen and plant DNA respectively in the original harvested sample. These amplicons are then hybridized on a 3-dimensional lattice microarray system having a plurality of nucleic acid probes specific to sequence determinants in pathogen DNA or plant DNA. Bacterial nucleic acid probes having sequences shown in SEQ ID NOS: 37-85, fungal nucleic acid probes having sequences shown in SEQ ID NOS: 86-125 and plant nucleic acid probes having sequences shown in SEQ ID NOS: 126-128. may be used for this purpose. After hybridization, unhybridized amplicons are removed by washing and the microarray imaged. Detection of the first fluorescent labeled third amplicon signal indicates presence of pathogens in the plant sample. Detecting the second fluorescent labeled fourth amplicon indicates presence of the plant DNA. Superimposing these two signals with the third fluorescent signal from the fluorescent bifunctional polymer linker-coupled nucleic acid probes allow simultaneous identification of the pathogen and plant in the sample by correlating nucleic acid probe sequence and microarray location of this sequence with a known DNA signature in plants or pathogens. These features provide beneficial attributes to the system and method claimed in this invention.

In yet another embodiment of the present disclosure there is provided an improved method for DNA based pathogen analysis. The embodiments of the present disclosure use DNA amplification methodologies, including loop-mediated isothermal amplification (LAMP) or polymerase chain reaction (PCR) tests that can selectively amplify the DNA complement of that plant material using unpurified plant and pathogen material. The embodiments are also based on the use of aforementioned PCR-amplified DNA as the substrate for microarray-based hybridization analysis, wherein the hybridization is made simple because the nucleic acid probes used to interrogate the DNA of such pathogens are optimized to function at room temperature. This enables the use of the above-mentioned microarray test at ambient temperature, thus bypassing the prior art requirement that testing be supported by an exogenous temperature-regulating device.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Fabrication of 3-Dimensional Lattice Microarray Systems

The present invention teaches a way to link a nucleic acid probe to a solid support surface via the use of a bifunctional polymeric linker. The nucleic acid probe can be a PCR amplicon, synthetic oligonucleotides, isothermal amplification products, plasmids or genomic DNA fragment in a single stranded or double stranded form. The invention can be sub-divided into two classes, based on the nature of the underlying surface to which the nucleic acid probe would be linked.

1. Covalent Microarray System with Activated Solid Support.

The covalent attachment of any one of these nucleic acid probes does not occur to the underlying surface directly, but is instead mediated through a relatively long, bi-functional polymeric linker that is capable of both chemical reaction with the surface and also capable of efficient UV-initiated crosslinking with the nucleic acid probe. The mechanics of this process is spontaneous 3D self assembly and is illustrated in FIG. 1A-FIG. 1D. As seen in FIG. 1A, the components required to fabricate this microarray system are:

(a) an unmodified nucleic acid probe 3 such as an oligonucleotide, PCR or isothermal amplicon, plasmid or genomic DNA;

(b) a chemically activatable surface 1 with chemically activatable groups (designated "X") compatible for reacting with a primary amine such as. epoxysilane, isocyanate, succinimide, carbodiimide, aldehyde.

(c) bifunctional polymer linkers 2 such as a natural or modified OligodT, amino polysaccharide, amino polypeptide suitable for coupling to chemically activatable groups on the support surface, each attached with a fluorescent label 4; and (d) a solvent comprising water and a high boiling point, water-miscible liquid such as glycerol, DMSO or propanediol (water to solvent ratio between 10:1 and 100:1).

Table 1 shows examples of chemically activatable groups and matched reactive groups on the bifunctional polymer linker for mere illustration purposes only and does not in any way preclude use of other combinations of matched reactive pairs.

TABLE 1

Covalent Attachment of Bifunctional Polymeric Linker to an Activated Surfaces

| Activated Surface Moiety | Matched Reactive Group on Bifunctional Linker | Specific Implementation as Bifunctional polymeric linker |
|---|---|---|
| Epoxysilane | Primary Amine | (1) Amine-modified OligodT (20-60 bases) (2) Chitosan (20-60 subunits) (3) Lysine containing polypeptide (20-60aa) |
| EDC Activated Carboxylic Acid | Primary Amine | (4) Amine-modified OligodT (20-60 bases) (5) Chitosan (20-60 subunits) (6) Lysine containing polypeptide (20-60aa) |
| N-hydroxysuccinimide (NHS) | Primary Amine | (7) Amine-modified OligodT (20-60 bases) (8) Chitosan (20-60 subunits) (9) Lysine containing polypeptide (20-60aa) |

When used in the present invention, the chemically activatable surface, bifunctional polymer linkers and unmodified nucleic acid probes are included as a solution to be applied to a chemically activated surface 4 by ordinary methods of fabrication used to generate DNA Hybridization tests such as contact printing, piezo electric printing, ink jet printing, or pipetting.

Figure 1B:
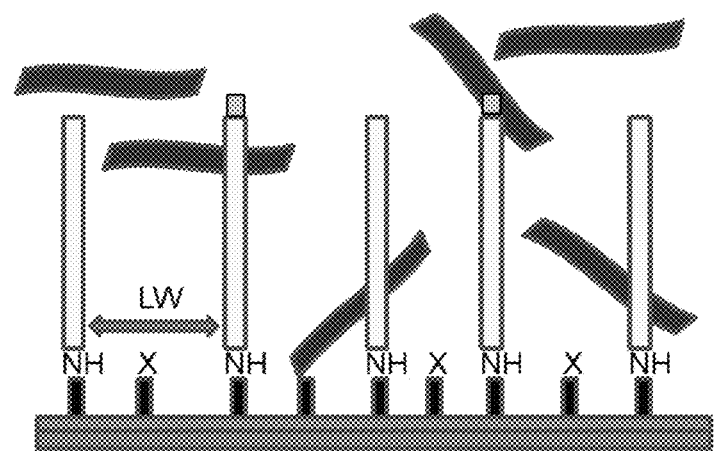

Microarray fabrication begins with application of a mixture of the chemically activatable surface, bifunctional polymer linkers and unmodified nucleic acid probes to the surface. The first step is reaction and covalent attachment of the bifunctional linker to the activated surface (FIG. 1B). In general, the chemical concentration of the bi-functional linker is set to be such that less than 100% of the reactive sites on the surface form a covalent linkage to the bi-functional linker. At such low density, the average distance between bi-functional linker molecules defines a spacing denoted lattice width ("LW" in FIG. 1B).

Figure 1C:
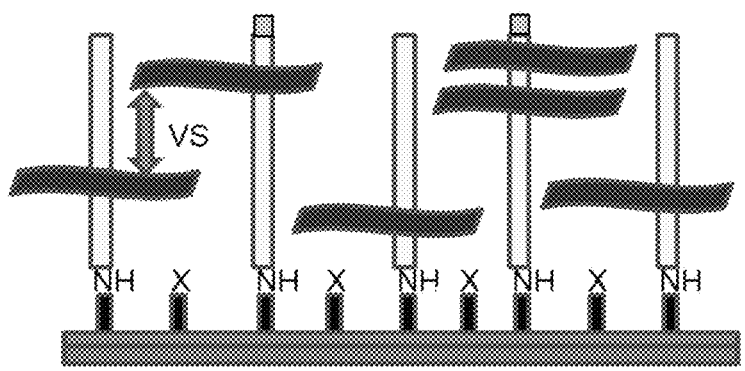

In the second step, the water in the solvent is evaporated to concentrate the DNA and bifunctional linker via evaporation of water from the solvent (FIG. 1C). Generally, use of pure water as the solvent during matrix fabrication is disadvantageous because water is very quickly removed by evaporation due to a high surface area/volume ratio. To overcome this, in the present invention, a mixture of water with a high boiling point water-miscible solvent such as glycerin, DMSO or propanediol was used as solvent. In this case, upon evaporation, the water component will evaporate but not the high boiling point solvent. As a result, molecular reactants—DNA and bifunctional linker are progressively concentrated as the water is lost to evaporation. In the present invention, the ratio or water to high boiling point solvent is kept between 10:1 and 100:1. Thus, in the two extreme cases, upon equilibrium, volume of the fluid phase will reduce due to water evaporation to between $1/100$th and $1/10^{th}$ the original volume, thus giving rise to a 100-fold to 10-fold increase in reactant concentration. Such controlled evaporation is crucial to the present invention since it controls the vertical spacing (Vertical Separation, "VG" in FIG. 1C) between nucleic acid probes, which is inversely related to the extent of evaporative concentration.

Figure 1D:
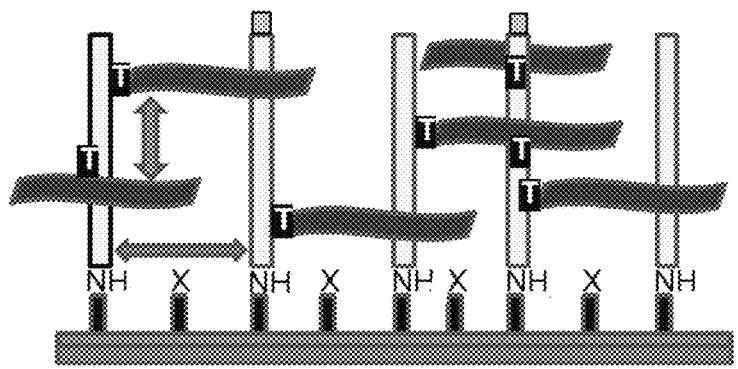

In the third step, the terminal Thymidine bases in the nucleic acid probes are UV crosslinked to the bifunctional linker within the evaporated surface (FIG. 1D). This process is mediated by the well-known photochemical reactivity of the Thymidine base that leads to the formation of covalent linkages to other thymidine bases in DNA or photochemical reaction with proteins and carbohydrates. If the bifunctional crosslinker is OligodT, then the crosslinking reaction will be bi-directional, that is, the photochemistry can be initiated in either the nucleic acid probe or the bifunctional OligodT linker. On the other hand, if the bifunctional linker is an amino polysaccharide such as chitosan or a polyamino acid, with a lysine or histidine in it, then the photochemistry will initiate in the nucleic acid probe, with the bifunctional linker being the target of the photochemistry.

2. Microarray System with Unmodified Solid Support for Non-Covalent Attachment

Figure 2A:
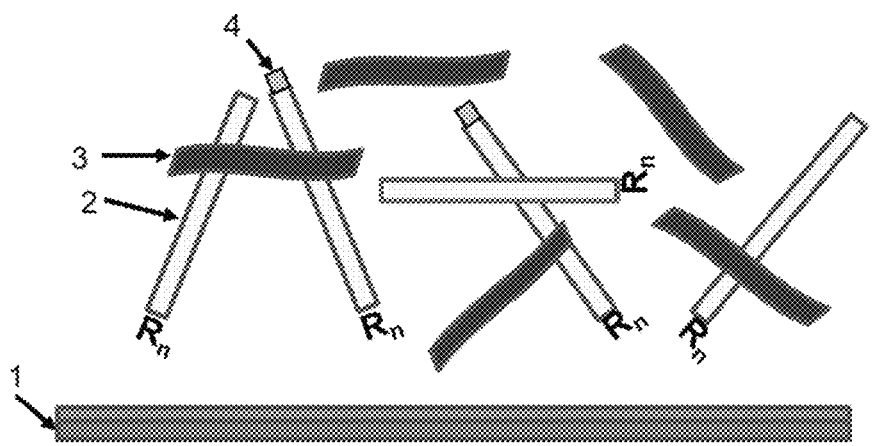
FIGS. 2A-2D illustrate an adsorptive microarray system comprising probes and bifunctional polymeric linkers.

In this microarray system, attachment of the nucleic acid probes does not occur to the underlying surface directly, but is instead mediated through a relatively long, bi-functional polymeric linker that binds non-covalently with the solid support, but covalently with the nucleic acid probes via UV-initiated crosslinking. The mechanics of this process is spontaneous 3D self assembly and is illustrated in FIGS. 2A-2D. As seen in FIG. 2A, the components required to fabricate this microarray system are:

(1) an unmodified nucleic acid probe 3 such as an oligonucleotide, PCR or isothermal amplicon, plasmid or genomic DNA;

(2) an unmodified solid support 1

(3) bifunctional polymer linkers 2 such as OligodT or a amino polysaccharide, amino polypeptide, that inherently have or are modified to have functional groups (designated "R") compatible for adsorptive binding to the solid support, each having a fluorescent label 4; and (4) a solvent comprising water and a high boiling point, water-miscible liquid such as glycerol, DMSO or propanediol (water to solvent ratio between 10:1 and 100:1);

Table 2 shows examples of unmodified support surfaces and matched absorptive groups on the bifunctional polymer linker for mere illustration purposes only and does not in any way precludes the use of other combinations of these.

TABLE 2

Non-Covalent Attachment of Bi-Functional Polymeric Linker to an Inert Surface

| Representative support surface | Matched Adsorptive Group on Bifunctional Linker ($R_n$) | Specific Bifunctional polymeric linker |
|---|---|---|
| glass | Single Stranded Nucleic Acid >10 bases | OligodT (30-60 bases) |
| glass | Amine-Polysaccharide | Chitosan (30-60 subunits) |
| glass | Extended Planar Hydrophobic Groups e.g. Digoxigenin | OligodT (30-60 bases)-5'-Digoxigenin |
| polycarbonate | Single Stranded Nucleic Acid >10 bases | Oligo-dT (30-60 bases) |
| polycarbonate | Amine-Polysaccharide | Chitosan (30-60 subunits) |
| polycarbonate | Extended Planar Hydrophobic Groups e.g. Digoxigenin | OligodT (30-60 bases)-5'-Digoxigenin |
| graphene | Extended Planar Hydrophobic Groups e.g. pyrene | OligodT (30-60 bases)-5'pyrene |
| graphene | Extended Planar Hydrophobic Groups e.g. CY-5 dye | OligodT (30-60 bases)-5'-CY-5 dye |
| graphene | Extended Planar Hydrophobic Groups e.g. Digoxigenin | OligodT (30-60 bases)-5'-Digoxigenin |
| gold | Extended Planar Hydrophobic Groups e.g. pyrene | OligodT (30-60 bases)-5'pyrene |
| gold | Extended Planar Hydrophobic Groups e.g. CY-5 dye | OligodT (30-60 bases)-5' CY-5 dye |
| gold | Extended Planar Hydrophobic Groups e.g. Digoxigenin | OligodT (30-60 bases)-5' Digoxigenin |

When used in the present invention, components 1-3 are included as a solution to be applied to the solid support surface by ordinary methods of fabrication used to generate DNA Hybridization tests such as contact printing, piezo electric printing, ink jet printing, or pipetting.

Figure 2B:
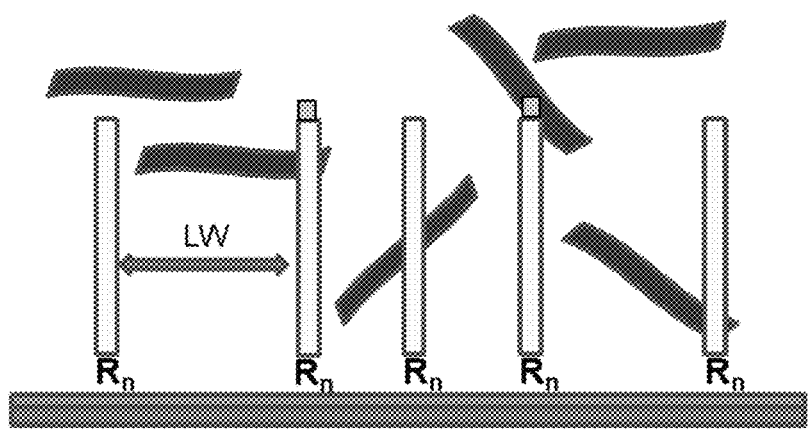

Microarray fabrication begins with application of a mixture of the components (1)-(3) to the surface. The first step is adsorption of the bifunctional linker to the support surface (FIG. 2B). The concentration of the bi-functional linker is set so the average distance between bi-functional linker molecules defines a spacing denoted as lattice width ("LW" in FIG. 2B).

Figure 2C:
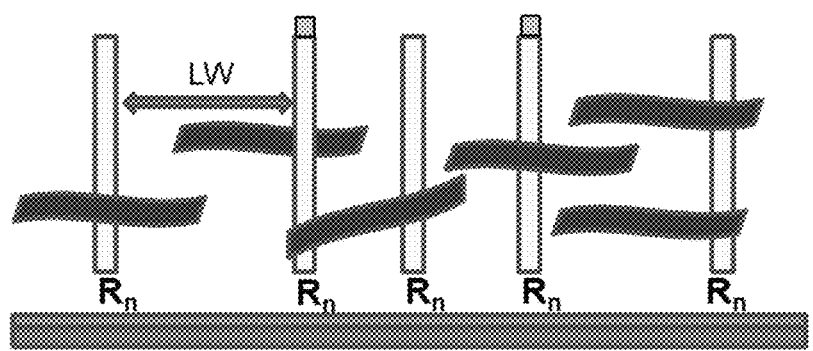

In the second step, the water in the solvent is evaporated to concentrate the DNA and bifunctional linker via evaporation of water from the solvent (FIG. 2C). Generally, use of pure water as the solvent during matrix fabrication is disadvantageous because water is very quickly removed by evaporation due to a high surface area/volume ratio. To overcome this, in the present invention, a mixture of water with a high boiling point water-miscible solvent such as glycerin, DMSO or propanediol was used as solvent. In this case, upon evaporation, the water component will evaporate but not the high boiling point solvent. As a result, molecular reactants—DNA and bifunctional linker are progressively concentrated as the water is lost to evaporation. In the present invention, the ratio or water to high boiling point solvent is kept between 10:1 and 100:1. Thus, in the two extreme cases, upon equilibrium, volume of the fluid phase will reduce due to water evaporation to between 1/100th and 1/10 the original volume, thus giving rise to a 100-fold to 10-fold increase in reactant concentration.

Figure 2D:
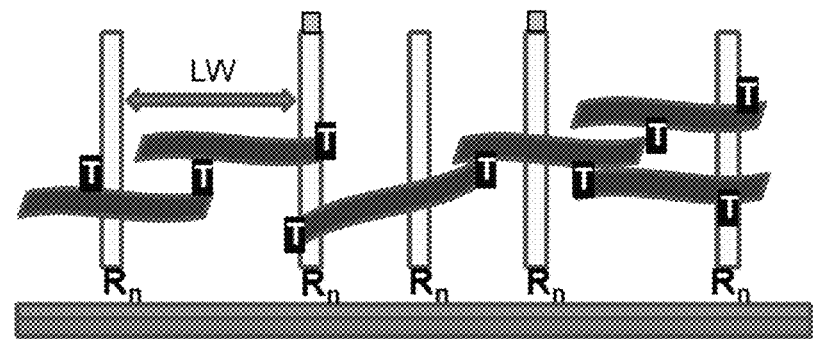

In the third step, the terminal Thymidine bases in the nucleic acid probes are UV crosslinked to the bifunctional linker within the evaporated surface (FIG. 2D). This process is mediated by the well-known photochemical reactivity of the Thymidine base that leads to the formation of covalent linkages to other thymidine bases in DNA or photochemical reaction with proteins and carbohydrates. If the bifunctional crosslinker is OligodT, then the crosslinking reaction will be bi-directional, that is, the photochemistry can be initiated in either the nucleic acid probe or the bifunctional OligodT linker. On the other hand, if the bifunctional linker is an amino polysaccharide such as chitosan or a polyamino acid, with a lysine or histidine in it, then the photochemistry will initiate in the nucleic acid probe, with the bifunctional linker being the target of the photochemistry.

Although such non-covalent adsorption described in the first step is generally weak and reversible, when occurring in isolation, in the present invention it is taught that if many such weak adsorptive events between the bifunctional polymeric linker and the underlying surface occur in close proximity, and if the closely packed polymeric linkers are subsequently linked to each other via Thymidine-mediated photochemical crosslinking, the newly created extended, multi-molecular (crosslinked) complex will be additionally stabilized on the surface, thus creating a stable complex with the surface in the absence of direct covalent bonding to that surface.

The present invention works very efficiently for the linkage of synthetic oligonucleotides as nucleic acid probes to form a microarray-based hybridization device for the analysis of microbial DNA targets. However, it is clear that the same invention may be used to link PCR amplicons, synthetic oligonucleotides, isothermal amplification products, plasmid DNA or genomic DNA fragment as nucleic acid probes. It is also clear that the same technology could be used to manufacture hybridization devices that are not microarrays.

DNA nucleic acid probes were formulated as described in Table 3, to be deployed as described above and illustrated in FIG. 1 or 2. A set of 48 such probes (Table 4) were designed to be specific for various sequence determinants of microbial DNA and each was fabricated so as to present a string of 5-7 T bases at each end, to facilitate their UV-crosslinking to form a covalently linked microarray element, as described above and illustrated in FIG. 1. Each of the 48 different probes was printed in triplicate to form a 144 element (12×12) microarray having sequences shown in Table 3.

TABLE 3

Representative Conditions of use of the Present Invention

| | Unique sequence | 5' labelled OligodT Fluorescent marker |
|---|---|---|
| Nucleic acid probe Type | Oligonucleotide 30-38 bases Long 7 T's at each end | 30 bases Long (marker) |
| Nucleic acid probe Concentration | 50 mM | 0.15 mM |
| Bifunctional Linker | OligodT 30 bases long Primary amine at 3' terminus | |
| Bifunctional Linker Concentration | 1 mM | |
| High Boiling point Solvent | Water:Propanediol, 100:1 | |
| Surface | Epoxysilane on borosilicate glass | |
| UV Crosslinking Dose (mjoule) | 300 millijoule | |

TABLE 4

Nucleic acid probes Linked to the
Microarray Surface via the Present Invention

| SEQ ID NO: 132 | Negative control | TTTTTTCTACTACCTATGCTGATTCACTCTTTTT |
| --- | --- | --- |
| SEQ ID NO: 129 | Imager Calibration (High) | TTTTCTATGTATCGATGTTGAGAAATTTTTTT |
| SEQ ID NO: 130 | Imager Calibration (Low) | TTTTCTAGATACTTGTGTAAGTGAATTTTTTT |
| SEQ ID NO: 131 | Imager Calibration (Medium) | TTTTTCTAAGTCATGTTGTTGAAGAATTTTTTT |
| SEQ ID NO: 126 | *Cannabis* ITS1 DNA Control 1 | TTTTTTAATCTGCGCCAAGGAACAATATTTTTTT |
| SEQ ID NO: 127 | *Cannabis* ITS1 DNA Control 2 | TTTTTGCAATCTGCGCCAAGGAACAATATTTTTT |
| SEQ ID NO: 128 | *Cannabis* ITS1 DNA Control 3 | TTTATTTCTTGCGCCAAGGAACAATATTTTATTT |
| SEQ ID NO: 86 | Total Yeast and Mold (High sensitivity) | TTTTTTTTGAATCATCGARTCTTTGAACGCATTTTTTT |
| SEQ ID NO: 87 | Total Yeast and Mold (Low sensitivity) | TTTTTTTTGAATCATCGARTCTCCTTTTTTT |
| SEQ ID NO: 88 | Total Yeast and Mold (Medium sensitivity) | TTTTTTTTGAATCATCGARTCTTTGAACGTTTTTTT |
| SEQ ID NO: 132 | Negative control | TTTTTTCTACTACCTATGCTGATTCACTCTTTTT |
| SEQ ID NO: 92 | *Aspergillus fumigatus* 1 | TTTCTTTTCGACACCCAACTTTATTTCCTTATTT |
| SEQ ID NO: 90 | *Aspergillus flavus* 1 | TTTTTTCGCAAATCAATCTTTTTCCAGTCTTTTT |
| SEQ ID NO: 95 | *Aspergillus niger* 1 | TTTTTTCGACGTTTTCCAACCATTTCTTTT |
| SEQ ID NO: 100 | *Botrytis* spp. | TTTTTTTCATCTCTCGTTACAGGTTCTCGGTTCTTTTTTT |
| SEQ ID NO: 108 | *Fusarium* spp. | TTTTTTTTAACACCTCGCRACTGGAGATTTTTTT |
| SEQ ID NO: 89 | *Alternaria* spp | TTTTTTCAAGGTCTAGCATCCATTAAGTTTTTT |
| SEQ ID NO: 123 | *Rhodoturula* spp. | TTTTTTCTCGTTCGTAATGCATTAGCACTTTTTT |
| SEQ ID NO: 117 | *Penicillium paxilli* | TTTTTTCCCCTCAATCTTTAACCAGGCCTTTTT |
| SEQ ID NO: 116 | *Penicillium oxalicum* | TTTTTTACACCATCAATCTTAACCAGGCCTTTTT |
| SEQ ID NO: 118 | *Penicillium* spp. | TTTTTTCAACCCAAATTTTTATCCAGGCCTTTTT |
| SEQ ID NO: 102 | *Candida* spp. Group 1 | TTTTTTTGTTTGGTGTTGAGCRATACGTATTTTT |
| SEQ ID NO: 103 | *Candida* spp. Group 2 | TTTTACTGTTTGGTAATGAGTGATACTCTCATTTT |
| SEQ ID NO: 124 | *Stachybotrys* spp | TTTCTTCTGCATCGGAGCTCAGCGCGTTTTATTT |
| SEQ ID NO: 125 | *Trichoderma* spp. | TTTTTCCTCCTGCGCAGTAGTTTGCACATCTTTT |
| SEQ ID NO: 105 | *Cladosporium* spp. | TTTTTTTTGTGGAAACTATTCGCTAAAGTTTTTT |
| SEQ ID NO: 121 | *Podosphaera* spp. | TTTTTTTTAGTCAYGTATCTCGCGACAGTTTTTT |
| SEQ ID NO: 132 | Negative control | TTTTTTCTACTACCTATGCTGATTCACTCTTTTT |
| SEQ ID NO: 37 | Total Aerobic bacteria (High) | TTTTTTTTTCCTACGGGAGGCAGTTTTTTT |
| SEQ ID NO: 38 | Total Aerobic bacteria (Medium) | TTTTTTTTCCCTACGGGAGGCATTTTTTTT |
| SEQ ID NO: 39 | Total Aerobic bacteria (Low) | TTTATTTTCCCTACGGGAGGCTTTTATTTT |
| SEQ ID NO: 47 | Bile-tolerant Gram-negative (High) | TTTTTCTATGCAGTCATGCTGTGTGTRTGTCTTTTT |

TABLE 4-continued

Nucleic acid probes Linked to the
Microarray Surface via the Present Invention

| SEQ ID NO: 48 | Bile-tolerant Gram-negative (Medium) | TTTTTCTATGCAGCCATGCTGTGTGTRTTTTTTT |
| --- | --- | --- |
| SEQ ID NO: 49 | Bile-tolerant Gram-negative (Low) | TTTTTCTATGCAGTCATGCTGCGTGTRTTTTTTT |
| SEQ ID NO: 53 | Coliform/Enterobacteriaceae | TTTTTTCTATTGACGTTACCCGCTTTTTTT |
| SEQ ID NO: 81 | stx1 gene | TTTTTTCTTTCCAGGTACAACAGCTTTTTT |
| SEQ ID NO: 82 | stx2 gene | TTTTTTGCACTGTCTGAAACTGCCTTTTTT |
| SEQ ID NO: 59 | etuf gene | TTTTTTCCATCAAAGTTGGTGAAGAATCTTTTTT |
| SEQ ID NO: 132 | Negative control | TTTTTTCTACTACCTATGCTGATTCACTCTTTTT |
| SEQ ID NO: 65 | Listeria spp. | TTTTCTAAGTACTGTTGTTAGAGAATTTTT |
| SEQ ID NO: 56 | Aeromonas spp. | TTATTTTCTGTGACGTTACTCGCTTTTATT |
| SEQ ID NO: 78 | Staphylococcus aureus 1 | TTTATTTTCATATGTGTAAGTAACTGTTTTATTT |
| SEQ ID NO: 49 | Campylobacter spp. | TTTTTTATGACACTTTTCGGAGCTCTTTTT |
| SEQ ID NO: 72 | Pseudomonas spp. 3 | TTTATTTTAAGCACTTTAAGTTGGGATTTTATTT |
| SEQ ID NO: 53 | Clostridium spp. | TTTTCTGGAMGATAATGACGGTACAGTTTT |
| SEQ ID NO: 42 | Escherichia coli/Shigella 1 | TTTTCTAATACCTTTGCTCATTGACTCTTT |
| SEQ ID NO: 74 | Salmonella enterica/Enterobacter 1 | TTTTTTTGTTGTGGTTAATAACCGATTTTT |
| SEQ ID NO: 61 | invA gene | TTTTTTTATTGATGCCGATTTGAAGGCCTTTTTT |

The set of 48 different probes of Table 4 were formulated as described in Table 3, then printed onto epoxysilane coated borosilicate glass, using an Gentics Q-Array mini contact printer with Arrayit SMP pins, which deposit about 1 nL of formulation per spot. As described in FIG. 1, the arrays thus printed were then allowed to react with the epoxisilane surface at room temperature, and then evaporate to remove free water, also at room temperature. Upon completion of the evaporation step (typically overnight) the air-dried microarrays were then UV treated in a STATOLINKERa UV irradiation system: 300 mjoules of irradiation at 254 nm to initiate thymidine-mediated crosslinking. The microarrays are then ready for use, with no additional need for washing or capping.

Example 2

Using the 3-Dimensional Lattice Microarray System for DNA Analysis
Sample Processing
Harvesting Pathogens from plant surface comprises the following steps:
1. Wash the plant sample or tape pull in 1× phosphate buffered saline (PBS)
2. Remove plant material/tape
3. Centrifuge to pellet cells & discard supernatant
4. Resuspend in PathogenDx® Sample Prep Buffer premixed with Sample Digestion Buffer
5. Heat at 55° C. for 45 minutes
6. Vortex to dissipate the pellet
7. Heat at 95° C. for 15 minutes
8. Vortex and centrifuge briefly before use in PCR
Amplification by PCR
The sample used for amplification and hybridization analysis was a Cannabis flower wash from a licensed Cannabis lab. The washed flower material was then pelleted by centrifugation. The pellet was then digested with proteinaseK, then spiked with a known amount of Salmonella DNA before PCR amplification.

TABLE 5

PCR Primers and PCR
conditions used in amplification

PCR primers (P1) for PCR Reaction #1
Cannabis ITS1 1° FP*-TTTGCAACAGCAGAACGACCCGTGA Cannabis ITS1 1° RP*-TTTCGATAAACACGCATCTCGATTG Enterobacteriaceae 16S 1° FP-TTACCTTCGGGCCTCTTG
CCATCRGATGTG Enterobacteriaceae 16S 1° RP-TTGGAATTCTACCCCCCT
CTACRAGACTCAAGC PCR primers (P2) for PCR Reaction #2
Cannabis ITS1 2° FP-TTTCGTGAACACGTTTTAAACAGCTTG Cannabis ITS1 2° RP-(Cy3)TTTTCCACCGCACGAGCCACGC
GAT Enterobacteriaceae 16S 2° FP-TTATATTGCACAATGGGC
GCAAGCCTGATG TABLE 5-continued PCR Primers and PCR conditions used in amplification Enterobacteriaceae 16S 2° RP-(Cy3)TTTTGTATTACCG
CGGCTGCTGGCA

| | PCR Reagent | |
|---|---|---|
| | Primary PCR Concentration 1X | Secondary PCR PCR Buffer Concentration 1X |
| MgCl$_2$ | 2.5 mM | 2.5 mM |
| BSA | 0.16 mg/mL | 0.16 mg/mL |
| dNTP's | 200 mM | 200 mM |
| Primer mix | 200 nM each | 50 nM-FP/ 200 nM RP |
| Taq Polymerase | 1.5 Units | 1.5 Units |

| Program for PCR Reaction #1 | | | | |
|---|---|---|---|---|
| 95° C, 4 min | 98° C, 30 s | 61° C, 30 s 25X | 72° C, 60 s | 72° C, 7 min |

| Program for PCR Reaction #2 | | | | |
|---|---|---|---|---|
| 95° C, 4 min | 98° C, 20 s | 61° C, 20 s 25X | 72° C, 30 s | 72° C, 7 min |

*FP, Forward Primer; *RP, Reverse Primer

The *Salmonella* DNA spiked sample was then amplified with PCR primers (P1-Table 5) specific for the 16S region of Enterobacteriaceae in a tandem PCR reaction to first isolate the targeted region (PCR Reaction #1) and also PCR primers (P1-Table 5) which amplify a segment of *Cannabis* DNA (ITS) used as a positive control.

The product of PCR Reaction #1 (1 μL) was then subjected to a second PCR reaction (PCR Reaction #2) which additionally amplified and labelled the two targeted regions (16S, ITS) with green CY3 fluorophore labeled primers (P2-Table 5). The product of the PCR Reaction #2 (50 μL) was then diluted 1-1 with hybridization buffer (4×SSC+5× Denhardt's solution) and then applied directly to the microarray for hybridization.

Hybridization

Because the prior art method of microarray manufacture allows DNA to be analyzed via hybridization without the need for pre-treatment of the microarray surface, the use of the microarray is simple, and involves 6 manual or automated pipetting steps.

1) Pipette the amplified DNA+binding buffer onto the microarray
2) Incubate for 30 minutes to allow DNA binding to the microarray (typically at room temperature, RT)
3) Remove the DNA+binding buffer by pipetting
4) Pipette 50 uL of wash buffer onto the microarray (0.4×SSC+0.5×Denhardt's) and incubate 5 min at RT.
5) Remove the wash buffer by pipetting
6) Repeat steps 4&5
7) Perform image analysis at 532 nm and 635 nm to detect the probe spot location (532 nm) and PCR product hybridization (635 nm).

Image Analysis

Image Analysis was performed at two wavelengths (532 nm and 635 nm) on a raster-based confocal scanner GenePix 4000B Microarray Scanner, with the following imaging conditions: 33% Laser power, 400PMT setting at 532 nm/33% Laser Power, 700PMT setting at 635 nm. FIG. 3 shows an example of the structure and hybridization performance of the microarray.

Figure 3A:
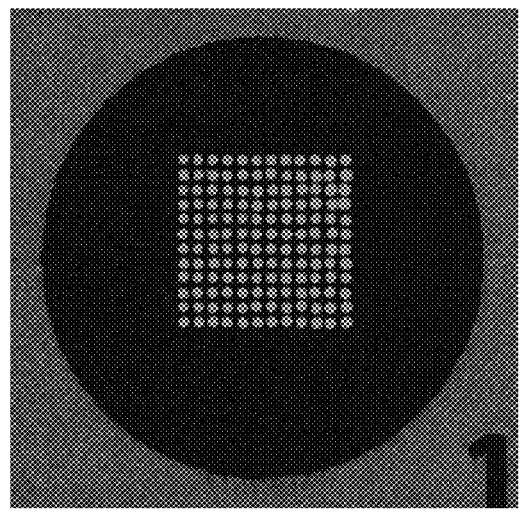
FIGS. 3A-3C show experimental data using the covalent microarray system. In this example of the invention the bifunctional polymeric linker was a chemically modified 40 base long oligo deoxythymidine (OligodT) having a Cy5 fluorescent dye attached at its 5' terminus and an amino group attached at its 3' terminus, suitable for covalent linkage with a borosilicate glass solid support which had been chemically activated on its surface with epoxysilane. The nucleic acid probes comprised unmodified DNA oligonucleotides, suitable to bind to the solution state target, each oligonucleotide terminated with about 5 to 7 thymidines, to allow for photochemical crosslinking with the thymidines in the top domain of the polymeric (oligodT) linker.

FIG. 3A reveals imaging of the representative microarray, described above, after hybridization and washing, as visualized at 635 nm. The 635 nm image is derived from signals from the (red) CY5 fluor attached to the 5' terminus of the bifunctional polymer linker OligodT which had been introduced during microarray fabrication as a positional marker in each microarray spot (see FIG. 1 and Table 3). The data in FIG. 3A confirm that the Cy5-labelled OligodT has been permanently linked to the microarray surface, via the combined activity of the bi-functional linker and subsequent UV-crosslinking, as described in FIG. 1.

Figure 3B:
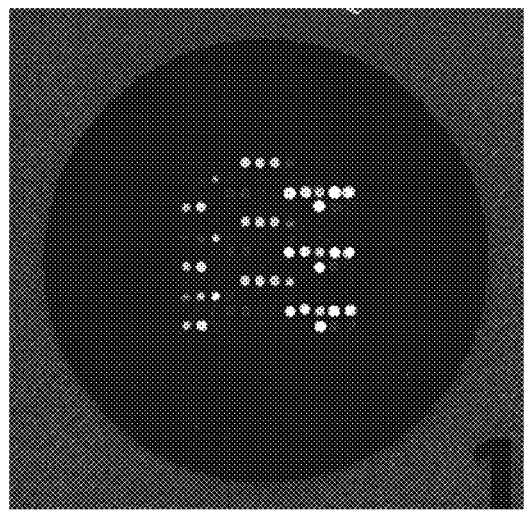

FIG. 3B reveals imaging of the representative microarray described above after hybridization and washing as visualized at 532 nm. The 532 nm image is derived from signals from the (green) CY3 fluor attached to the 5' terminus of PCR amplified DNA obtained during PCR Reaction #2. It is clear from FIG. 3B that only a small subset of the 48 discrete probes bind to the Cy3-labelled PCR product, thus confirming that the present method of linking nucleic acid probes to form a microarray (FIG. 1) yields a microarray product capable of sequence specific binding to a (cognate) solution state target. The data in FIG. 3B reveal the underlying 3-fold repeat of the data (i.e., the array is the same set of 48 probes printed three times as 3 distinct sub-arrays to form the final 48×3=144 element microarray. The observation that the same set of 48 probes can be printed 3-times, as three repeated sub-domains show that the present invention generates microarray product that is reproducible.

Figure 3C:
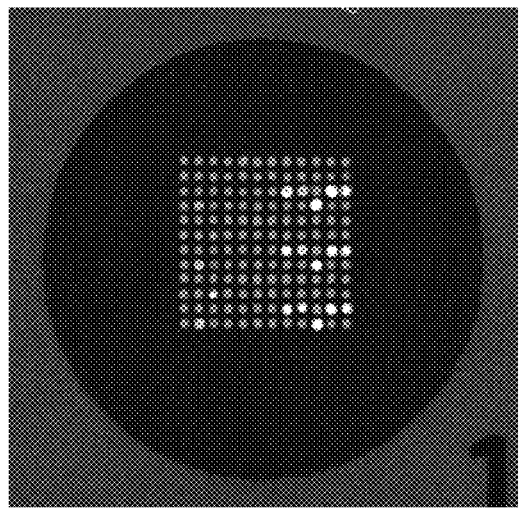

FIG. 3C reveals imaging of the representative microarray, described above, after hybridization and washing, as visualized with both the 532 nm and 635 nm images superimposed. The superimposed images display the utility of parallel attachment of a Cy5-labelled OligodT positional marker relative to the sequence specific binding of the CY3-labelled PCR product.

Example 3

Figure 4A:
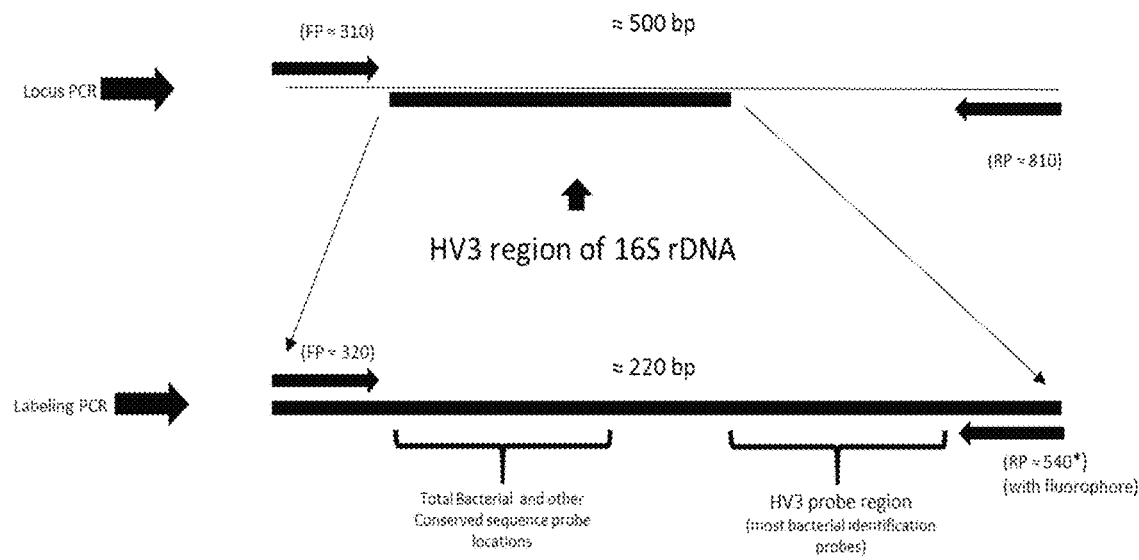
FIG. 4A is a graphical representation of the position of PCR primers employed within the 16S locus (all bacteria) to be used to PCR amplify unpurified bacterial contamination obtained from *Cannabis* wash and related plant wash. These PCR primers are used to amplify and dye label DNA from such samples for bacterial analysis via microarray hybridization.

FIG. 4A shows an exemplar of the first PCR step. As is standard, such PCR reactions are initiated by the administration of PCR Primers. Primers define the start and stopping point of the PCR based DNA amplification reaction. In this embodiment, a pair of PCR reactions is utilized to support the needed DNA amplification. In general, such PCR amplification is performed in series: a first pair of PCRs, with the suffix "P1" in FIG. 4A are used to amplify about 1 μL of any unpurified DNA sample, such as a raw *Cannabis* leaf wash for example. About 1 μL of the product of that first PCR reaction is used as the substrate for a second PCR reaction that is used to affix a fluorescent dye label to the DNA, so that the label may be used to detect the PCR product when it binds by hybridization to the microarray. The primer sequences for the first and second PCRs are shown in Table 6. The role of this two-step reaction is to avert the need to purify the pathogen DNA to be analyzed. The first PCR reaction, with primers "P1" is optimized to accommodate the raw starting material, while the second PCR primer pairs "P2" are optimized to obtain maximal DNA yield, plus dye labeling from the product of the first reaction. Taken in the aggregate, the sum of the two reactions obviates the need to either purify or characterize the pathogen DNA of interest.

FIG. 4A reveals at low resolution the 16S rDNA region which is amplified in an embodiment, to isolate and amplify a region which may be subsequently interrogated by hybridization. The DNA sequence of this 16S rDNA region is known to vary greatly among different bacterial species. Consequently, having amplified this region by two step PCR, that sequence variation may be interrogated by the subsequent microarray hybridization step.

TABLE 6

First and Second PCR Primers

| SEQ ID NO. | Primer target | Primer sequence |
|---|---|---|
| First PCR Primers (P1) for the first amplification step | | |
| SEQ ID NO: 1 | 16S rDNA HV3 Locus (Bacteria) | TTTCACAYTGGRACTGAGACACG |
| SEQ ID NO: 2 | 16S rDNA HV3 Locus (Bacteria) | TTTGACTACCAGGGTATCTAATCCTGT |
| SEQ ID NO: 3 | Stx1 Locus (Pathogenic E. coli) | TTTATAATCTACGGCTTATTGTTGAACG |
| SEQ ID NO: 4 | Stx1 Locus (Pathogenic E. coli) | TTTGGTATAGCTACTGTCACCAGACAATG |
| SEQ ID NO: 5 | Stx2 Locus (Pathogenic E. coli) | TTTGATGCATCCAGAGCAGTTCTGCG |
| SEQ ID NO: 6 | Stx2 Locus (Pathogenic E. coli) | TTTGTGAGGTCCACGTCTCCCGGCGTC |
| SEQ ID NO: 7 | InvA Locus (*Salmonella*) | TTTATTATCGCCACGTTCGGGCAATTCG |
| SEQ ID NO: 8 | InvA Locus (*Salmonella*) | TTTCTTCATCGCACCGTCAAAGGAACCG |
| SEQ ID NO: 9 | tuf Locus (All E. coli) | TTTCAGAGTGGGAAGCGAAAATCCTG |
| SEQ ID NO: 10 | tuf Locus (All E. coli) | TTTACGCCAGTACAGGTAGACTTCTG |
| SEQ ID NO: 11 | 16S rDNA *Enterobacteriaceae* HV3 Locus | TTACCTTCGGGCCTCTTGCCATCRGATGTG |
| SEQ ID NO: 12 | 16S rDNA *Enterobacteriaceae* HV3 Locus | TTGGAATTCTACCCCCCTCTACRAGACTCAAGC |
| SEQ ID NO: 13 | ITS2 Locus (All Yeast, Mold/Fungus) | TTTACTTTYAACAAYGGATCTCTTGG |
| SEQ ID NO: 14 | ITS2 Locus (All Yeast, Mold/Fungus) | TTTCTTTTCCTCCGCTTATTGATATG |
| SEQ ID NO: 15 | ITS2 Locus (*Aspergillus* species) | TTTAAAGGCAGCGGCGGCACCGCGTCCG |
| SEQ ID NO: 16 | ITS2 Locus (*Aspergillus* species) | TTTTCTTTTCCTCCGCTTATTGATATG |
| SEQ ID NO: 17 | ITS1 Locus (*Cannabis*/Plant) | TTTGCAACAGCAGAACGACCCGTGA |
| SEQ ID NO: 18 | ITS1 Locus (*Cannabis*/Plant) | TTTCGATAAACACGCATCTCGATTG |
| Second PCR Primers (P2) for the second labeling amplification step | | |
| SEQ ID NO: 19 | 16S rDNA HV3 Locus (All Bacteria) | TTTACTGAGACACGGYCCARACTC |
| SEQ ID NO: 20 | 16S rDNA HV3 Locus (All Bacteria) | TTTGTATTACCGCGGCTGCTGGCA |
| SEQ ID NO: 21 | Stx1 Locus (Pathogenic E. coli) | TTTATGTGACAGGATTTGTTAACAGGAC |
| SEQ ID NO: 22 | Stx1 Locus (Pathogenic E. coli) | TTTCTGTCACCAGACAATGTAACCGCTG |
| SEQ ID NO: 23 | Stx2 Locus (Pathogenic E. coli) | TTTTGTCACTGTCACAGCAGAAG |

TABLE 6-continued

First and Second PCR Primers

| SEQ ID NO. | Primer target | Primer sequence |
|---|---|---|
| SEQ ID NO: 24 | Stx2 Locus (Pathogenic E. coli) | TTTGCGTCATCGTATACACAGGAGC |
| SEQ ID NO: 25 | InvA Locus (All *Salmonella*) | TTTTATCGTTATTACCAAAGGTTCAG |
| SEQ ID NO: 26 | InvA Locus (All *Salmonella*) | TTTCCTTTCCAGTACGCTTCGCCGTTCG |
| SEQ ID NO: 27 | tuf Locus (All *E. coli*) | TTTGTTGTTACCGGTCGTGTAGAAC |
| SEQ ID NO: 28 | tuf Locus (All *E. coli*) | TTTCTTCTGAGTCTCTTTGATACCAACG |
| SEQ ID NO: 29 | 16S rDNA *Enterobacteriaceae* HV3 Locus | TTATATTGCACAATGGGCGCAAGCCTGATG |
| SEQ ID NO: 30 | 16S rDNA *Enterobacteriaceae* HV3 Locus | TTTTGTATTACCGCGGCTGCTGGCA |
| SEQ ID NO: 31 | ITS2 Locus (All Yeast, Mold/Fungus) | TTTGCATCGATGAAGARCGYAGC |
| SEQ ID NO: 32 | ITS2 Locus (All Yeast, Mold/Fungus) | TTTCCTCCGCTTATTGATATGC |
| SEQ ID NO: 33 | ITS2 Locus (*Aspergillus* species) | TTTCCTCGAGCGTATGGGCTTTGTC |
| SEQ ID NO: 34 | ITS2 Locus (*Aspergillus* species) | TITTTCCTCCGCTTATIGATATGC |
| SEQ ID NO: 35 | ITS1 Locus (*Cannabis*/Plant) | TTTCGTGAACACGTTTTAAACAGCTTG |
| SEQ ID NO: 36 | ITS1 Locus (*Cannabis*/Plant) | TTTCCACCGCACGAGCCACGCGAT |

Figure 4B:
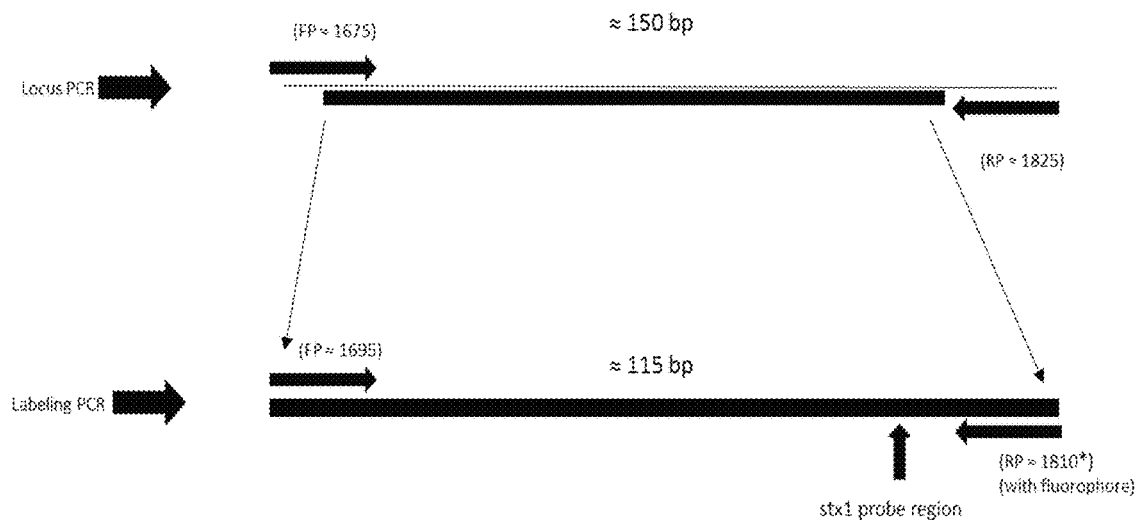
FIG. 4B is a graphical representation of the position of PCR primers employed within the stx1 locus (pathogenic *E. coli*) to be used to PCR amplify unpurified bacterial contamination obtained from *Cannabis* wash and related plant wash. These PCR primers are used to amplify and dye label DNA from such samples for bacterial analysis via microarray hybridization.

FIG. 4B displays the stx1 gene locus which is present in the most important pathogenic strains of *E coli* and which encodes Shigatoxin 1. Employing the same two-step PCR approach, a set of two PCR primer pairs were designed which, in tandem, can be used to amplify and label unprocessed bacterial samples to present the stx1 locus for analysis by microarray-based DNA hybridization.

Figure 5A:
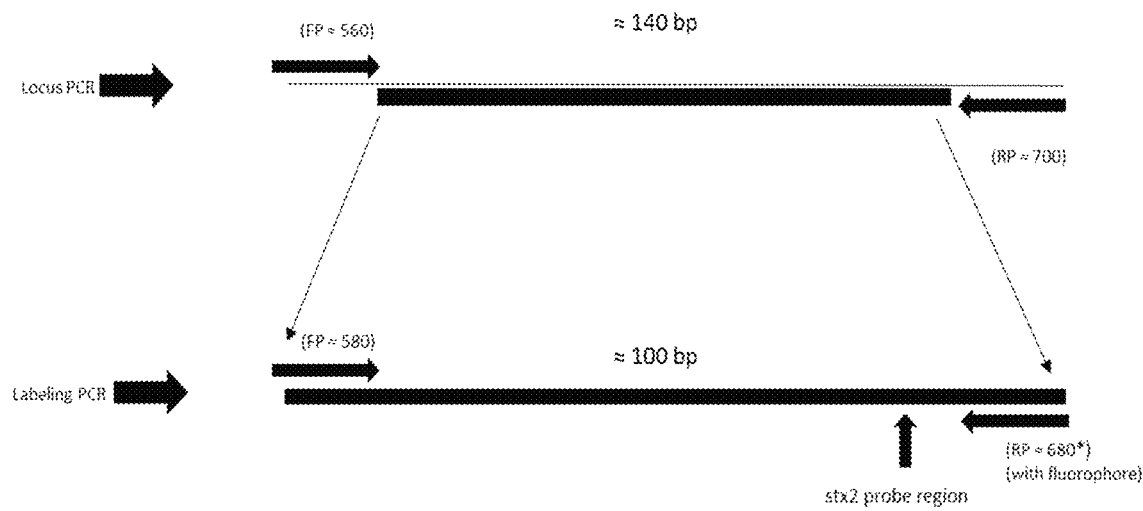
FIG. 5A is a graphical representation of the position of PCR primers employed as a two stage PCR reaction within the stx2 locus (pathogenic *E. coli*) to be used to PCR amplify unpurified bacterial contamination obtained from *Cannabis* wash and related plant wash. These PCR primers are used to amplify and dye label DNA from such samples for bacterial analysis via microarray hybridization.

FIG. 5A displays the stx2 gene locus which is also present in the most important pathogenic strains of *E coli* and which encodes Shigatoxin 2. Employing the same two-step PCR approach, a set of two PCR primer pairs were designed which, in tandem, can be used to amplify and label unprocessed bacterial samples so as to present the stx2 locus for analysis by microarray-based DNA hybridization.

Figure 5B:
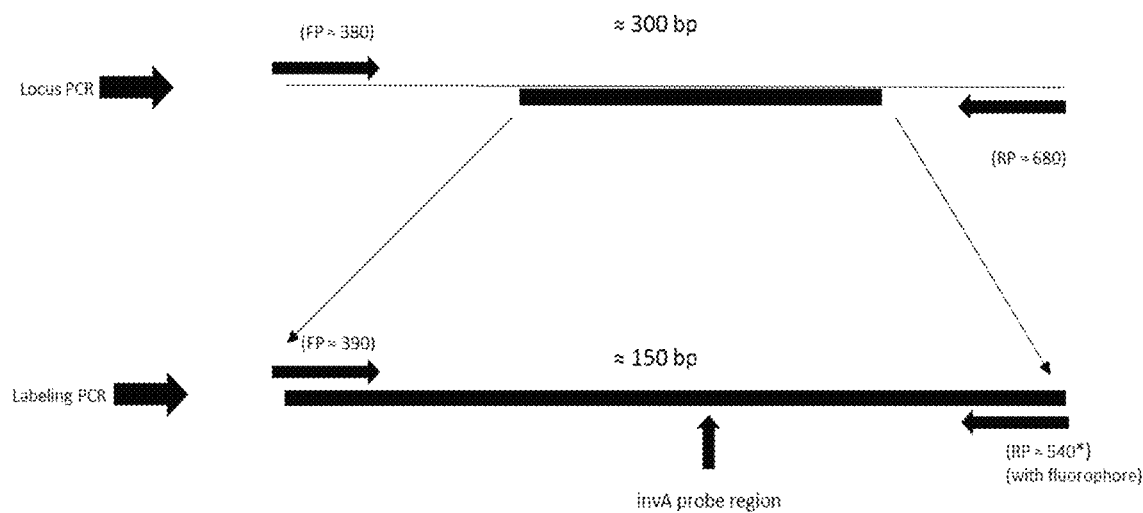
FIG. 5B is a graphical representation of the position of PCR primers employed within the invA locus (*Salmonella*) to be used to PCR amplify unpurified bacterial contamination obtained from *Cannabis* wash and related plant wash. These PCR primers are used to amplify and dye label DNA from such samples for bacterial analysis via microarray hybridization.

FIG. 5B displays the invA gene locus which is present in all strains of *Salmonella* and which encodes the InvAsion A gene product. Employing the same two-step PCR approach, a set of two PCR primer pairs were designed which, in tandem, can be used to amplify and label unprocessed bacterial samples so as to present the invA locus for analysis by microarray-based DNA hybridization.

Figure 6:
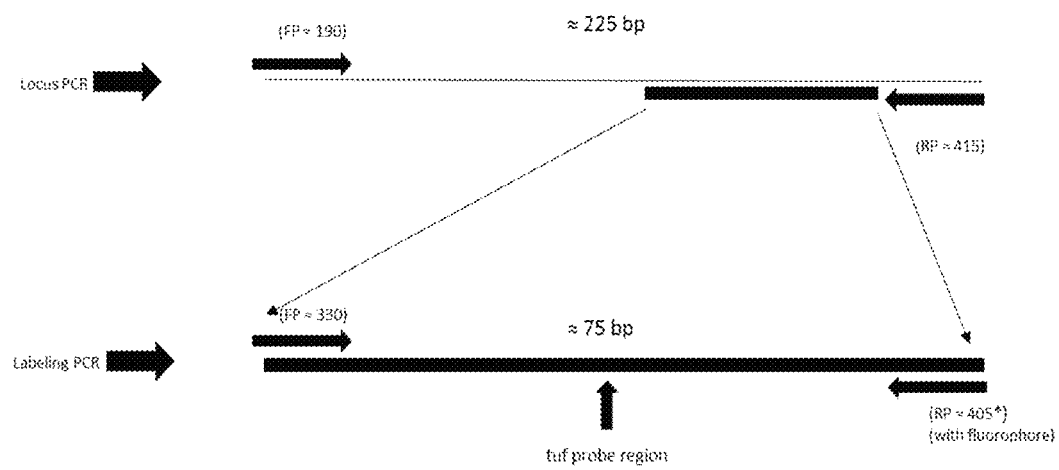
FIG. 6 is a graphical representation of the position of PCR primers employed within the tuf locus (*E. coli*) to be used to PCR amplify unpurified bacterial contamination obtained from *Cannabis* wash and related plant wash. These PCR primers are used to amplify and dye label DNA from such samples for bacterial analysis via microarray hybridization.

FIG. 6 displays the tuf gene locus which is present in all strains of *E coli* and which encodes the ribosomal elongation factor Tu. Employing the same two-step PCR approach, a set of two PCR primer pairs were designed which, in tandem, can be used to amplify and label unprocessed bacterial samples so as to present the tuf locus for analysis by microarray-based DNA hybridization.

Figure 7:
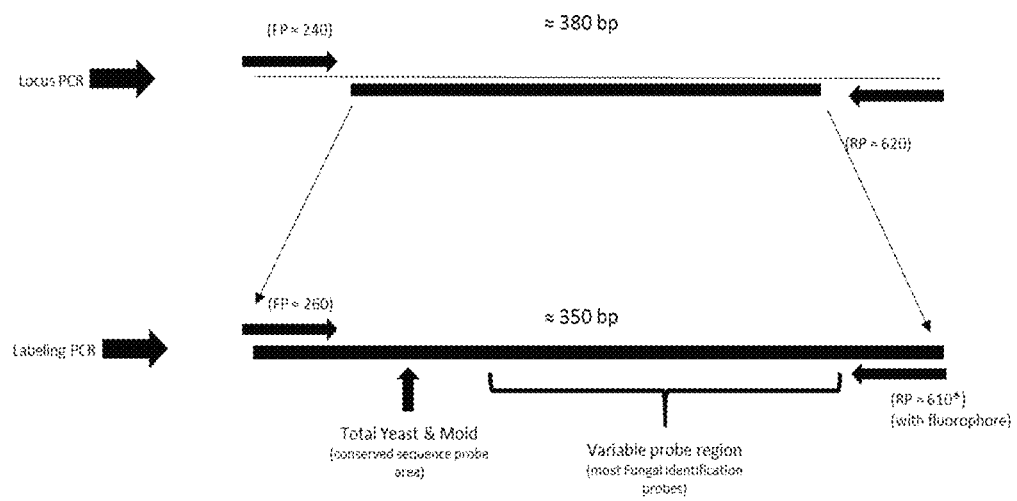
FIG. 7 is a graphical representation of the position of PCR primers employed within the ITS2 locus (yeast and mold) to be used to PCR amplify unpurified yeast, mold and fungal contamination obtained from *Cannabis* wash and related plant wash. These PCR primers are used to amplify and dye label DNA from such samples for yeast and mold analysis via microarray hybridization.

FIG. 7 displays the ITS2 locus which is present in all eukaryotes, including all strains of yeast and mold and which encodes the intergenic region between ribosomal genes 5.8S and 28S. ITS2 is highly variable in sequence and that sequence variation can be used to resolve strain differences in yeast, and mold. Employing the same two-step PCR approach, a set of two PCR primer pairs were designed which, in tandem, can be used to amplify and label unprocessed yeast and mold samples so as to present the ITS2 locus for analysis by microarray-based DNA hybridization.

Figure 8:
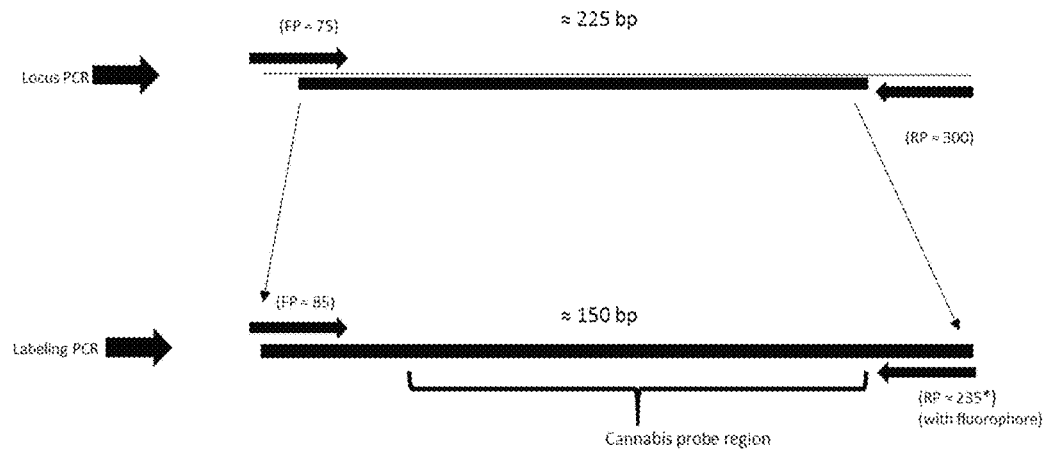
FIG. 8 is a graphical representation of the position of PCR primers employed within the ITS1 locus (*Cannabis* Plant Control) to be used to PCR amplify unpurified DNA obtained from *Cannabis* wash. These PCR primers are used to amplify and dye label DNA from such samples for DNA analysis via microarray hybridization. This PCR reaction is used to generate an internal plant host control signal, via hybridization, to be used to normalize bacterial, yeast, mold and fungal signals obtained by microarray analysis on the same microarray.

FIG. 8 displays the ITS1 gene locus which is present in all eukaryotes, including all plants and animals, which encodes the intergenic region between ribosomal genes 18S and 5.8S. ITS1 is highly variable in sequence among higher plants and that sequence variation can be used to identify plant species. Employing the same two-step PCR approach, a set of two PCR primer pairs were designed which, in tandem, can be used to amplify and label unprocessed *Cannabis* samples so as to present the ITS1 locus for analysis by microarray-based DNA hybridization. The identification and quantitation of the *Cannabis* sequence variant of ITS1 is used as an internal normalization standard in the analysis of pathogens recovered from the same *Cannabis* samples.

Table 7 displays representative oligonucleotide sequences which are used as microarray probes in an embodiment for DNA microarray-based analysis of bacterial 16S locus as described in FIG. 4. The sequence of those probes has been varied to accommodate the cognate sequence variation which occurs as a function of species difference among bacteria. In all cases, the probe sequences are terminated with a string of T's at each end, to enhance the efficiency of probe attachment to the microarray surface, at time of microarray manufacture. Table 8 shows sequences of the Calibration and Negative controls used in the microarray.

Table 9 displays representative oligonucleotide sequences which are used as microarray probes in an embodiment for DNA microarray-based analysis of eukaryotic pathogens (fungi, yeast & mold) based on their ITS2 locus as described in FIG. 7. Sequences shown in Table 8 are used as controls. The sequence of those probes has been varied to accommodate the cognate sequence variation which occurs as a function of species difference among fungi, yeast & mold. In all cases, the probe sequences are terminated with a string of T's at each end, to enhance the efficiency of probe attachment to the microarray surface, at time of microarray manufacture.

Table 10 displays representative oligonucleotide sequences which are used as microarray probes in an embodiment for DNA microarray-based analysis of *Cannabis* at the ITS1 locus (*Cannabis* spp.).

TABLE 7

| | Oligonucleotide probe sequence for the 16S Locus | |
|---|---|---|
| SEQ ID NO: 37 | Total Aerobic bacteria (High) | TTTTTTTTTCCTACGGGAGGCAGTTTTTTT |
| SEQ ID NO: 38 | Total Aerobic bacteria (Medium) | TTTTTTTTCCCTACGGGAGGCATTTTTTTT |
| SEQ ID NO: 39 | Total Aerobic bacteria (Low) | TTTATTTTCCCTACGGAGGCTTTTATTTT |
| SEQ ID NO: 40 | *Enterobacteriaceae* (Low sensitivity) | TTTATTCTATTGACGTTACCCATTTATTTT |
| SEQ ID NO: 41 | *Enterobacteriaceae* (Medium sensitivity) | TTTTTTCTATTGACGTTACCCGTTTTTTTT |
| SEQ ID NO: 42 | *Escherichia coli/Shigella* 1 | TTTTCTAATACCTTTGCTCATTGACTCTTT |
| SEQ ID NO: 43 | *Escherichia coli/Shigella* 2 | TTTTTTAAGGGAGTAAAGTTAATATTTTTT |
| SEQ ID NO: 44 | *Escherichia coli/Shigella* 3 | TTTTCTCCTTTGCTCATTGACGTTATTTTT |
| SEQ ID NO: 45 | *Bacillus* spp. Group1 | TTTTTCAGTTGAATAAGCTGGCACTCTTTT |
| SEQ ID NO: 46 | *Bacillus* spp. Group2 | TTTTTTCAAGTACCGTTCGAATAGTTTTTT |
| SEQ ID NO: 47 | Bile-tolerant Gram-negative (High) | TTTTTCTATGCAGTCATGCTGTGTGTRTGTCTTTTT |
| SEQ ID NO: 48 | Bile-tolerant Gram-negative (Medium) | TTTTTCTATGCAGCCATGCTGTGTGTRTTTTTTT |
| SEQ ID NO: 49 | Bile-tolerant Gram-negative (Low) | TTTTTCTATGCAGTCATGCTGCGTGTRTTTTTTT |
| SEQ ID NO: 50 | *Campylobacter* spp. | TTTTTTATGACACTTTTCGGAGCTCTTTTT |
| SEQ ID NO: 51 | *Chromobacterium* spp. | TTTTATTTTCCCGCTGGTTAATACCCTTTATTTT |
| SEQ ID NO: 52 | *Citrobacter* spp. Group1 | TTTTTTCCTTAGCCATTGACGTTATTTTTT |
| SEQ ID NO: 53 | *Clostridium* spp. | TTTTCTGGAMGATAATGACGGTACAGTTTT |
| SEQ ID NO: 54 | *Coliform/Enterobacteriaceae* | TTTTTTCTATTGACGTTACCCGCTTTTTTT |
| SEQ ID NO: 55 | *Aeromonas salmonicida/hydrophilia* | TTTTTGCCTAATACGTRTCAACTGCTTTTT |
| SEQ ID NO: 56 | *Aeromonas* spp. | TTATTTTCTGTGACGTTACTCGCTTTTATT |
| SEQ ID NO: 57 | *Alkanindiges* spp. | TTTTTAGGCTACTGRTACTAATATCTTTTT |
| SEQ ID NO: 58 | *Bacillus pumilus* | TTTATTTAAGTGCRAGAGTAACTGCTATTTTATT |
| SEQ ID NO: 59 | etuf gene | TTTTTTCCATCAAAGTTGGTGAAGAATCTTTTTT |
| SEQ ID NO: 60 | *Hafnia* spp. | TTTTTTCTAACCGCAGTGATTGATCTTTTT |
| SEQ ID NO: 61 | invA gene | TTTTTTTATTGATGCCGATTTGAAGGCCTTTTTT |
| SEQ ID NO: 62 | *Klebsiella oxytoca* | TTTTTTCTAACCTTATTCATTGATCTTTTT |
| SEQ ID NO: 63 | *Klebsiella pneumoniae* | TTTTTTCTAACCTTGGCGATTGATCTTTTT |
| SEQ ID NO: 64 | *Legionella* spp. | TTATTCTGATAGGTTAAGAGCTGATCTTTATTT |
| SEQ ID NO: 65 | *Listeria* spp. | TTTTCTAAGTACTGTTGTTAGAGAATTTTT |
| SEQ ID NO: 66 | *Panteoa agglomerans* | TTTTTTAACCCTGTCGATTGACGCCTTTTT |

TABLE 7-continued

Oligonucleotide probe sequence for the 16S Locus

| | | |
|---|---|---|
| SEQ ID NO: 67 | *Panteoa stewartii* | TTTTTTAACCTCATCAATTGACGCCTTTTT |
| SEQ ID NO: 68 | *Pseudomonas aeruginosa* | TTTTTGCAGTAAGTTAATACCTTGTCTTTT |
| SEQ ID NO: 69 | *Pseudomonas cannabina* | TTTTTTTACGTATCTGTTTTGACTCTTTTT |
| SEQ ID NO: 70 | *Pseudomonas* spp. 1 | TTTTTTGTTACCRACAGAATAAGCATTTTT |
| SEQ ID NO: 71 | *Pseudomonas* spp. 2 | TTTTTTAAGCACTTTAAGTTGGGATTTTTT |
| SEQ ID NO: 72 | *Pseudomonas* spp. 3 | TTTATTTTAAGCACTTTAAGTTGGGATTTTATTT |
| SEQ ID NO: 73 | *Salmonella bongori* | TTTTTTTAATAACCTTGTTGATTGTTTTTT |
| SEQ ID NO: 74 | *Salmonella enterica/Enterobacter* 1 | TTTTTTTGTTGTGGTTAATAACCGATTTTT |
| SEQ ID NO: 75 | *Salmonella enterica/Enterobacter* 2 | TTTTTTTAACCGCAGCAATTGACTCTTTTT |
| SEQ ID NO: 76 | *Salmonella enterica/Enterobacter* 3 | TTTTTTCTGTTAATAACCGCAGCTTTTTTT |
| SEQ ID NO: 77 | *Serratia* spp. | TTTATTCTGTGAACTTAATACGTTCATTTTTATT |
| SEQ ID NO: 78 | *Staphylococcus aureus* 1 | TTTATTTTCATATGTGTAAGTAACTGTTTTATTT |
| SEQ ID NO: 79 | *Staphylococcus aureus* 2 | TTTTTTCATATGTGTAAGTAACTGTTTTTT |
| SEQ ID NO: 80 | *Streptomyces* spp. | TTTTATTTTAAGAAGCGAGAGTGACTTTATTTT |
| SEQ ID NO: 81 | stx1 gene | TTTTTTCTTTCCAGGTACAACAGCTTTTTT |
| SEQ ID NO: 82 | stx2 gene | TTTTTTGCACTGTCTGAAACTGCCTTTTTT |
| SEQ ID NO: 83 | *Vibrio* spp. | TTTTTTGAAGGTGGTTAAGCTAATTTTTTT |
| SEQ ID NO: 84 | *Xanthamonas* spp. | TTTTTTGTTAATACCCGATTGTTCTTTTTT |
| SEQ ID NO: 85 | *Yersinia pestis* | TTTTTTTGAGTTTAATACGCTCAACTTTTT |

TABLE 8

Calibration and Negative Controls

| | | |
|---|---|---|
| SEQ ID NO: 129 | Imager Calibration (High) | TTTTCTATGTATCGATG TTGAGAAATTTTTTT |
| SEQ ID NO: 130 | Imager Calibration (Low) | TTTTCTAGATACTTGTG TAAGTGAATTTTTTT |
| SEQ ID NO: 131 | Imager Calibration (Medium) | TTTTCTAAGTCATGTTG TTGAAGAATTTTTTT |
| SEQ ID NO: 132 | Negative control | TTTTTTCTACTACCTAT GCTGATTCACTCTTTT |

TABLE 9

Oligonucleotide probe sequence for the ITS2 Locus

| | | |
|---|---|---|
| SEQ ID NO: 86 | Total Yeast and Mold (High sensitivity) | TTTTTTTTGAATCATCGARTCTTTGAACGCATTTTTT |
| SEQ ID NO: 87 | Total Yeast and Mold (Low sensitivity) | TTTTTTTTGAATCATCGARTCTCCTTTTTTT |
| SEQ ID NO: 88 | Total Yeast and Mold (Medium sensitivity) | TTTTTTTTGAATCATCGARTCTTTGAACGTTTTTTT |
| SEQ ID NO: 89 | *Alternaria* spp. | TTTTTTCAAAGGTCTAGCATCCATTAAGTTTTTT |
| SEQ ID NO: 90 | *Aspergillus flavus* 1 | TTTTTTCGCAAATCAATCTTTTTCCAGTCTTTTT |
| SEQ ID NO: 91 | *Aspergillus flavus* 2 | TTTTTTTCTTGCCGAACGCAAATCAATCTTTTTTTTTTT |

TABLE 9-continued

Oligonucleotide probe sequence for the ITS2 Locus

| SEQ ID NO: 92 | *Aspergillus fumigatus* 1 | TTTCTTTTCGACACCCAACTTTATTTCCTTATTT |
| --- | --- | --- |
| SEQ ID NO: 93 | *Aspergillus fumigatus* 2 | TTTTTTTGCCAGCCGACACCCATTCTTTTT |
| SEQ ID NO: 94 | *Aspergillus nidulans* | TTTTTTGGCGTCTCCAACCTTACCCTTTTT |
| SEQ ID NO: 95 | *Aspergillus niger* 1 | TTTTTTCGACGTTTTCCAACCATTTCTTTT |
| SEQ ID NO: 96 | *Aspergillus niger* 2 | TTTTTTTCGACGTTTTCCAACCATTTCTTTTT |
| SEQ ID NO: 97 | *Aspergillus niger* 3 | TTTTTTCGCCGACGTTTTCCAATTTTTTT |
| SEQ ID NO: 98 | *Aspergillus terreus* | TTTTTCGACGCATTTATTTGCAACCCTTTT |
| SEQ ID NO: 99 | *Blumeria* | TTTATTTGCCAAAAMTCCTTAATTGCTCTTTTTT |
| SEQ ID NO: 100 | *Botrytis* spp | TTTTTTTCATCTCTCGTTACAGGTTCTCGGTTCTTTTTTT |
| SEQ ID NO: 101 | *Candida albicans* | TTTTTTTTGAAAGACGGTAGTGGTAAGTTTTTT |
| SEQ ID NO: 102 | *Candida* spp. Group 1 | TTTTTTTGTTTGGTGTTGAGCRATACGTATTTTT |
| SEQ ID NO: 103 | *Candida* spp. Group 2 | TTTTACTGTTTGGTAATGAGTGATACTCTCATTTT |
| SEQ ID NO: 104 | *Chaetomium* spp. | TTTCTTTTGGTTCCGGCCGTTAAACCATTTTTTT |
| SEQ ID NO: 105 | *Cladosporium* spp | TTTTTTTTGTGGAAACTATTCGCTAAAGTTTTTT |
| SEQ ID NO: 106 | *Erysiphe* spp. | TTTCTTTTTACGATTCTCGCGACAGAGTTTTTTT |
| SEQ ID NO: 107 | *Fusarium oxysporum* | TTTTTTTCTCGTTACTGGTAATCGTCGTTTTTTT |
| SEQ ID NO: 108 | *Fusarium* spp | TTTTTTTTAACACCTCGCRACTGGAGATTTTTTT |
| SEQ ID NO: 109 | *Golovinomyces* | TTTTTTCCGCTTGCCAATCAATCCATCTCTTTTT |
| SEQ ID NO: 110 | *Histoplasma capsulatum* | TTTATTTTTGTCGAGTTCCGGTGCCCTTTTATTT |
| SEQ ID NO: 111 | *Isaria* spp. | TTTATTTTTCCGCGGCGACCTCTGCTCTTTATTT |
| SEQ ID NO: 112 | *Monocillium* spp. | TTTCTTTTGAGCGACGACGGGCCCAATTTTCTTT |
| SEQ ID NO: 113 | *Mucor* spp. | TTTTCTCCAVVTGAGYACGCCTGTTTCTTTT |
| SEQ ID NO: 114 | *Myrothecium* spp. | TTTATTTCGGTGGCCATGCCGTTAAATTTTATT |
| SEQ ID NO: 115 | *Oidiodendron* spp. | TTTTTTTGCGTAGTACATCTCTCGCTCATTTTTT |
| SEQ ID NO: 116 | *Penicillium oxalicum* | TTTTTTACACCATCAATCTTAACCAGGCCTTTTT |
| SEQ ID NO: 117 | *Penicillium paxilli* | TTTTTTCCCCTCAATCTTTAACCAGGCCTTTTTT |
| SEQ ID NO: 118 | *Penicillium* spp | TTTTTCAACCCAAATTTTTATCCAGGCCTTTTT |
| SEQ ID NO: 119 | *Phoma/Epicoccum* spp. | TTTTTTTGCAGTACATCTCGCGCTTTGATTTTTT |
| SEQ ID NO: 120 | *Podosphaera* spp | TTTTTTGACCTGCCAAAACCCACATACCATTTTT |
| SEQ ID NO: 121 | *Podosphaera* spp. | TTTTTTTTAGTCAYGTATCTCGCGACAGTTTTTT |
| SEQ ID NO: 122 | *Pythium oligandrum* | TTTTATTTAAAGGAGACAACACCAATTTTTATTT |
| SEQ ID NO: 123 | *Rhodoturula* spp | TTTTTTCTCGTTCGTAATGCATTAGCACTTTTTT |
| SEQ ID NO: 124 | *Stachybotrys* spp | TTTCTTCTGCATCGGAGCTCAGCGCGTTTTATTT |
| SEQ ID NO: 125 | *Trichoderma* spp | TTTTTCCTCCTGCGCAGTAGTTTGCACATCTTTT |

Table 11 displays representative oligonucleotide sequences which are used as microarray probes in an embodiment for DNA microarray-based analysis of bacterial pathogens (stx1, stx2, invA, tuf) and for DNA analysis of the presence host *Cannabis* at the ITS1 locus (*Cannabis* spp.). It should be noted that this same approach, with modifications to the ITS1 sequence, could be used to analyze the presence of other plant hosts in such extracts.

TABLE 10

Oligonucleotide probe sequence for the Cannabis ITS1 Locus

| | | |
|---|---|---|
| SEQ ID NO: 126 | *Cannabis* ITS1 DNA Control 1 | TTTTTTAATCTGCGCCA AGGAACAATATTTTTT |
| SEQ ID NO: 127 | *Cannabis* ITS1 DNA Control 2 | TTTTTGCAATCTGCGCC AAGGAACAATATTTTTT |
| SEQ ID NO: 128 | *Cannabis* ITS1 DNA Control 3 | TTTATTTCTTGCGCCAA GGAACAATATTTTATTT |

TABLE 11

Representative Microarray Probe Design for the Present Invention: Bacterial Toxins, ITS1 (*Cannabis*)

| | | |
|---|---|---|
| SEQ ID NO: 81 | stx1 gene | TTTTTTCTTTCCAGGTA CAACAGCTTTTTT |
| SEQ ID NO: 82 | stx2 gene | TTTTTTGCACTGTCTGA AACTGCCTTTTTT |
| SEQ ID NO: 59 | etuf gene | TTTTTTCCATCAAAGTT GGTGAAGAATCTTTTTT |
| SEQ ID NO: 61 | invA gene | TTTTTTTATTGATGCCG ATTTGAAGGCCTTTTTT |
| SEQ ID NO: 126 | *Cannabis* ITS1 DNA Control 1 | TTTTTTAATCTGCGCCA AGGAACAATATTTTTT |

Figure 9:
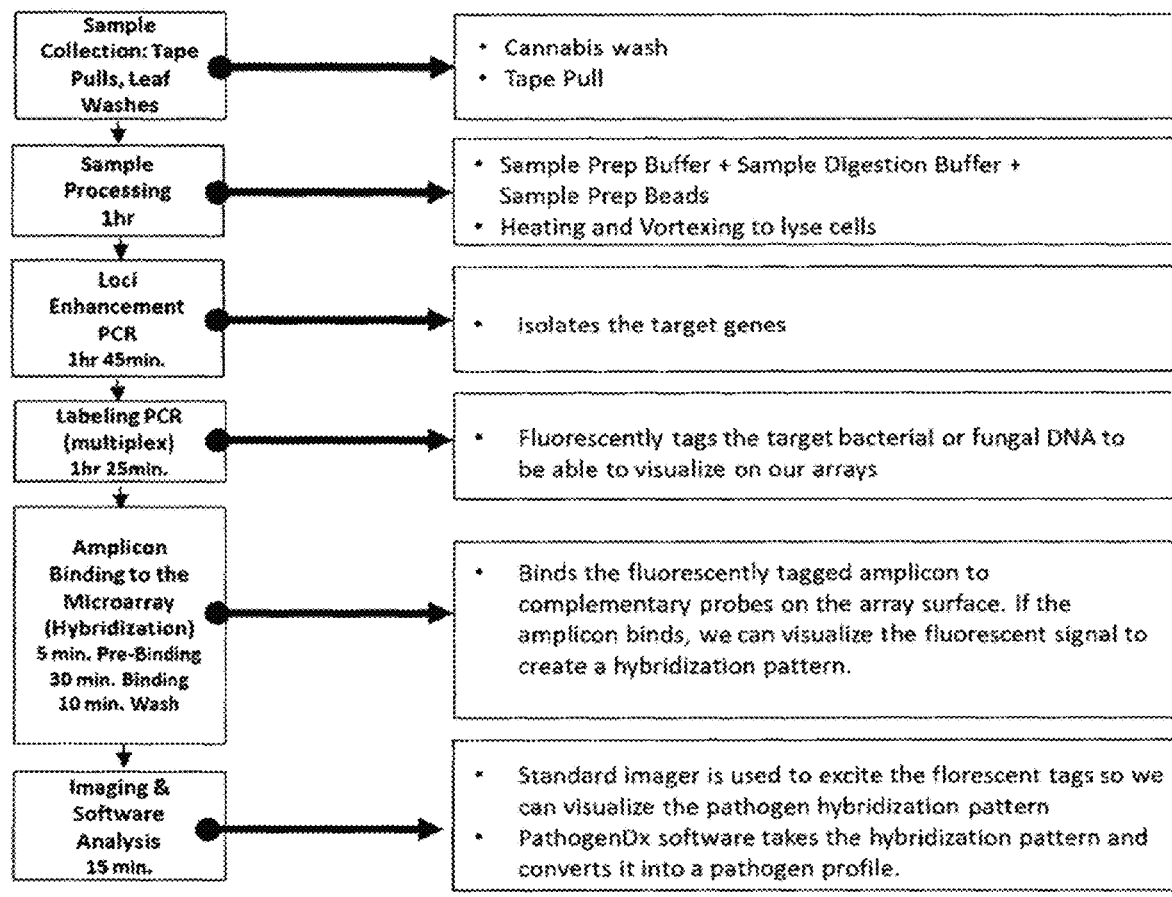
FIG. 9 is a flow diagram illustrating the processing of unpurified *Cannabis* wash or other surface sampling from *Cannabis* (and related plant material) so as to PCR amplify the raw *Cannabis* or related plant material, and then to perform microarray analysis on that material so as to analyze the pathogen complement of those plant samples

FIG. 9 shows a flow diagram to describe how an embodiment is used to analysis the bacterial pathogen or yeast and mold complement of a *Cannabis* or related plant sample. Pathogen samples can be harvested from *Cannabis* plant material by tape pulling of surface bound pathogen or by simple washing of the leaves or buds or stems, followed by a single multiplex "Loci Enhancement" Multiplex PCR reaction, which is then followed by a single multiplex "Labelling PCR". A different pair of two step PCR reactions is used to analyze bacteria, than the pair of two step PCR reactions used to analyze fungi, yeast & mold. In all cases, the DNA of the target bacteria or fungi, yeast & mold are PCR amplified without extraction or characterization of the DNA prior to two step PCR. Subsequent to the Loci Enhancement and Labelling PCR steps, the resulting PCR product is simply diluted into binding buffer and then applied to the microarray test. The subsequent microarray steps required for analysis (hybridization and washing) are performed at lab ambient temperature.

Figure 10:
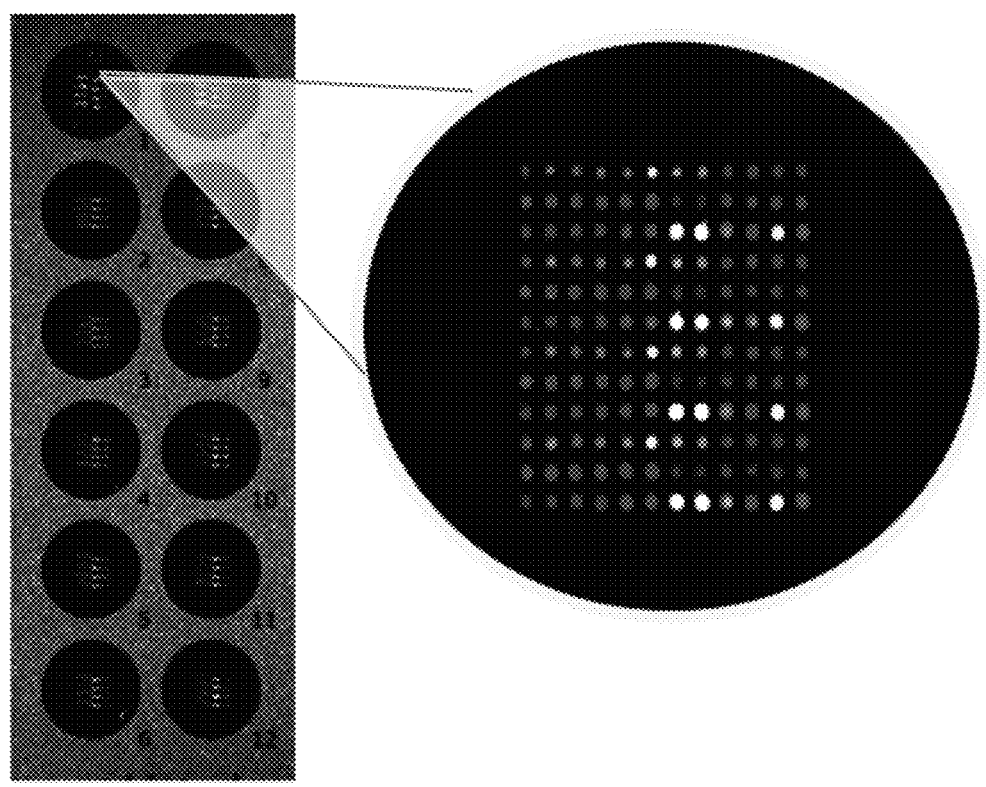
FIG. 10 is a representative image of the microarray format used to implement the nucleic acid probes. This representative format comprises 12 microarrays printed on a glass slide, each separated by a Teflon divider (left). Each microarray queries the full pathogen detection panel in quadruplicate. Also, shown is a blow-up (right) of one such microarray for the analysis of pathogens in *Cannabis* and related plant materials. The Teflon border about each microarray is fit to localize about 50 μL fluid sample for hybridization analysis where fluorescent labeled amplicons and placed onto the microarray for 30 min at room temperature, followed by washing at room temperature then microarray image scanning of the dye-labelled pathogen and host *Cannabis* DNA.

FIG. 10 provide images of a representative implementation of microarrays used in an embodiment. In this implementation, all nucleic acid probes required for bacterial analysis, along with *Cannabis* DNA controls (Tables 7 and 10) are fabricated into a single 144 element (12×12) microarray, along with additional bacterial and *Cannabis* probes such as those in Table 10. In this implementation, all nucleic acid probes required for fungi, yeast & mold analysis along with *Cannabis* DNA controls were fabricated into a single 144 element (12×12) microarray, along with additional fungal probes shown in Table 9. The arrays are manufactured on PTFE coated glass slides as two columns of 6 identical microarrays. Each of the 12 identical microarrays is capable of performing, depending on the nucleic acid probes employed, a complete microarray-based analysis bacterial analysis or a complete microarray-based analysis of fungi, yeast & mold. Nucleic acid probes were linked to the glass support via microfluidic printing, either piezoelectric or contact based or an equivalent. The individual microarrays are fluidically isolated from the other 11 in this case, by the hydrophobic PTFE coating, but other methods of physical isolation can be employed.

Figure 11B:
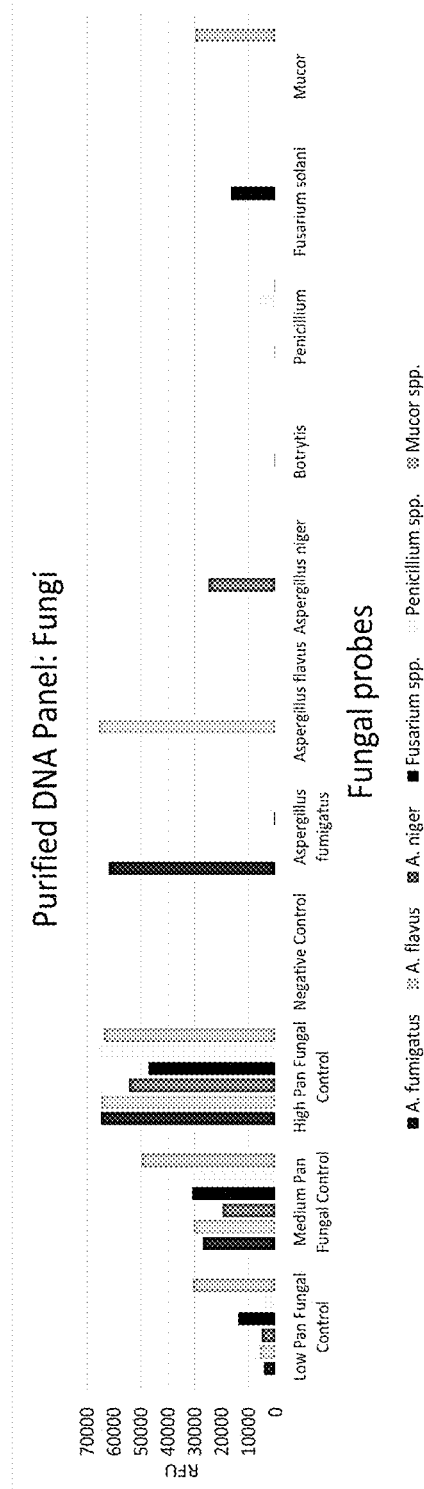
Figure 12:
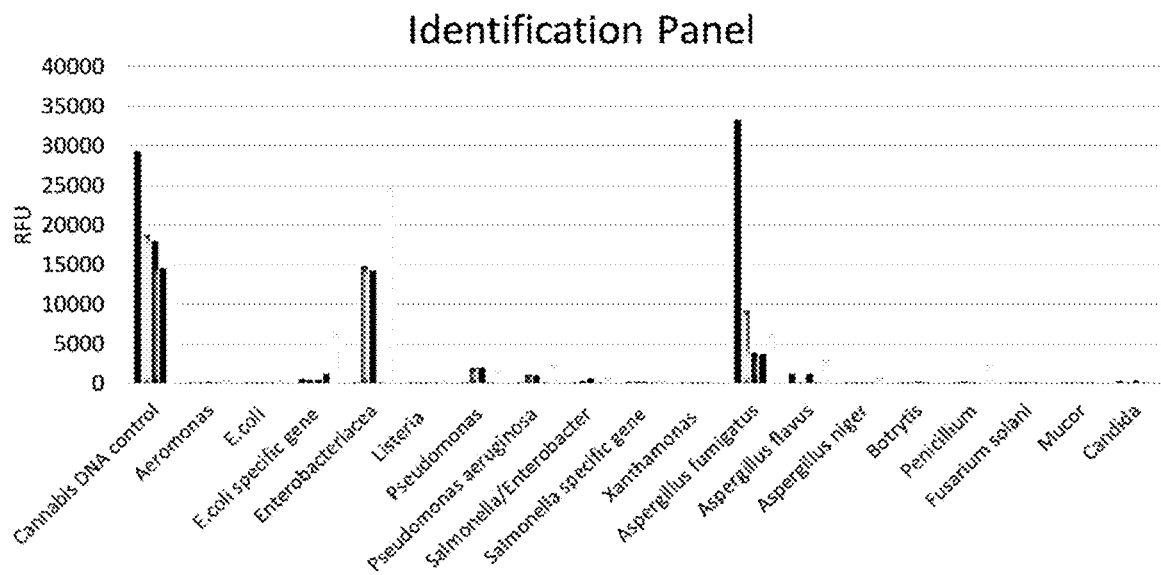
FIG. 12 shows representative microarray hybridization data obtained from 5 representative raw *Cannabis* wash samples. In each case, the raw pathogen complement of these 5 samples is PCR amplified, then hybridized on the microarray via the microarray probes described above. The data show that in this microarray format, specific bacterial, yeast, mold and fungal contaminants can be specifically identified via room temperature hybridization and washing.

FIGS. 11A-11B display representative DNA microarray analysis of an embodiment. In this case, purified bacterial DNA or purified fungal DNA has been used, to test for affinity and specificity subsequent to the two-step PCR reaction and microarray-based hybridization analysis. As can be seen, the nucleic acid probes designed to detect each of the bacterial DNA (top) or fungal DNA (bottom) have bound to the target DNA correctly via hybridization and thus have correctly detected the bacterium or yeast. FIG. 12 displays representative DNA microarray analysis of an embodiment. In this case, 5 different unpurified raw *Cannabis* leaf wash samples were used to test for affinity and specificity subsequent to the two-step PCR reaction and microarray-based hybridization analysis. Both bacterial and fungal analysis has been performed on all 5 leaf wash samples, by dividing each sample into halves and subsequently processing them each for analysis of bacteria or for analysis of fungi, yeast & mold. The data of FIG. 12 were obtained by combining the outcome of both assays. FIG. 12 shows that the combination of two step PCR and microarray hybridization analysis, as described in FIG. 9, can be used to analyze the pathogen complement of a routine *Cannabis* leaf wash. It is expected, but not shown that such washing of any plant material could be performed similarly.

FIG. 13 displays representative DNA microarray analysis of an embodiment. In this case, one unpurified (raw) *Cannabis* leaf wash sample was used and was compared to data obtained from a commercially-obtained homogenous yeast vitroid culture of live *Candida* to test for affinity and specificity subsequent to the two-step PCR reaction and microarray-based hybridization analysis. Both *Cannabis* leaf wash and cultured fungal analysis have been performed by processing them each for analysis via probes specific for fungi (see Tables 9 and 11).

The data of FIG. 13 were obtained by combining the outcome of analysis of both the leaf wash and yeast vitroid culture samples. The data of FIG. 13 show that the combination of two step PCR and microarray hybridization analysis, as described in FIG. 9, can be used to interrogate the fungal complement of a routine *Cannabis* leaf wash as adequately as can be done with a pure (live) fungal sample. It is expected that fungal analysis via such washing of any plant material could be performed similarly.

Figure 14:
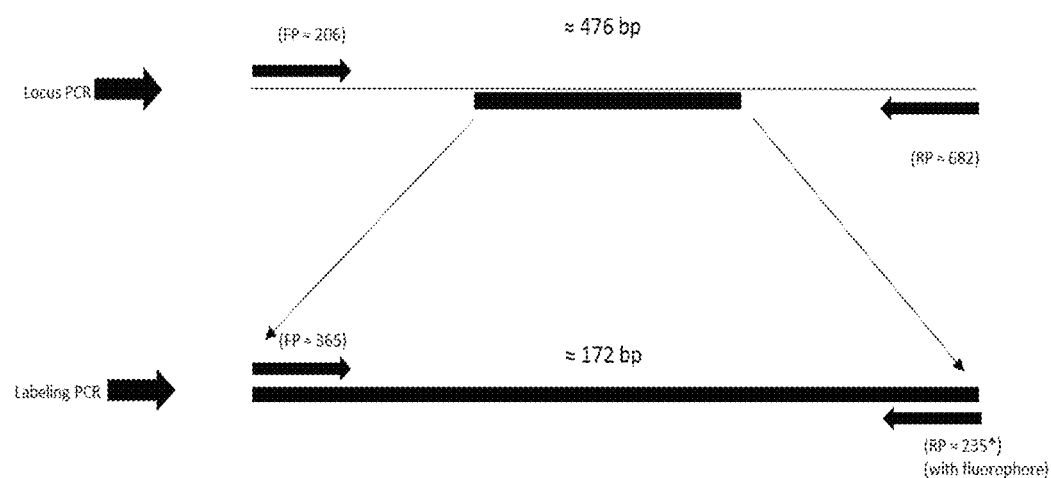
FIG. 14 shows a graphical representation of the position of PCR primers employed in a variation of an embodiment for low level detection of Bacteria in the Family Enterobacteriaceae including *E. coli*. These PCR primers are used to selectively amplify and dye label DNA from targeted organisms for analysis via microarray hybridization.

FIG. 14 shows a graphical representation of the position of PCR primers employed in a variation of an embodiment for low level detection of Bacteria in the Family Enterobacteriaceae including *E. coli*. These PCR primers are used to selectively amplify and dye label DNA from targeted organisms for analysis via microarray hybridization.

Figure 15A:
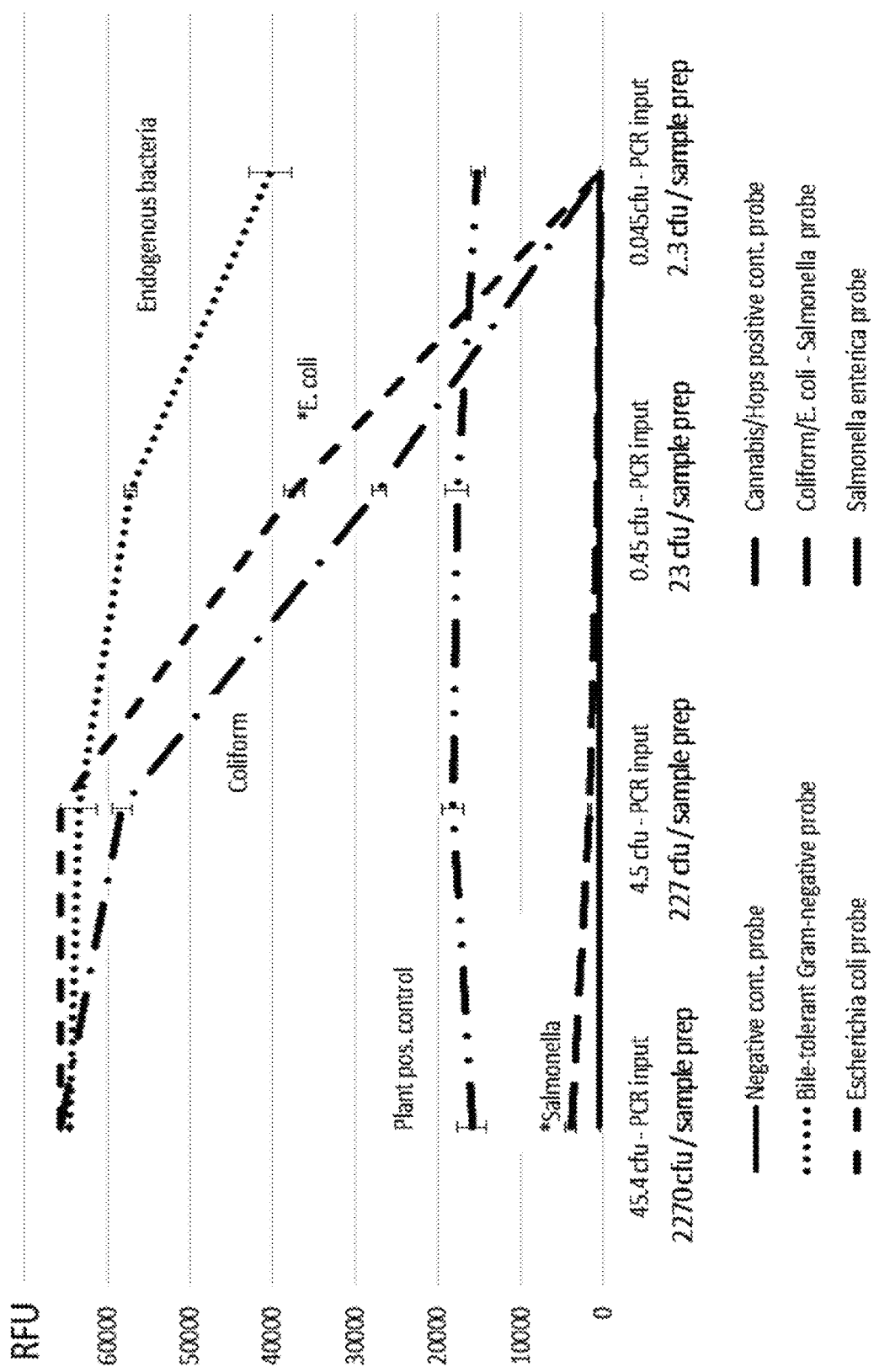
FIG. 15A is a graphical representation of microarray hybridization data demonstrating low level detection of *E. coli* O157:H7 from certified reference material consisting of enumerated colonies of specified bacteria spiked onto *Humulus lupulus*, (Hop plant).
Figure 15B:
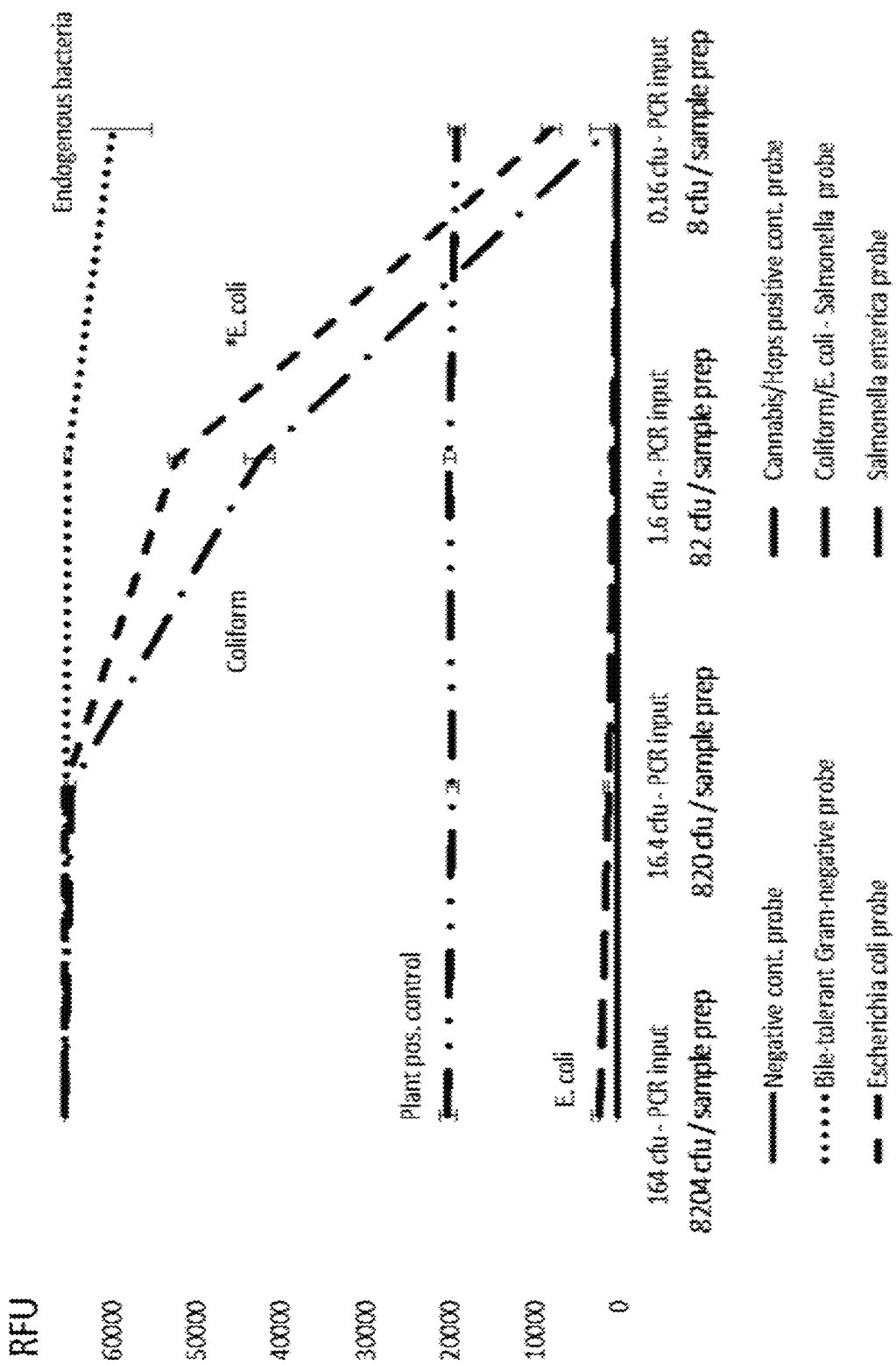
FIG. 15B is a graphical representation of microarray hybridization data demonstrating low level detection of *E. coli* O1111 from certified reference material consisting of enumerated colonies of specified bacteria spiked onto *Humulus lupulus*, (Hop plant).
Figure 15C:
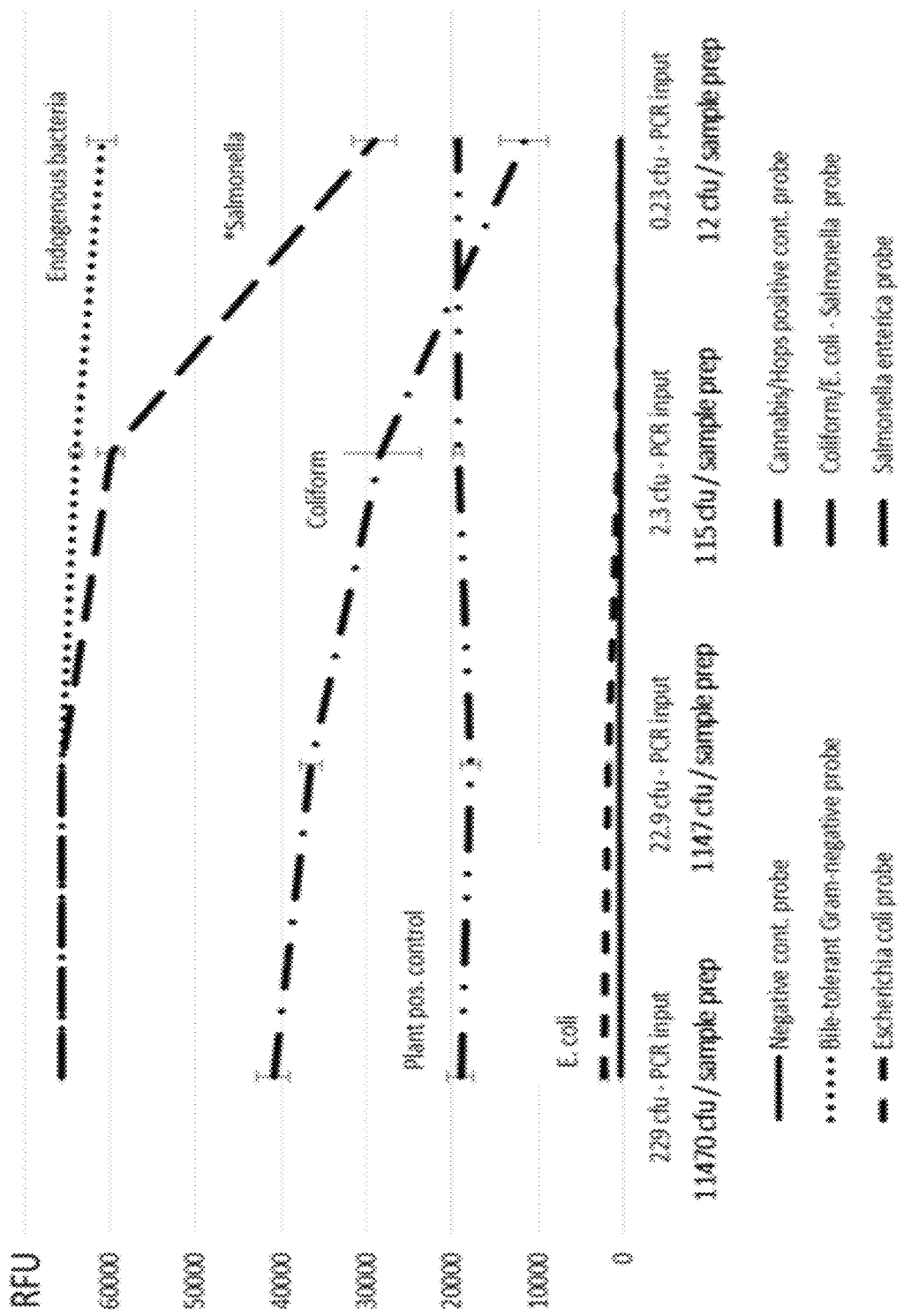
FIG. 15C is a graphical representation of microarray hybridization data demonstrating low level detection of *Salmonella enterica* from certified reference material consisting of enumerated colonies of specified bacteria spiked onto *Humulus lupulus*, (Hop plant).

FIGS. 15A-15C illustrate representative DNA microarray analysis demonstrating assay sensitivity over a range of microbial inputs. In this case, certified reference material consisting of enumerated bacterial colonies of *E. coli* O157:

H7, *E. coli* O111 (FIGS. 15A, 15B) and *Salmonella enterica* (FIG. 15C) were spiked as a dilution series onto a hops plant surrogate matrix then processed using the assay version described for FIG. 14. Hybridization results from relevant probes from FIG. 7 are shown. The larger numbers on the x-axis represents the total number of bacterial colony forming units (CFU) that were spiked onto each hops plant sample, whereas the smaller numbers on the x-axis represent the number of CFU's of the spiked material that were actually inputted into the assay. Only about ⅕₀ of the original spiked hops sample volume was actually analyzed. The smaller numbers upon the x-axis of FIGS. 15A-15C are exactly $\frac{1}{50}^{th}$ that of the total (lower) values. As is seen, FIGS. 15A-15C show that the microarray test of an embodiment can detect less than 1 CFU per microarray assay. The nucleic acid targets within the bacterial genomes displayed in FIGS. 15A-15C comprise 16S rDNA. There are multiple copies of the 16S rDNA gene in each of these bacterial organisms, which enables detection at <1 CFU levels. Since a colony forming unit approximates a single bacterium in many cases, the data of FIGS. 15A-15C demonstrate that the present microarray assay has sensitivity which approaches the ability to detect a single (or a very small number) of bacteria per assay. Similar sensitivity is expected for all bacteria and eukaryotic microbes in that it is known that they all present multiple copies of the ribosomal rDNA genes per cell.

Tables 12A and 12B show a collection of representative microarray hybridization data obtained from powdered dry food samples with no enrichment and 18-hour enrichment for comparison. The data shows that bacterial microbes were successfully detected on the microarrays of the present invention without the need for enrichment.

FIG. 16 and Tables 13-15 describes embodiments for the analysis of fruit, embodiments for the analysis of vegetables and embodiments for the analysis of other plant matter. The above teaching shows, by example, that unprocessed leaf and bud samples in *Cannabis* and hops may be washed in an aqueous water solution, to yield a water-wash containing microbial pathogens which can then be analyzed via the present combination of RSG and microarrays.

If fresh leaf, flower, stem or root materials from fruit and vegetables are also washed in a water solution in that same way (when fresh, or after drying and grinding or other types or processing), then the present combination of RSG and microarray analysis would be capable of recovering and analyzing the DNA complement of those microbes in those other plant materials. At least two methods of sample collection are possible for fruit and vegetables. One method is the simple rinsing of the fruit, exactly as described for *Cannabis*, above. Another method of sample collection from fruits and vegetables is a "tape pull", wherein a piece of standard forensic tape is applied to the surface of the fruit, then pulled off. Upon pulling, the tape is then soaked in the standard wash buffer described above, to suspend the microbes attached to the tape. Subsequent to the tape-wash step, all other aspects of the processing and analysis (i.e., raw sample genotyping, PCR, then microarray analysis) are exactly as described above.

TABLE 12A

Representative microarray data obtained from powdered dry food samples

| | Sample Type | | | | | | | | | |
|---|---|---|---|---|---|---|---|---|---|---|
| | Whey Protein Shake Vanilla | | Whey Protein Shake Chocolate | | Chewable Berry Tablet | | Vanilla Shake | | Pea Protein | |
| | Enrichment time | | | | | | | | | |
| | 0 hours | 18 hours | 0 hours | 18 hours | 0 hours | 18 hours | 0 hours | 18 hours | 0 hours | 18 hours |
| Negative Control Probe | 289 | 318 | 349 | 235 | 327 | 302 | 358 | 325 | 321 | 299 |
| Total Aerobic Bacteria Probes | | | | | | | | | | |
| High sensitivity | 26129 | 38896 | 16629 | 11901 | 3686 | 230 | 32747 | 12147 | 41424 | 40380 |
| Medium sensitivity | 5428 | 6364 | 3308 | 2794 | 876 | 215 | 7310 | 2849 | 15499 | 8958 |
| Low sensitivity | 2044 | 3419 | 1471 | 990 | 446 | 181 | 2704 | 1062 | 4789 | 3887 |
| Bile-tolerant Gram-negative Probes | | | | | | | | | | |
| High sensitivity | 2639 | 350 | 1488 | 584 | 307 | 305 | 1041 | 472 | 15451 | 8653 |
| Medium sensitivity | 1713 | 328 | 892 | 493 | 322 | 362 | 615 | 380 | 6867 | 4997 |
| Low sensitivity | 974 | 600 | 749 | 621 | 595 | 688 | 821 | 929 | 2459 | 1662 |
| Total Enterobacteriaceae Probes | | | | | | | | | | |
| High sensitivity | 1131 | 306 | 363 | 310 | 346 | 318 | 273 | 331 | 4260 | 3149 |
| Medium sensitivity | 479 | 296 | 320 | 297 | 329 | 339 | 314 | 342 | 1489 | 990 |
| Low sensitivity | 186 | 225 | 203 | 165 | 205 | 181 | 207 | 200 | 216 | 259 |
| 16S rDNA Species Probes | | | | | | | | | | |
| *Escherichia coli/Shigella* spp. | 233 | 205 | 255 | 219 | 207 | 255 | 215 | 214 | 242 | 198 |
| *S. enterica/enterobacter* spp. | 203 | 183 | 186 | 281 | 212 | 299 | 197 | 257 | 308 | 303 |
| *Bacillus* spp. | 154 | 172 | 189 | 114 | 307 | 156 | 169 | 153 | 233 | 259 |
| *Pseudomonas* spp. | 549 | 201 | 202 | 251 | 148 | 216 | 303 | 276 | 2066 | 983 |
| Organism Specific Gene Probes | | | | | | | | | | |
| tuf gene(*E. coli*) | 204 | 129 | 180 | 272 | 158 | 190 | 191 | 183 | 186 | 192 |
| stx1 gene(*E. coli*) | 241 | 178 | 171 | 240 | 289 | 304 | 195 | 245 | 149 | 191 |
| stx2 gene(*E. coli*) | 145 | 96 | 136 | 125 | 182 | 224 | 130 | 142 | 85 | 127 |
| invA (*Salmonella* spp.) | 215 | 265 | 210 | 284 | 204 | 256 | 239 | 285 | 237 | 229 |

TABLE 12B

Representative microarray data obtained from powdered dry food samples

| | Rice Protein | | Work-out Shake FP | | Work-out Shake BR | | Vanilla Shake | |
|---|---|---|---|---|---|---|---|---|
| | 0 hours | 18 hours | 0 hours | 18 hours | 0 hours | 18 hours | 0 hours | 18 hours |
| Negative Control Probe | 351 | 351 | 271 | 309 | 299 | 332 | 246 | 362 |
| Total Aerobic Bacteria Probes | | | | | | | | |
| High sensitivity | 471 | 288 | 17146 | 266 | 19207 | 261 | 41160 | 47198 |
| Medium sensitivity | 161 | 187 | 3120 | 229 | 3309 | 311 | 10060 | 22103 |
| Low sensitivity | 186 | 239 | 1211 | 261 | 1223 | 264 | 3673 | 6750 |
| Bile-tolerant Gram-negative Probes | | | | | | | | |
| High sensitivity | 326 | 372 | 375 | 380 | 412 | 363 | 1418 | 358 |
| Medium sensitivity | 304 | 362 | 341 | 391 | 308 | 356 | 699 | 394 |
| Low sensitivity | 683 | 942 | 856 | 689 | 698 | 864 | 848 | 665 |
| Total Enterobacteriaceae Probes | | | | | | | | |
| High sensitivity | 277 | 329 | 317 | 327 | 298 | 326 | 290 | 349 |
| Medium sensitivity | 326 | 272 | 296 | 291 | 297 | 263 | 262 | 307 |
| Low sensitivity | 215 | 207 | 204 | 288 | 213 | 269 | 195 | 247 |
| 16S rDNA Species Probes | | | | | | | | |
| *Escherichia coli/Shigella* spp. | 228 | 229 | 216 | 267 | 221 | 253 | 220 | 207 |
| *S. enterica/enterobacter* spp. | 226 | 281 | 238 | 268 | 197 | 254 | 255 | 216 |
| *Bacillus* spp. | 157 | 166 | 812 | 208 | 915 | 216 | 415 | 168 |
| *Pseudomonas* spp. | 199 | 225 | 247 | 251 | 211 | 259 | 277 | 225 |
| Organism Specific Gene Probes | | | | | | | | |
| tuf gene(*E. coli*) | 150 | 149 | 126 | 206 | 163 | 212 | 215 | 166 |
| stx1 gene(*E. coli*) | 270 | 247 | 211 | 299 | 239 | 307 | 175 | 185 |
| stx2 gene(*E. coli*) | 158 | 178 | 127 | 205 | 138 | 175 | 128 | 100 |
| invA (*Salmonella* spp.) | 257 | 241 | 249 | 264 | 220 | 258 | 239 | 245 |

The data of Tables 13-15 demonstrates that simple washing of the fruit and tape pull sampling of the fruit generate similar microbial data. The blueberry sample is shown to be positive for *Botrytis*, as expected, since *Botrytis* is a well-known fungal contaminant on blueberries. The lemon sample is shown to be positive for *Penicillium*, as expected, since *Penicillium* is a well-known fungal contaminant for lemons.

TABLE 13

Representative microarray hybridization data obtained from blueberry and lemon washes.

| | Blueberry | | Lemon | |
|---|---|---|---|---|
| Collection Type | | | | |
| Produce Wash Protocol | | | | |
| | Wash 1 blueberry in 2 ml 20 mM Borate, vortex 30 seconds | | Wash 1 piece moldy lemon in 2 ml 20 mM Borate, vortex 30 seconds | |
| Dilution Factor | NONE | 1:20 | NONE | 1:20 |
| *A. fumigatus* 1 | 65 | 61 | 62 | 57 |
| *A. fumigatus* 2 | 66 | 61 | 58 | 131 |
| *A. fumigatus* 3 | 69 | 78 | 55 | 127 |
| *A. fumigatus* 4 | 80 | 198 | 63 | 161 |
| *A. fumigatus* 5 | 98 | 68 | 59 | 70 |
| *A. flavus* 1 | 111 | 65 | 197 | 58 |
| *A. flavus* 2 | 64 | 66 | 71 | 49 |
| *A. flavus* 3 | 72 | 79 | 54 | 49 |
| *A. flavus* 4 | 95 | 71 | 66 | 125 |
| *A. flavus* 5 | 59 | 55 | 45 | 47 |
| *A. niger* 1 | 91 | 75 | 61 | 61 |
| *A. niger* 2 | 185 | 68 | 61 | 57 |
| *A. niger* 3 | 93 | 66 | 62 | 61 |
| *A. niger* 4 | 1134 | 74 | 75 | 64 |
| *Botrytis* spp. 1 | 26671 | 27605 | 60 | 55 |
| *Botrytis* spp. 2 | 26668 | 35611 | 59 | 57 |
| *Penicillium* spp. 1 | 63 | 69 | 2444 | 4236 |
| *Penicillium* spp. 2 | 71 | 69 | 4105 | 7426 |
| *Fusarium* spp. 1 | 175 | 69 | 59 | 78 |
| *Fusarium* spp. 2 | 71 | 73 | 84 | 62 |
| *Mucor* spp. 1 | 71 | 57 | 58 | 61 |
| *Mucor* spp. 2 | 61 | 290 | 66 | 61 |
| Total Y & M 1 | 20052 | 21412 | 8734 | 7335 |
| Total Y & M 2 | 17626 | 8454 | 5509 | 5030 |

TABLE 14

Representative microarray hybridization data obtained from blueberry washes and tape pulls Sample: Moldy Blueberry Collection Type: Tape Pull

| ID | 1A1 | 1A1 | 1A2 | 1A2 | 1A3 | 1A3 | 1B1 | 1B1 | 1B2 | 1B2 | 1B3 | 1B3 |
|---|---|---|---|---|---|---|---|---|---|---|---|---|
| Collection Point 1 | 500 ul 20 mM Borate Buffer, vortex 30 seconds | | | | | | 500 ul 20 mM Borate + Triton Buffer, vortex 30 seconds | | | | | |
| Collection Point 2 | Add 15 mg zirconia beads, vortex, Heat 5 min 95° C., Vortex 15 seconds | | | | | | Add 15 mg zirconia beads, vortex, Heat 5 min 95° C., Vortex 15 seconds | | | | | |
| Collection Point 3 | Heat 5 min 95° C. vortex 15 seconds | | | | | | Heat 5 min 95° C. vortex 15 seconds | | | | | |
| Dilution Factor | NONE | 1:20 | NONE | 1:20 | NONE | 1:20 | NONE | 1:20 | NONE | 1:20 | NONE | 1:20 |
| *A. fumigatus* 1 | 66 | 388 | 83 | 77 | 97 | 313 | 95 | 68 | 76 | 55 | 75 | 60 |
| *A. fumigatus* 2 | 97 | 100 | 82 | 118 | 69 | 56 | 87 | 67 | 185 | 76 | 58 | 52 |
| *A. fumigatus* 3 | 77 | 94 | 82 | 1083 | 87 | 61 | 93 | 84 | 75 | 378 | 73 | 64 |
| *A. fumigatus* 4 | 84 | 151 | 94 | 118 | 96 | 80 | 115 | 85 | 85 | 93 | 190 | 88 |
| *A. fumigatus* 5 | 63 | 75 | 96 | 71 | 78 | 61 | 98 | 74 | 68 | 98 | 70 | 533 |
| *A. flavus* 1 | 200 | 107 | 113 | 61 | 204 | 58 | 105 | 73 | 62 | 68 | 64 | 65 |
| *A. flavus* 2 | 70 | 104 | 64 | 57 | 133 | 281 | 111 | 78 | 377 | 314 | 57 | 50 |
| *A. flavus* 3 | 83 | 90 | 94 | 150 | 99 | 90 | 96 | 222 | 1162 | 86 | 80 | 73 |
| *A. flavus* 4 | 76 | 125 | 92 | 146 | 87 | 174 | 241 | 78 | 115 | 69 | 105 | 85 |
| *A. flavus* 5 | 80 | 153 | 77 | 72 | 78 | 439 | 71 | 86 | 280 | 58 | 62 | 57 |
| *A. niger* 1 | 409 | 178 | 122 | 72 | 80 | 70 | 76 | 71 | 152 | 117 | 65 | 53 |
| *A. niger* 2 | 78 | 292 | 79 | 65 | 715 | 666 | 74 | 70 | 68 | 731 | 70 | 54 |
| *A. niger* 3 | 86 | 76 | 87 | 558 | 78 | 60 | 70 | 81 | 96 | 63 | 478 | 58 |
| *A. niger* 4 | 164 | 70 | 92 | 108 | 197 | 69 | 130 | 75 | 76 | 148 | 73 | 65 |
| *Botrytis* spp. 1 | 41904 | 26549 | 28181 | 29354 | 25304 | 25685 | 57424 | 33783 | 57486 | 49803 | 33176 | 32153 |
| *Botrytis* spp. 2 | 36275 | 25518 | 29222 | 27076 | 26678 | 27675 | 49480 | 32899 | 52817 | 34322 | 29693 | 32026 |
| *Penicillium* spp. 1 | 80 | 81 | 83 | 64 | 96 | 60 | 79 | 80 | 176 | 60 | 385 | 53 |
| *Penicillium* spp. 2 | 90 | 93 | 81 | 80 | 114 | 59 | 98 | 69 | 470 | 65 | 478 | 56 |
| *Fusarium* spp. 1 | 77 | 71 | 69 | 62 | 112 | 55 | 61 | 274 | 617 | 81 | 59 | 757 |
| *Fusarium* spp. 2 | 91 | 82 | 107 | 74 | 101 | 65 | 91 | 66 | 123 | 63 | 71 | 583 |
| *Mucor* spp. 1 | 90 | 314 | 73 | 88 | 105 | 61 | 77 | 79 | 741 | 180 | 172 | 74 |
| *Mucor* spp. 2 | 83 | 69 | 73 | 69 | 91 | 67 | 111 | 102 | 455 | 88 | 70 | 133 |
| Total Y & M 1 | 23637 | 18532 | 15213 | 17668 | 18068 | 19762 | 18784 | 15550 | 20625 | 17525 | 25813 | 18269 |
| Total Y & M 2 | 12410 | 8249 | 9281 | 11526 | 8543 | 13007 | 14180 | 14394 | 9905 | 8972 | 15112 | 12678 |

The data embodied in FIG. 16 and Tables 13-15 demonstrate the use of an embodiment, for the recovery and analysis of yeast microbes on the surface of fruit (blueberries and lemons in this case), but an embodiment could be extended to other fruits and vegetables for the analysis of both bacterial and fungal contamination.

TABLE 15

Representative microarray hybridization data obtained from lemon washes and tape pulls.

Sample: Moldy Lemon

Collection Type: Tape Pull

| ID | 1A1 Lemon | 1A2 Lemon | 1A3 Lemon | 1B1 Lemon | 1B2 Lemon |
|---|---|---|---|---|---|
| Collection Point 1 | 500 ul 20 mM Borate + Triton Buffer, vortex 30 seconds | | | | |
| Collection Point 2 | Add 15 mg zirconia beads, vortex, Heat 5 min 95° C., Vortex 15 seconds | | | | Add 15 mg zirconia beads, vortex, Heat 5 min 95° C., Vortex 15 seconds |

TABLE 15-continued

Representative microarray hybridization data obtained from lemon washes and tape pulls.

| | Sample | | | | |
|---|---|---|---|---|---|
| | Moldy Lemon | | | | |
| | Collection Type | | | | |
| | Tape Pull | | | | |
| | ID | | | | |
| | 1A1 Lemon | 1A2 Lemon | 1A3 Lemon | 1B1 Lemon | 1B2 Lemon |
| Collection Point 3 | | | Heat 5 min 95° C. vortex 15 seconds | | |
| Dilution Factor | | | NONE | | |
| A. fumigatus 1 | 96 | 83 | 75 | 83 | 64 |
| A. fumigatus 2 | 221 | 73 | 71 | 66 | 101 |
| A. fumigatus 3 | 87 | 88 | 85 | 92 | 122 |
| A. fumigatus 4 | 83 | 85 | 91 | 72 | 97 |
| A. fumigatus 5 | 448 | 100 | 84 | 114 | 78 |
| A. flavus 1 | 85 | 79 | 70 | 66 | 63 |
| A. flavus 2 | 77 | 82 | 77 | 79 | 63 |
| A. flavus 3 | 133 | 66 | 86 | 60 | 67 |
| A. flavus 4 | 96 | 85 | 81 | 98 | 88 |
| A. flavus 5 | 68 | 62 | 65 | 106 | 59 |
| A. niger 1 | 73 | 88 | 77 | 73 | 73 |
| A. niger 2 | 74 | 84 | 81 | 71 | 103 |
| A. niger 3 | 90 | 86 | 87 | 74 | 78 |
| A. niger 4 | 82 | 93 | 104 | 86 | 161 |
| Botrytis spp. 1 | 82 | 75 | 75 | 77 | 68 |
| Botrytis spp. 2 | 91 | 74 | 83 | 67 | 62 |
| Penicillium spp. 1 | 3824 | 5461 | 5500 | 4582 | 5290 |
| Penicillium spp. 2 | 7586 | 8380 | 11177 | 6528 | 8167 |
| Fusarium spp. 1 | 101 | 62 | 61 | 70 | 279 |
| Fusarium spp. 2 | 77 | 122 | 78 | 68 | 233 |
| Mucor spp. 1 | 74 | 110 | 89 | 76 | 57 |
| Mucor spp. 2 | 132 | 1302 | 90 | 84 | 61 |
| Total Y & M 1 | 8448 | 12511 | 9249 | 12844 | 8593 |
| Total Y & M 2 | 9275 | 8716 | 11585 | 10758 | 4444 |

Table 16 shows embodiments for the analysis of environmental water samples/specimens. The above teaching shows by example that unprocessed leaf and bud samples in Cannabis and hops may be washed in an aqueous water solution, to yield a water-wash containing microbial pathogens which can then be analyzed via the present combination of Raw Sample Genotyping (RSG) and microarrays. If a water sample containing microbes were obtained from environmental sources (such as well water, or sea water, or soil runoff or the water from a community water supply) and then analyzed directly, or after ordinary water filtration to concentrate the microbial complement onto the surface of the filter, that the present combination of RSG and microarray analysis would be capable of recovering and analyzing the DNA complement of those microbes.

The data embodied in Table 16 were obtained from 5 well-water samples (named 2H, 9D, 21, 23, 25) along with 2 samples of milliQ laboratory water (obtained via reverse osmosis) referred to as "Negative Control". All samples were subjected to filtration on a sterile 0.4 um filter. Subsequent to filtration, the filters, with any microbial contamination that they may have captured, were then washed with the standard wash solution, exactly as described above for the washing of Cannabis and fruit. Subsequent to that washing, the suspended microbes in wash solution were then subjected to exactly the same combination of centrifugation (to yield a microbial pellet) then lysis and PCR of the unprocessed pellet-lysate (exactly as described above for Cannabis), followed by PCR and microarray analysis, also as described for Cannabis.

TABLE 16

Representative microarray data from raw water filtrate

| | Sample ID | | | | | | | | | | |
|---|---|---|---|---|---|---|---|---|---|---|---|
| | 2 H | 2 H | 9 D | 9 D | 21 | 21 | 23 | 23 | 25 | 25 | Negative Control |
| Imager Calibration High | 311 | 335 | 322 | 379 | 341 | 348 | 345 | 325 | 354 | 343 | 333 |
| Imager Calibration Med | 280 | 314 | 268 | 286 | 288 | 231 | 253 | 295 | 267 | 295 | 244 |
| Imager Calibration Low | 245 | 296 | 302 | 324 | 254 | 268 | 293 | 285 | 271 | 340 | 275 |
| Cannabis cont. | 310 | 330 | 313 | 255 | 323 | 368 | 313 | 322 | 274 | 332 | 322 |
| Cannabis cont. | 313 | 237 | 298 | 271 | 298 | 288 | 296 | 280 | 249 | 284 | 297 |
| Cannabis cont. | 208 | 265 | 276 | 250 | 267 | 327 | 255 | 258 | 253 | 282 | 370 |
| Total Yeast & Mold | 284 | 324 | 290 | 307 | 272 | 361 | 296 | 288 | 271 | 321 | 469 |

TABLE 16-continued

Representative microarray data from raw water filtrate

| | Sample ID | | | | | | | | | | Negative Control |
|---|---|---|---|---|---|---|---|---|---|---|---|
| | 2 H | 2 H | 9 D | 9 D | 21 | 21 | 23 | 23 | 25 | 25 | |
| Total Yeast & Mold | 251 | 259 | 294 | 290 | 309 | 308 | 285 | 281 | 275 | 299 | 293 |
| Total Yeast & Mold | 282 | 280 | 294 | 280 | 299 | 284 | 275 | 286 | 299 | 259 | 232 |
| Total Aerobic bacteria High | *40101* | *42007* | *47844* | *47680* | *45102* | *44041* | *43520* | *41901* | *46459* | *46783* | 135 |
| Total Aerobic bacteria Medium | *14487* | *12314* | *24189* | *26158* | *19712* | *16210* | *17943* | *15474* | *25524* | *18507* | 157 |
| Total Aerobic bacteria Low | *4885* | *5629* | *7625* | *6456* | *5807* | *4505* | *5316* | *6022* | *6264* | *6974* | 159 |
| Negative Control | 293 | 359 | 303 | 339 | 312 | 329 | 306 | 377 | 307 | 335 | 307 |
| *Aspergillus fumigatus* | 285 | 291 | 284 | 268 | 289 | 265 | 271 | 281 | 269 | 248 | 228 |
| *Aspergillus flavus* | 184 | 211 | 201 | 344 | 237 | 179 | 212 | 213 | 163 | 204 | 171 |
| *Aspergillus niger* | 226 | 213 | 228 | 273 | 190 | 195 | 245 | 206 | 222 | 209 | 172 |
| *Botrytis* spp. | 219 | 285 | 258 | 302 | 275 | 219 | 202 | 288 | 221 | 248 | 214 |
| *Alternaria* spp. | 81 | 97 | 76 | 89 | 58 | 76 | 75 | 175 | 117 | 174 | 167 |
| *Penicillium paxilli* | 135 | 162 | 215 | 142 | 127 | 161 | 103 | 115 | 238 | 190 | 200 |
| *Penicillium oxalicum* | 119 | 107 | 161 | 131 | 135 | 241 | 178 | 158 | 140 | 143 | 194 |
| *Penicillium* spp. | 50 | 123 | 179 | 177 | 128 | 138 | 146 | 163 | 148 | 115 | 184 |
| Can. alb/trop/dub | 261 | 236 | 235 | 230 | 250 | 213 | 276 | 244 | 245 | 237 | 194 |
| Can. glab/Sach & Kluv spp. | 146 | 165 | 196 | 128 | 160 | 215 | 185 | 217 | 215 | 177 | 225 |
| *Podosphaera* spp. | 111 | 119 | 100 | 122 | 192 | 105 | 95 | 43 | 169 | 27 | 143 |
| Bile-tolerant Gram-negative High | *16026* | *9203* | *13309* | *8426* | *16287* | *14116* | *10557* | *17558* | *15343* | *14285* | 183 |
| Bile-tolerant Gram-negative Medium | *12302* | *11976* | *9259* | *10408* | *13055* | *10957* | *11242* | *8416* | *9322* | *11785* | 196 |
| Bile-tolerant Gram-negative Low | *5210* | *7921* | *3818* | *3984* | *7224* | *6480* | *4817* | *6933* | *5021* | *5844* | 240 |
| Total Enterobacteriaceae High | 193 | 248 | 389 | 357 | 215 | 214 | 198 | 220 | 276 | 208 | 210 |
| Total Enterobacteriaceae Med | 246 | 214 | 297 | 246 | 244 | 224 | 219 | 245 | 252 | 229 | 207 |
| Total Enterobacteriaceae Low | 165 | 140 | 158 | 119 | 151 | 180 | 150 | 167 | 182 | 174 | 132 |
| Total Coliform | 121 | 148 | 158 | 117 | 129 | 117 | 155 | 157 | 125 | 178 | 152 |
| *Escherichia coli* specific gene | 31821 | 115 | 132 | 155 | 127 | 62 | 86 | 121 | 59 | 90 | 234 |
| stx1 gene | 67 | 0 | 2 | 0 | 0 | 23 | 21 | 28 | 0 | 0 | 116 |
| stx2 gene | 17 | 36 | 174 | 0 | 61 | 47 | 0 | 51 | 33 | 0 | 85 |
| *Salmonella* specific gene | 181 | 172 | 245 | 172 | 178 | 212 | 157 | 243 | 174 | 156 | 146 |
| *Bacillus* spp. | 137 | 135 | 174 | 112 | 164 | 143 | 163 | 182 | 168 | 152 | 149 |
| *Pseudomonas* spp. | 271 | 74 | 332 | 56 | 366 | 133 | 91 | 114 | 60 | 179 | 555 |
| *Escherichia coli/Shigella* spp. | 103 | 124 | 221 | 124 | 90 | 144 | 130 | 121 | 137 | 143 | 158 |
| *Salmonella enterica/enterobacter* spp. | 124 | 98 | 131 | 119 | 136 | 88 | 121 | 77 | 128 | 140 | 124 |
| *Erysiphe* Group 2 | 278 | 221 | 237 | 230 | 245 | 254 | 250 | 220 | 205 | 236 | 233 |
| *Trichoderma* spp. | 105 | 157 | 204 | 152 | 180 | 154 | 130 | 161 | 201 | 180 | 150 |
| *Escherichia coli* | 429 | 431 | 551 | 576 | 549 | 406 | 407 | 484 | 556 | 551 | 293 |
| *Aspergillus niger* | 218 | 212 | 216 | 297 | 255 | 312 | 221 | 202 | 238 | 231 | 209 |
| *Escherichia coli/Shigella* spp. | 163 | 193 | 220 | 202 | 308 | 280 | 121 | 271 | 341 | 317 | 124 |
| *Aspergillus fumigatus* | 713 | 865 | 862 | 830 | 784 | 657 | 827 | 803 | 746 | 812 | 793 |
| *Aspergillus flavus* | 155 | 261 | 198 | 156 | 239 | 171 | 250 | 218 | 210 | 258 | 219 |
| *Salmonella enterica* | 136 | 98 | 85 | 43 | 109 | 47 | 23 | 123 | 70 | 100 | 135 |
| *Salmonella enterica* | 68 | 53 | 52 | 41 | 60 | 92 | 26 | 28 | 55 | 81 | 116 |

The data seen in Table 16 demonstrate that microbes collected on filtrates of environmental water samples can be analyzed via the same combination of raw sample genotyping, then PCR and microarray analysis used for *Cannabis* and fruit washes. The italicized elements of Table 16 demonstrate that the 5 unprocessed well-water samples all contain aerobic bacteria and bile tolerant gram-negative bacteria. The presence of both classes of bacteria is expected for unprocessed (raw) well water. Thus, the data of Table 16 demonstrate that this embodiment of the present invention can be used for the analysis of environmentally derived water samples.

The above teaching shows that unprocessed leaf and bud samples in *Cannabis* and hops may be washed in an aqueous water solution to yield a water-wash containing microbial pathogens which can then be analyzed via the present combination of RSG and microarrays. The above data also show that environmentally-derived well water samples may be analyzed by an embodiment. Further, if a water sample containing microbes were obtained from industrial processing sources (such as the water effluent from the processing of fruit, vegetables, grain, meat) and then analyzed directly, or after ordinary water filtration to concentrate the microbial complement onto the surface of the filter, that the present combination of RSG and microarray analysis would be capable of recovering and analyzing the DNA complement of those microbes.

Further, if an air sample containing microbes as an aerosol or adsorbed to airborne dust were obtained by air filtration onto an ordinary air-filter (such as used in the filtration of air in an agricultural or food processing plant, or on factory floor, or in a public building or a private home) that such air-filters could then be washed with a water solution, as has been demonstrated for plant matter, to yield a microbe-containing filter eluate, such that the present combination of Raw Sample Genotyping (RSG) and microarray analysis would be capable of recovering and analyzing the DNA complement of those microbes.

While the foregoing written description of an embodiments enables one of ordinary skill to make and use what is considered presently to be the best mode thereof, those of ordinary skill will understand and appreciate the existence of variations, combinations, and equivalents of the specific embodiment, method, and examples herein. The present disclosure should therefore not be limited by the above described embodiments, methods, and examples, but by all embodiments and methods within the scope and spirit of the present disclosure.

What is claimed is:

1. A microarray system, consisting of: a substantially flat glass support with a front surface consisting of:
   (1) activated surface moieties selected from the group consisting of an epoxysilane group, an N-hydroxysuccinimide group and an activated carboxylic acid ester attached to the front surface; and
   (2) a plurality of oligodeoxythymidine linkers each covalently coupled at its 3'terminus via an amide bond to one of the activated surface moieties; wherein there are a greater number of activated surface moieties attached to the front surface of the substantially flat glass support as compared to the total number of covalently coupled oligodeoxythymidine linkers in the plurality thereof, and wherein the activated surface moieties that are not covalently coupled create a lattice width spacing between the covalently coupled plurality of oligodeoxythymidine linkers, each of said plurality of oligodeoxythymidine linkers consisting of:
   (a) 20 to 60 thymidine bases with its 5'terminus covalently linked to a fluorescent label; and
   (b) a plurality of nucleic acid probes selected from the group consisting of a plurality of pathogenic fungal nucleotide probes selected from the group consisting of SEQ ID NOS: 86-125, a plurality of Cannabis plant nucleotide probes selected from the group consisting of SEQ ID NOS: 126-128, and a combination thereof, wherein each of said pathogenic fungal nucleotide probes of SEQ ID NOS: 86-125 and each of said Cannabis plant nucleotide probes of SEQ ID NOS: 126-128 consists of a pathogenic fungal nucleotide sequence or a Cannabis plant nucleotide sequence sandwiched between three to seven consecutive thymidine nucleotides attached at both the 3'terminus and to the 5'terminus of each pathogenic fungal nucleotide sequence and each *Cannabis* plant nucleotide sequence;

wherein a thymidine nucleotide at the 3'terminus and a thymidine nucleotide at the 5'terminus of each of the plurality of nucleic acid probes is crosslinked to two adjacent oligodeoxythymidine linkers of the plurality of oligodeoxythymidine linkers attached to the substantially flat glass support; and wherein each of the plurality of nucleic acid probes crosslinked to the two adjacent oligodeoxythymidine linkers on the substantially flat glass support are separated by both a vertical space and the lattice width to form a 3-dimensional lattice on the substantially flat glass support.

2. The microarray system of claim 1, wherein the substantially flat glass support is borosilicate glass.

3. The microarray system of claim 1, wherein the fluorescent label is a cyanine fluorescent dye.

* * * * *

SEQUENCE LISTING

<160> NUMBER OF SEQ ID NOS: 132

<210> SEQ ID NO 1
<211> LENGTH: 23
<212> TYPE: DNA
<213> ORGANISM: Artificial Sequence
<220> FEATURE:
<223> OTHER INFORMATION: Forward primer for amplification of the 16S
      rDNA HV3 locus in all bacteria

<400> SEQUENCE: 1
tttcacaytg gractgagac acg                                            23

<210> SEQ ID NO 2
<211> LENGTH: 27
<212> TYPE: DNA
<213> ORGANISM: Artificial Sequence
<220> FEATURE:
<223> OTHER INFORMATION: Reverse primer for amplification of the 16S
      rDNA HV3 locus in all bacteria

<400> SEQUENCE: 2
tttgactacc agggtatcta atcctgt                                        27

<210> SEQ ID NO 3
<211> LENGTH: 28
<212> TYPE: DNA
<213> ORGANISM: Artificial Sequence
<220> FEATURE:
<223> OTHER INFORMATION: Forward primer for amplification of the Stx1
      locus in pathogenic Escherichia coli

<400> SEQUENCE: 3
tttataatct acggcttatt gttgaacg                                       28

<210> SEQ ID NO 4
<211> LENGTH: 29
<212> TYPE: DNA
<213> ORGANISM: Artificial Sequence
<220> FEATURE:
<223> OTHER INFORMATION: Reverse primer for amplification of the Stx1
      locus in pathogenic Escherichia coli

<400> SEQUENCE: 4
tttggtatag ctactgtcac cagacaatg                                      29

<210> SEQ ID NO 5
<211> LENGTH: 26
<212> TYPE: DNA
<213> ORGANISM: Artificial Sequence
<220> FEATURE:
<223> OTHER INFORMATION: Forward primer for amplification of the Stx2
      locus in pathogenic Escherichia coli

<400> SEQUENCE: 5
tttgatgcat ccagagcagt tctgcg                                         26

<210> SEQ ID NO 6
<211> LENGTH: 27
<212> TYPE: DNA
<213> ORGANISM: Artificial Sequence
<220> FEATURE:
<223> OTHER INFORMATION: Reverse primer for amplification of the Stx2
      locus in pathogenic Escherichia coli

<400> SEQUENCE: 6
tttgtgaggt ccacgtctcc cggcgtc                                        27

<210> SEQ ID NO 7
<211> LENGTH: 28
<212> TYPE: DNA
<213> ORGANISM: Artificial Sequence
<220> FEATURE:
<223> OTHER INFORMATION: Forward primer for amplification of the InvA
      locus in all Salmonella

<400> SEQUENCE: 7
tttattatcg ccacgttcgg gcaattcg                                          28

<210> SEQ ID NO 8
<211> LENGTH: 28
<212> TYPE: DNA
<213> ORGANISM: Artificial Sequence
<220> FEATURE:
<223> OTHER INFORMATION: Reverse primer for amplification of the InvA
      locus in all Salmonella

<400> SEQUENCE: 8
tttcttcatc gcaccgtcaa aggaaccg                                          28

<210> SEQ ID NO 9
<211> LENGTH: 26
<212> TYPE: DNA
<213> ORGANISM: Artificial Sequence
<220> FEATURE:
<223> OTHER INFORMATION: Forward primer for amplification of the tuf
      locus in all Escherichia coli

<400> SEQUENCE: 9
tttcagagtg ggaagcgaaa atcctg                                            26

<210> SEQ ID NO 10
<211> LENGTH: 26
<212> TYPE: DNA
<213> ORGANISM: Artificial Sequence
<220> FEATURE:
<223> OTHER INFORMATION: Reverse primer for amplification of the tuf
      locus in all Escherichia coli

<400> SEQUENCE: 10
tttacgccag tacaggtaga cttctg                                            26

<210> SEQ ID NO 11
<211> LENGTH: 30
<212> TYPE: DNA
<213> ORGANISM: Artificial Sequence
<220> FEATURE:
<223> OTHER INFORMATION: Forward primer for amplification of the 16S
      rDNA HV3 locus in Enterobacteriaceae

<400> SEQUENCE: 11
ttaccttcgg gcctcttgcc atcrgatgtg                                        30

<210> SEQ ID NO 12
<211> LENGTH: 33
<212> TYPE: DNA
<213> ORGANISM: Artificial Sequence
<220> FEATURE:
<223> OTHER INFORMATION: Reverse primer for amplification of the 16S
      rDNA HV3 locus in Enterobacteriaceae

<400> SEQUENCE: 12
ttggaattct accccctct acragactca agc                                     33

<210> SEQ ID NO 13
<211> LENGTH: 26
<212> TYPE: DNA
<213> ORGANISM: Artificial Sequence
<220> FEATURE:
<223> OTHER INFORMATION: Forward primer for amplification of the ITS2
      locus in all yeast and mold/fungi

<400> SEQUENCE: 13
tttactttya acaayggatc tcttgg                                              26

<210> SEQ ID NO 14
<211> LENGTH: 26
<212> TYPE: DNA
<213> ORGANISM: Artificial Sequence
<220> FEATURE:
<223> OTHER INFORMATION: Reverse primer for amplification of the ITS2
      locus in all yeast and mold/fungi

<400> SEQUENCE: 14
tttcttttcc tccgcttatt gatatg                                              26

<210> SEQ ID NO 15
<211> LENGTH: 28
<212> TYPE: DNA
<213> ORGANISM: Artificial Sequence
<220> FEATURE:
<223> OTHER INFORMATION: Forward primer for amplification of the ITS2
      locus in Aspergillus spp

<400> SEQUENCE: 15
tttaaaggca gcggcggcac cgcgtccg                                            28

<210> SEQ ID NO 16
<211> LENGTH: 27
<212> TYPE: DNA
<213> ORGANISM: Artificial Sequence
<220> FEATURE:
<223> OTHER INFORMATION: Reverse primer for amplification of the ITS2
      locus in Aspergillus spp

<400> SEQUENCE: 16
ttttcttttc ctccgcttat tgatatg                                             27

<210> SEQ ID NO 17
<211> LENGTH: 25
<212> TYPE: DNA
<213> ORGANISM: Artificial Sequence
<220> FEATURE:
<223> OTHER INFORMATION: Forward primer for amplification of the ITS1
      locus in Cannabis/plant

<400> SEQUENCE: 17
tttgcaacag cagaacgacc cgtga                                               25

<210> SEQ ID NO 18
<211> LENGTH: 25
<212> TYPE: DNA
<213> ORGANISM: Artificial Sequence
<220> FEATURE:
<223> OTHER INFORMATION: Reverse primer for amplification of the ITS1
      locus in Cannabis/plant

<400> SEQUENCE: 18
tttcgataaa cacgcatctc gattg                                               25

```
<210> SEQ ID NO 19
<211> LENGTH: 24
<212> TYPE: DNA
<213> ORGANISM: Artificial Sequence
<220> FEATURE:
<223> OTHER INFORMATION: Forward primer for amplification of the 16S
      rDNA HV3 locus in all bacteria

<400> SEQUENCE: 19
tttactgaga cacggyccar actc                                          24

<210> SEQ ID NO 20
<211> LENGTH: 24
<212> TYPE: DNA
<213> ORGANISM: Artificial Sequence
<220> FEATURE:
<223> OTHER INFORMATION: Reverse primer for amplification of the 16S
      rDNA HV3 Locus in all bacteria

<400> SEQUENCE: 20
tttgtattac cgcggctgct ggca                                          24

<210> SEQ ID NO 21
<211> LENGTH: 28
<212> TYPE: DNA
<213> ORGANISM: Artificial Sequence
<220> FEATURE:
<223> OTHER INFORMATION: Forward primer for amplification of the Stx1
      locus in pathogenic Escherichia coli

<400> SEQUENCE: 21
tttatgtgac aggatttgtt aacaggac                                      28

<210> SEQ ID NO 22
<211> LENGTH: 28
<212> TYPE: DNA
<213> ORGANISM: Artificial Sequence
<220> FEATURE:
<223> OTHER INFORMATION: Reverse primer for amplification of the Stx1
      locus in pathogenic Escherichia coli

<400> SEQUENCE: 22
tttctgtcac cagacaatgt aaccgctg                                      28

<210> SEQ ID NO 23
<211> LENGTH: 24
<212> TYPE: DNA
<213> ORGANISM: Artificial Sequence
<220> FEATURE:
<223> OTHER INFORMATION: Forward primer for amplification of the Stx2
      locus in pathogenic Escherichia coli

<400> SEQUENCE: 23 tttttgtcact gtcacagcag aag      24

<210> SEQ ID NO 24
<211> LENGTH: 25
<212> TYPE: DNA
<213> ORGANISM: Artificial Sequence
<220> FEATURE:
<223> OTHER INFORMATION: Reverse primer for amplification of the Stx2
      locus in pathogenic Escherichia coli

<400> SEQUENCE: 24
tttgcgtcat cgtatacaca ggagc                                         25

<210> SEQ ID NO 25
<211> LENGTH: 26
```

```
<212> TYPE: DNA
<213> ORGANISM: Artificial Sequence
<220> FEATURE:
<223> OTHER INFORMATION: Forward primer for amplification of the InvA
      locus in all Salmonella us

<400> SEQUENCE: 25
ttttatcgtt attaccaaag gttcag                                            26

<210> SEQ ID NO 26
<211> LENGTH: 28
<212> TYPE: DNA
<213> ORGANISM: Artificial Sequence
<220> FEATURE:
<223> OTHER INFORMATION: Reverse primer for amplification of the InvA
      locus in all Salmonella

<400> SEQUENCE: 26
tttcctttcc agtacgcttc gccgttcg                                          28

<210> SEQ ID NO 27
<211> LENGTH: 25
<212> TYPE: DNA
<213> ORGANISM: Artificial Sequence
<220> FEATURE:
<223> OTHER INFORMATION: Forward primer for amplification of the tuf
      locus in all Escherichia coli

<400> SEQUENCE: 27
tttgttgtta ccggtcgtgt agaac                                             25

<210> SEQ ID NO 28
<211> LENGTH: 28
<212> TYPE: DNA
<213> ORGANISM: Artificial Sequence
<220> FEATURE:
<223> OTHER INFORMATION: Reverse primer for amplification of the tuf
      locus in all Escherichia coli

<400> SEQUENCE: 28
tttcttctga gtctctttga taccaacg                                          28

<210> SEQ ID NO 29
<211> LENGTH: 30
<212> TYPE: DNA
<213> ORGANISM: Artificial Sequence
<220> FEATURE:
<223> OTHER INFORMATION: Forward primer for amplification of the 16S
      rDNA HV3 locus in Enterobacteriaceae

<400> SEQUENCE: 29
ttatattgca caatgggcgc aagcctgatg                                        30

<210> SEQ ID NO 30
<211> LENGTH: 25
<212> TYPE: DNA
<213> ORGANISM: Artificial Sequence
<220> FEATURE:
<223> OTHER INFORMATION: Reverse primer for amplification of the 16S
      rDNA HV3 locus in Enterobacteriaceae

<400> SEQUENCE: 30
ttttgtatta ccgcggctgc tggca                                             25

<210> SEQ ID NO 31
<211> LENGTH: 23
<212> TYPE: DNA
```

```
<213> ORGANISM: Artificial Sequence
<220> FEATURE:
<223> OTHER INFORMATION: Forward primer for amplification of the ITS2
      locus in all yeast and mold/fungi

<400> SEQUENCE: 31
tttgcatcga tgaagarcgy agc                                              23

<210> SEQ ID NO 32
<211> LENGTH: 22
<212> TYPE: DNA
<213> ORGANISM: Artificial Sequence
<220> FEATURE:
<223> OTHER INFORMATION: Reverse primer for amplification of the ITS2
      locus in all yeast and mold/fungi

<400> SEQUENCE: 32
tttcctccgc ttattgatat gc                                               22

<210> SEQ ID NO 33
<211> LENGTH: 26
<212> TYPE: DNA
<213> ORGANISM: Artificial Sequence
<220> FEATURE:
<223> OTHER INFORMATION: Forward primer for amplification of the ITS2
      locus in Aspergillus spp

<400> SEQUENCE: 33
tttcctcgag cgtatggggc tttgtc                                           26

<210> SEQ ID NO 34
<211> LENGTH: 24
<212> TYPE: DNA
<213> ORGANISM: Artificial Sequence
<220> FEATURE:
<223> OTHER INFORMATION: Reverse primer for amplification of the ITS2
      locus in Aspergillus spp

<400> SEQUENCE: 34
tttttcctcc gcttattgat atgc                                             24

<210> SEQ ID NO 35
<211> LENGTH: 27
<212> TYPE: DNA
<213> ORGANISM: Artificial Sequence
<220> FEATURE:
<223> OTHER INFORMATION: Forward primer for amplification of the ITS1
      locus in Cannabis/plant

<400> SEQUENCE: 35
tttcgtgaac acgttttaaa cagcttg                                          27

<210> SEQ ID NO 36
<211> LENGTH: 24
<212> TYPE: DNA
<213> ORGANISM: Artificial Sequence
<220> FEATURE:
<223> OTHER INFORMATION: Reverse primer for amplification of the ITS1
      locus in Cannabis/plant

<400> SEQUENCE: 36
tttccaccgc acgagccacg cgat                                             24

<210> SEQ ID NO 37
<211> LENGTH: 30
<212> TYPE: DNA
<213> ORGANISM: Artificial Sequence
```

<220> FEATURE:
<223> OTHER INFORMATION: Probe sequence for the 16S locus for total
      aerobic bacteria with high sensitivity

<400> SEQUENCE: 37
tttttttttc ctacgggagg cagttttttt                                        30

<210> SEQ ID NO 38
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with medium sensitivity

<400> SEQUENCE: 38
ttttttttcc ctacgggagg catttttttt                                        30

<210> SEQ ID NO 39
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with low sensitivity

<400> SEQUENCE: 39
tttattttcc ctacgggagg cttttatttt                                        30

<210> SEQ ID NO 40
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with low sensitivity

<400> SEQUENCE: 40
tttattctat tgacgttacc catttatttt                                        30

<210> SEQ ID NO 41
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with medium sensitivity

<400> SEQUENCE: 41 tttttttctat tgacgttacc cgtttttttt                                       30

<210> SEQ ID NO 42
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli/Shigella

<400> SEQUENCE: 42
ttttctaata cctttgctca ttgactcttt                                        30

<210> SEQ ID NO 43
<211> LENGTH: 30
<212> TYPE: DNA
<213> ORGANISM: Artificial Sequence
<220> FEATURE:

-continued

```
<223> OTHER INFORMATION: Probe sequence for the 16S locus in Escherichia
      coli/Shigella

<400> SEQUENCE: 43 tttttaagg gagtaaagtt aatattttt                                          30

<210> SEQ ID NO 44
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli/Shigella

<400> SEQUENCE: 44
ttttctcctt tgctcattga cgttattttt                                        30

<210> SEQ ID NO 45
<211> LENGTH: 30
<212> TYPE: DNA
<213> ORGANISM: Artificial Sequence
<220> FEATURE:
<223> OTHER INFORMATION: Probe sequence for the 16S locus in Bacillus
      spp. Group 1

<400> SEQUENCE: 45
tttttcagtt gaataagctg gcactctttt                                        30

<210> SEQ ID NO 46
<211> LENGTH: 30
<212> TYPE: DNA
<213> ORGANISM: Artificial Sequence
<220> FEATURE:
<223> OTHER INFORMATION: Probe sequence for the 16S locus in Bacillus
      spp. Group 2

<400> SEQUENCE: 46 tttttcaag taccgttcga atagttttt                                          30

<210> SEQ ID NO 47
<211> LENGTH: 36
<212> TYPE: DNA
<213> ORGANISM: Artificial Sequence
<220> FEATURE:
<223> OTHER INFORMATION: Probe sequence for the 16S locus in bile-
      tolerant gram negative bacteria with high sensitivity

<400> SEQUENCE: 47
tttttctatg cagtcatgct gtgtgtrtgt cttttt                                 36

<210> SEQ ID NO 48
<211> LENGTH: 34
<212> TYPE: DNA
<213> ORGANISM: Artificial Sequence
<220> FEATURE:
<223> OTHER INFORMATION: Probe sequence for the 16S locus in bile-
      tolerant gram negative bacteria with medium sensitivity

<400> SEQUENCE: 48
tttttctatg cagccatgct gtgtgtrttt tttt                                   34

<210> SEQ ID NO 49
<211> LENGTH: 34
<212> TYPE: DNA
<213> ORGANISM: Artificial Sequence
```

```
<220> FEATURE:
<223> OTHER INFORMATION: Probe sequence for the 16S locus in bile-
      tolerant gram negative bacteria with low sensitivity

<400> SEQUENCE: 49
tttttctatg cagtcatgct gcgtgtrttt tttt                                 34

<210> SEQ ID NO 50
<211> LENGTH: 30
<212> TYPE: DNA
<213> ORGANISM: Artificial Sequence
<220> FEATURE:
<223> OTHER INFORMATION: Probe sequence for the 16S locus in
      Campylobacter spp.

<400> SEQUENCE: 50 tttttttatga cacttttcgg agctcttttt                                     30

<210> SEQ ID NO 51
<211> LENGTH: 34
<212> TYPE: DNA
<213> ORGANISM: Artificial Sequence
<220> FEATURE:
<223> OTHER INFORMATION: Probe sequence for the 16S locus in
      Chromobacterium spp.

<400> SEQUENCE: 51
ttttattttc ccgctggtta ataccctta tttt                                  34

<210> SEQ ID NO 52
<211> LENGTH: 30
<212> TYPE: DNA
<213> ORGANISM: Artificial Sequence
<220> FEATURE:
<223> OTHER INFORMATION: Probe sequence for the 16S locus in Citrobacter
      spp. Gtoup 1

<400> SEQUENCE: 52
tttttccctt agccattgac gttatttttt                                      30

<210> SEQ ID NO 53
<211> LENGTH: 30
<212> TYPE: DNA
<213> ORGANISM: Artificial Sequence
<220> FEATURE:
<223> OTHER INFORMATION: Probe sequence for the 16S locus in Clostridium
      spp.

<400> SEQUENCE: 53
ttttctggam gataatgacg gtacagtttt                                      30

<210> SEQ ID NO 54
<211> LENGTH: 30
<212> TYPE: DNA
<213> ORGANISM: Artificial Sequence
<220> FEATURE:
<223> OTHER INFORMATION: Probe sequence for the 16S locus in
      Coliform/Enterobacteriaceae

<400> SEQUENCE: 54 tttttctat tgacgttacc cgcttttttt                                       30

<210> SEQ ID NO 55
<211> LENGTH: 30
<212> TYPE: DNA
<213> ORGANISM: Artificial Sequence
<220> FEATURE:
```

<223> OTHER INFORMATION: Probe sequence for the 16S locus in Aeromonas
      salmonicida/hydrophilia

<400> SEQUENCE: 55
tttttgccta atacgtrtca actgcttttt                                    30

<210> SEQ ID NO 56
<211> LENGTH: 30
<212> TYPE: DNA
<213> ORGANISM: Artificial Sequence
<220> FEATURE:
<223> OTHER INFORMATION: Probe sequence for the 16S locus in Aeromonas
      spp.

<400> SEQUENCE: 56
ttattttctg tgacgttact cgcttttatt                                    30

<210> SEQ ID NO 57
<211> LENGTH: 30
<212> TYPE: DNA
<213> ORGANISM: Artificial Sequence
<220> FEATURE:
<223> OTHER INFORMATION: Probe sequence for the 16S locus in
      Alkanindiges spp.

<400> SEQUENCE: 57
tttttaggct actgrtacta atatctttt                                     30

<210> SEQ ID NO 58
<211> LENGTH: 34
<212> TYPE: DNA
<213> ORGANISM: Artificial Sequence
<220> FEATURE:
<223> OTHER INFORMATION: Probe sequence for the 16S locus in Bacillus
      pumilus

<400> SEQUENCE: 58
tttatttaag tgcragagta actgctattt tatt                               34

<210> SEQ ID NO 59
<211> LENGTH: 34
<212> TYPE: DNA
<213> ORGANISM: Artificial Sequence
<220> FEATURE:
<223> OTHER INFORMATION: Probe sequence for bacterial etuf gene

<400> SEQUENCE: 59 tttttccat caaagttggt gaagaatctt tttt                                34

<210> SEQ ID NO 60
<211> LENGTH: 30
<212> TYPE: DNA
<213> ORGANISM: Artificial Sequence
<220> FEATURE:
<223> OTHER INFORMATION: Probe sequence for the 16S locus in Hafnia spp.

<400> SEQUENCE: 60 tttttctaa ccgcagtgat tgatctttt                                      30

<210> SEQ ID NO 61
<211> LENGTH: 34
<212> TYPE: DNA
<213> ORGANISM: Artificial Sequence
<220> FEATURE:
<223> OTHER INFORMATION: Probe sequence for bacterial InvA gene

```
<400> SEQUENCE: 61
tttttttatt gatgccgatt tgaaggcctt tttt                            34

<210> SEQ ID NO 62
<211> LENGTH: 30
<212> TYPE: DNA
<213> ORGANISM: Artificial Sequence
<220> FEATURE:
<223> OTHER INFORMATION: Probe sequence for the 16S locus in Klebsiella
      oxytoca

<400> SEQUENCE: 62 tttttctaa ccttattcat tgatctttt                                   30

<210> SEQ ID NO 63
<211> LENGTH: 30
<212> TYPE: DNA
<213> ORGANISM: Artificial Sequence
<220> FEATURE:
<223> OTHER INFORMATION: Probe sequence for the 16S locus in Klebsiella
      pneumoniae

<400> SEQUENCE: 63 tttttctaa ccttggcgat tgatctttt                                   30

<210> SEQ ID NO 64
<211> LENGTH: 34
<212> TYPE: DNA
<213> ORGANISM: Artificial Sequence
<220> FEATURE:
<223> OTHER INFORMATION: Probe sequence for the 16S locus in Legionella
      spp.

<400> SEQUENCE: 64
tttattctga taggttaaga gctgatcttt attt                            34

<210> SEQ ID NO 65
<211> LENGTH: 30
<212> TYPE: DNA
<213> ORGANISM: Artificial Sequence
<220> FEATURE:
<223> OTHER INFORMATION: Probe sequence for the 16S locus in Listeria
      spp.

<400> SEQUENCE: 65
ttttctaagt actgttgtta gagaatttt                                  30

<210> SEQ ID NO 66
<211> LENGTH: 30
<212> TYPE: DNA
<213> ORGANISM: Artificial Sequence
<220> FEATURE:
<223> OTHER INFORMATION: Probe sequence for the 16S locus in Panteoa
      agglomerans

<400> SEQUENCE: 66 tttttaacc ctgtcgattg acgccttttt                                  30

<210> SEQ ID NO 67
<211> LENGTH: 30
<212> TYPE: DNA
<213> ORGANISM: Artificial Sequence
<220> FEATURE:
<223> OTHER INFORMATION: Probe sequence for the 16S locus in Panteoa
      stewartii
```

<400> SEQUENCE: 67 tttttaacc tcatcaattg acgccttttt					30

<210> SEQ ID NO 68
<211> LENGTH: 30
<212> TYPE: DNA
<213> ORGANISM: Artificial Sequence
<220> FEATURE:
<223> OTHER INFORMATION: Probe sequence for the 16S locus in Pseudomonas
      aeruginosa

<400> SEQUENCE: 68
tttttgcagt aagttaatac cttgtctttt					30

<210> SEQ ID NO 69
<211> LENGTH: 30
<212> TYPE: DNA
<213> ORGANISM: Artificial Sequence
<220> FEATURE:
<223> OTHER INFORMATION: Probe sequence for the 16S locus in Pseudomonas
      cannabina

<400> SEQUENCE: 69 ttttttacg tatctgtttt gactctttt					30

<210> SEQ ID NO 70
<211> LENGTH: 30
<212> TYPE: DNA
<213> ORGANISM: Artificial Sequence
<220> FEATURE:
<223> OTHER INFORMATION: Probe sequence for the 16S locus in Pseudomonas
      spp.

<400> SEQUENCE: 70
tttttgttac cracagaata agcatttt     30

<210> SEQ ID NO 71
<211> LENGTH: 30
<212> TYPE: DNA
<213> ORGANISM: Artificial Sequence
<220> FEATURE:
<223> OTHER INFORMATION: Probe sequence for the 16S locus in Pseudomonas
      spp.

<400> SEQUENCE: 71
ttttttaagc actttaagtt gggatttttt					30

<210> SEQ ID NO 72
<211> LENGTH: 34
<212> TYPE: DNA
<213> ORGANISM: Artificial Sequence
<220> FEATURE:
<223> OTHER INFORMATION: Probe sequence for the 16S locus in Pseudomonas
      spp.

<400> SEQUENCE: 72
tttattttaa gcactttaag ttgggatttt attt					34

<210> SEQ ID NO 73
<211> LENGTH: 30
<212> TYPE: DNA
<213> ORGANISM: Artificial Sequence
<220> FEATURE:
<223> OTHER INFORMATION: Probe sequence for the 16S locus in Salmonella
      bongori

<400> SEQUENCE: 73
tttttttaat aaccttgttg attgttttttt                30

<210> SEQ ID NO 74
<211> LENGTH: 30
<212> TYPE: DNA
<213> ORGANISM: Artificial Sequence
<220> FEATURE:
<223> OTHER INFORMATION: Probe sequence for the 16S locus in Salmonella
      enterica

<400> SEQUENCE: 74
tttttttgtt gtggttaata accgattttt                30

<210> SEQ ID NO 75
<211> LENGTH: 30
<212> TYPE: DNA
<213> ORGANISM: Artificial Sequence
<220> FEATURE:
<223> OTHER INFORMATION: Probe sequence for the 16S locus in Salmonella
      enterica

<400> SEQUENCE: 75
tttttttaac cgcagcaatt gactcttttt                30

<210> SEQ ID NO 76
<211> LENGTH: 30
<212> TYPE: DNA
<213> ORGANISM: Artificial Sequence
<220> FEATURE:
<223> OTHER INFORMATION: Probe sequence for the 16S locus in Salmonella
      enterica

<400> SEQUENCE: 76 tttttctgt taataaccgc agcttttttt                30

<210> SEQ ID NO 77
<211> LENGTH: 34
<212> TYPE: DNA
<213> ORGANISM: Artificial Sequence
<220> FEATURE:
<223> OTHER INFORMATION: Probe sequence for the 16S locus in Serratia
      spp.

<400> SEQUENCE: 77
tttattctgt gaacttaata cgttcatttt tatt                34

<210> SEQ ID NO 78
<211> LENGTH: 34
<212> TYPE: DNA
<213> ORGANISM: Artificial Sequence
<220> FEATURE:
<223> OTHER INFORMATION: Probe sequence for the 16S locus in
      Staphylococcus aureus

<400> SEQUENCE: 78
tttattttca tatgtgtaag taactgtttt attt                34

<210> SEQ ID NO 79
<211> LENGTH: 30
<212> TYPE: DNA
<213> ORGANISM: Artificial Sequence
<220> FEATURE:
<223> OTHER INFORMATION: Probe sequence for the 16S locus in
      Staphylococcus aureus

```
<400> SEQUENCE: 79 tttttcata tgtgtaagta actgttttt                                      30

<210> SEQ ID NO 80
<211> LENGTH: 34
<212> TYPE: DNA
<213> ORGANISM: Artificial Sequence
<220> FEATURE:
<223> OTHER INFORMATION: Probe sequence for the 16S locus in
      Streptomyces spp.

<400> SEQUENCE: 80
ttttatttta agaagcgaga gtgacttta tttt                                34

<210> SEQ ID NO 81
<211> LENGTH: 30
<212> TYPE: DNA
<213> ORGANISM: Artificial Sequence
<220> FEATURE:
<223> OTHER INFORMATION: Probe sequence for bacterial stx1 gene

<400> SEQUENCE: 81
tttttctttt ccaggtacaa cagcttttt                                     30

<210> SEQ ID NO 82
<211> LENGTH: 30
<212> TYPE: DNA
<213> ORGANISM: Artificial Sequence
<220> FEATURE:
<223> OTHER INFORMATION: Probe sequence for bacterial stx2 gene

<400> SEQUENCE: 82 tttttgcac tgtctgaaac tgccttttt                                      30

<210> SEQ ID NO 83
<211> LENGTH: 30
<212> TYPE: DNA
<213> ORGANISM: Artificial Sequence
<220> FEATURE:
<223> OTHER INFORMATION: Probe sequence for the 16S locus in Vibrio spp.

<400> SEQUENCE: 83 tttttgaag gtggttaagc taattttttt                                     30

<210> SEQ ID NO 84
<211> LENGTH: 30
<212> TYPE: DNA
<213> ORGANISM: Artificial Sequence
<220> FEATURE:
<223> OTHER INFORMATION: Probe sequence for the 16S locus in Xanthamonas
      spp.

<400> SEQUENCE: 84 tttttgtta atacccgatt gttctttttt                                     30

<210> SEQ ID NO 85
<211> LENGTH: 30
<212> TYPE: DNA
<213> ORGANISM: Artificial Sequence
<220> FEATURE:
<223> OTHER INFORMATION: Probe sequence for the 16S locus in Ysernia
      pestis

<400> SEQUENCE: 85
tttttttgag tttaatacgc tcaacttttt                                    30
```

```
<210> SEQ ID NO 86
<211> LENGTH: 38
<212> TYPE: DNA
<213> ORGANISM: Artificial Sequence
<220> FEATURE:
<223> OTHER INFORMATION: Probe sequence for the ITS2 locus in total
      yeast and mold with high sensitivity

<400> SEQUENCE: 86 tttttttga atcatcgart ctttgaacgc attttttt                              38

<210> SEQ ID NO 87
<211> LENGTH: 31
<212> TYPE: DNA
<213> ORGANISM: Artificial Sequence
<220> FEATURE:
<223> OTHER INFORMATION: Probe sequence for the ITS2 locus in total
      yeast and mold with low sensitivity

<400> SEQUENCE: 87 tttttttga atcatcgart ctccttttt t                                      31

<210> SEQ ID NO 88
<211> LENGTH: 36
<212> TYPE: DNA
<213> ORGANISM: Artificial Sequence
<220> FEATURE:
<223> OTHER INFORMATION: Probe sequence for the ITS2 locus in total
      yeast and mold with medium sensitivity

<400> SEQUENCE: 88 tttttttga atcatcgart ctttgaacgt tttttt                                36

<210> SEQ ID NO 89
<211> LENGTH: 34
<212> TYPE: DNA
<213> ORGANISM: Artificial Sequence
<220> FEATURE:
<223> OTHER INFORMATION: Probe sequence for the ITS2 locus in Alternaria
      spp.

<400> SEQUENCE: 89 tttttcaaa ggtctagcat ccattaagtt tttt                                  34

<210> SEQ ID NO 90
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus flavus

<400> SEQUENCE: 90 tttttcgca aatcaatctt tttccagtct tttt                                  34

<210> SEQ ID NO 91
<211> LENGTH: 40
<212> TYPE: DNA
<213> ORGANISM: Artificial Sequence
<220> FEATURE:
<223> OTHER INFORMATION: Probe sequence for the ITS2 locus in
      Aspergillus flavus

<400> SEQUENCE: 91
tttttttctt gccgaacgca aatcaatctt ttttttttt                            40
```

```
<210> SEQ ID NO 92
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus fumigatus

<400> SEQUENCE: 92
tttcttttcg acacccaact ttatttcctt attt                                34

<210> SEQ ID NO 93
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus fumigatus

<400> SEQUENCE: 93
tttttttgcc agccgacacc cattcttttt                                     30

<210> SEQ ID NO 94
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus nidulans

<400> SEQUENCE: 94 tttttttggcg tctccaacct taccctttt                                     30

<210> SEQ ID NO 95
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus niger

<400> SEQUENCE: 95 tttttttcgac gttttccaac catttctttt                                    30

<210> SEQ ID NO 96
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus niger

<400> SEQUENCE: 96
ttttttttcg acgttttcca accatttctt tttt                                34

<210> SEQ ID NO 97
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus niger

<400> SEQUENCE: 97
tttttttcgc cgacgttttc caatttttt                                      30

<210> SEQ ID NO 98
```

```
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus terreus

<400> SEQUENCE: 98
tttttcgacg catttatttg caacccttt                                    30

<210> SEQ ID NO 99
<211> LENGTH: 34
<212> TYPE: DNA
<213> ORGANISM: Artificial Sequence
<220> FEATURE:
<223> OTHER INFORMATION: Probe sequence for the ITS2 locus in Blumeria
      spp.

<400> SEQUENCE: 99
tttatttgcc aaaamtcctt aattgctctt tttt                              34

<210> SEQ ID NO 100
<211> LENGTH: 40
<212> TYPE: DNA
<213> ORGANISM: Artificial Sequence
<220> FEATURE:
<223> OTHER INFORMATION: Probe sequence for the ITS2 locus in Botrytis
      spp.

<400> SEQUENCE: 100 ttttttcat ctctcgttac aggttctcgg ttctttttt                          40

<210> SEQ ID NO 101
<211> LENGTH: 34
<212> TYPE: DNA
<213> ORGANISM: Artificial Sequence
<220> FEATURE:
<223> OTHER INFORMATION: Probe sequence for the ITS2 locus in Candida
      albicans

<400> SEQUENCE: 101
tttttttttg aaagacggta gtggtaagtt tttt                              34

<210> SEQ ID NO 102
<211> LENGTH: 34
<212> TYPE: DNA
<213> ORGANISM: Artificial Sequence
<220> FEATURE:
<223> OTHER INFORMATION: Probe sequence for the ITS2 locus in Candida
      spp. Group 1

<400> SEQUENCE: 102 ttttttgtt tggtgttgag cratacgtat tttt                               34

<210> SEQ ID NO 103
<211> LENGTH: 35
<212> TYPE: DNA
<213> ORGANISM: Artificial Sequence
<220> FEATURE:
<223> OTHER INFORMATION: Probe sequence for the ITS2 locus in Candida
      spp. Group 2

<400> SEQUENCE: 103
ttttactgtt tggtaatgag tgatactctc atttt                             35

<210> SEQ ID NO 104
<211> LENGTH: 34
```

```
<212> TYPE: DNA
<213> ORGANISM: Artificial Sequence
<220> FEATURE:
<223> OTHER INFORMATION: Probe sequence for the ITS2 locus in Chaetomium
      spp.

<400> SEQUENCE: 104
tttcttttgg ttccggccgt taaaccattt tttt                                34

<210> SEQ ID NO 105
<211> LENGTH: 34
<212> TYPE: DNA
<213> ORGANISM: Artificial Sequence
<220> FEATURE:
<223> OTHER INFORMATION: Probe sequence for the ITS2 locus in
      Cladosporium spp.

<400> SEQUENCE: 105 tttttttgt ggaaactatt cgctaaagtt tttt                                 34

<210> SEQ ID NO 106
<211> LENGTH: 34
<212> TYPE: DNA
<213> ORGANISM: Artificial Sequence
<220> FEATURE:
<223> OTHER INFORMATION: Probe sequence for the ITS2 locus in Erysiphe
      spp.

<400> SEQUENCE: 106
tttcttttta cgattctcgc gacagagttt tttt                                34

<210> SEQ ID NO 107
<211> LENGTH: 34
<212> TYPE: DNA
<213> ORGANISM: Artificial Sequence
<220> FEATURE:
<223> OTHER INFORMATION: Probe sequence for the ITS2 locus in Fusarum
      oxysporum

<400> SEQUENCE: 107 ttttttctc gttactggta atcgtcgttt tttt                                 34

<210> SEQ ID NO 108
<211> LENGTH: 34
<212> TYPE: DNA
<213> ORGANISM: Artificial Sequence
<220> FEATURE:
<223> OTHER INFORMATION: Probe sequence for the ITS2 locus in Fusarium
      spp.

<400> SEQUENCE: 108
ttttttttaa cacctcgcra ctggagattt tttt                                34

<210> SEQ ID NO 109
<211> LENGTH: 34
<212> TYPE: DNA
<213> ORGANISM: Artificial Sequence
<220> FEATURE:
<223> OTHER INFORMATION: Probe sequence for the ITS2 locus in
      Golovinomyces spp.

<400> SEQUENCE: 109 tttttccgc ttgccaatca atccatctct tttt                                 34

<210> SEQ ID NO 110
<211> LENGTH: 34
<212> TYPE: DNA
```

```
<213> ORGANISM: Artificial Sequence
<220> FEATURE:
<223> OTHER INFORMATION: Probe sequence for the ITS2 locus in
      Histoplasma capsulatum

<400> SEQUENCE: 110 tttattttg tcgagttccg gtgccctttt attt                              34

<210> SEQ ID NO 111
<211> LENGTH: 34
<212> TYPE: DNA
<213> ORGANISM: Artificial Sequence
<220> FEATURE:
<223> OTHER INFORMATION: Probe sequence for the ITS2 locus in Isaria
      spp.

<400> SEQUENCE: 111 tttattttc cgcggcgacc tctgctcttt attt                              34

<210> SEQ ID NO 112
<211> LENGTH: 34
<212> TYPE: DNA
<213> ORGANISM: Artificial Sequence
<220> FEATURE:
<223> OTHER INFORMATION: Probe sequence for the ITS2 locus in
      Monocillium spp.

<400> SEQUENCE: 112
tttcttttga gcgacgacgg gcccaatttt cttt                             34

<210> SEQ ID NO 113
<211> LENGTH: 30
<212> TYPE: DNA
<213> ORGANISM: Artificial Sequence
<220> FEATURE:
<223> OTHER INFORMATION: Probe sequence for the ITS2 locus in Mucor spp.

<400> SEQUENCE: 113
ttttctccaw tgagyacgcc tgtttctttt                                  30

<210> SEQ ID NO 114
<211> LENGTH: 34
<212> TYPE: DNA
<213> ORGANISM: Artificial Sequence
<220> FEATURE:
<223> OTHER INFORMATION: Probe sequence for the ITS2 locus in
      Myrothecium spp.

<400> SEQUENCE: 114
tttattttcg gtggccatgc cgttaaattt tatt                             34

<210> SEQ ID NO 115
<211> LENGTH: 34
<212> TYPE: DNA
<213> ORGANISM: Artificial Sequence
<220> FEATURE:
<223> OTHER INFORMATION: Probe sequence for the ITS2 locus in
      Oidiodendron spp.

<400> SEQUENCE: 115
tttttttgcg tagtacatct ctcgctcatt tttt                             34

<210> SEQ ID NO 116
<211> LENGTH: 34
<212> TYPE: DNA
<213> ORGANISM: Artificial Sequence
<220> FEATURE:
```

```
<223> OTHER INFORMATION: Probe sequence for the ITS2 locus in
      Penicillium oxalicum

<400> SEQUENCE: 116 tttttacac catcaatctt aaccaggcct tttt                                34

<210> SEQ ID NO 117
<211> LENGTH: 34
<212> TYPE: DNA
<213> ORGANISM: Artificial Sequence
<220> FEATURE:
<223> OTHER INFORMATION: Probe sequence for the ITS2 locus in
      Penicillium paxilli

<400> SEQUENCE: 117
tttttccccc tcaatcttta accaggcctt tttt                               34

<210> SEQ ID NO 118
<211> LENGTH: 34
<212> TYPE: DNA
<213> ORGANISM: Artificial Sequence
<220> FEATURE:
<223> OTHER INFORMATION: Probe sequence for the ITS2 locus in
      Penicillium spp.

<400> SEQUENCE: 118 tttttcaac ccaaattttt atccaggcct tttt                                34

<210> SEQ ID NO 119
<211> LENGTH: 34
<212> TYPE: DNA
<213> ORGANISM: Artificial Sequence
<220> FEATURE:
<223> OTHER INFORMATION: Probe sequence for the ITS2 locus in
      Phoma/Epicoccum ssp.

<400> SEQUENCE: 119 ttttttgca gtacatctcg cgctttgatt tttt                                34

<210> SEQ ID NO 120
<211> LENGTH: 34
<212> TYPE: DNA
<213> ORGANISM: Artificial Sequence
<220> FEATURE:
<223> OTHER INFORMATION: Probe sequence for the ITS2 locus in
      Podosphaera spp.

<400> SEQUENCE: 120 tttttgacc tgccaaaacc cacataccat tttt                                34

<210> SEQ ID NO 121
<211> LENGTH: 34
<212> TYPE: DNA
<213> ORGANISM: Artificial Sequence
<220> FEATURE:
<223> OTHER INFORMATION: Probe sequence for the ITS2 locus in
      Podosphaera spp.

<400> SEQUENCE: 121 tttttttag tcaygtatct cgcgacagtt tttt                                34

<210> SEQ ID NO 122
<211> LENGTH: 34
<212> TYPE: DNA
<213> ORGANISM: Artificial Sequence
<220> FEATURE:
```

<223> OTHER INFORMATION: Probe sequence for the ITS2 locus in Phythium
oligandrum

<400> SEQUENCE: 122
ttttatttaa aggagacaac accaattttt attt                              34

<210> SEQ ID NO 123
<211> LENGTH: 34
<212> TYPE: DNA
<213> ORGANISM: Artificial Sequence
<220> FEATURE:
<223> OTHER INFORMATION: Probe sequence for the ITS2 locus in
      Rhodoturula spp.

<400> SEQUENCE: 123 tttttctcg ttcgtaatgc attagcactt tttt                               34

<210> SEQ ID NO 124
<211> LENGTH: 34
<212> TYPE: DNA
<213> ORGANISM: Artificial Sequence
<220> FEATURE:
<223> OTHER INFORMATION: Probe sequence for the ITS2 locus in
      Stachybotrys spp.

<400> SEQUENCE: 124
tttcttctgc atcggagctc agcgcgtttt attt                              34

<210> SEQ ID NO 125
<211> LENGTH: 34
<212> TYPE: DNA
<213> ORGANISM: Artificial Sequence
<220> FEATURE:
<223> OTHER INFORMATION: Probe sequence for the ITS2 locus in
      Trichoderma spp.

<400> SEQUENCE: 125
tttttcctcc tgcgcagtag tttgcacatc tttt                              34

<210> SEQ ID NO 126
<211> LENGTH: 34
<212> TYPE: DNA
<213> ORGANISM: Artificial Sequence
<220> FEATURE:
<223> OTHER INFORMATION: Probe sequence for ITS1 locus in Cannabis
      species

<400> SEQUENCE: 126 tttttaatc tgcgccaagg aacaatattt tttt                               34

<210> SEQ ID NO 127
<211> LENGTH: 34
<212> TYPE: DNA
<213> ORGANISM: Artificial Sequence
<220> FEATURE:
<223> OTHER INFORMATION: Probe sequence for ITS1 locus in Cannabis
      species

<400> SEQUENCE: 127 ttttgcaat ctgcgccaag gaacaatatt tttt                               34

<210> SEQ ID NO 128
<211> LENGTH: 34
<212> TYPE: DNA
<213> ORGANISM: Artificial Sequence
<220> FEATURE:

```
<223> OTHER INFORMATION: Probe sequence for ITS1 locus in Cannabis
      species

<400> SEQUENCE: 128
tttatttctt gcgccaagga acaatatttt attt                              34

<210> SEQ ID NO 129
<211> LENGTH: 32
<212> TYPE: DNA
<213> ORGANISM: Artificial Sequence
<220> FEATURE:
<223> OTHER INFORMATION: Probe sequence for image calibration with high
      sensitivity

<400> SEQUENCE: 129
ttttctatgt atcgatgttg agaaattttt tt                                32

<210> SEQ ID NO 130
<211> LENGTH: 32
<212> TYPE: DNA
<213> ORGANISM: Artificial Sequence
<220> FEATURE:
<223> OTHER INFORMATION: Probe sequence for image calibration with low
      sensitivity

<400> SEQUENCE: 130
ttttctagat acttgtgtaa gtgaattttt tt                                32

<210> SEQ ID NO 131
<211> LENGTH: 32
<212> TYPE: DNA
<213> ORGANISM: Artificial Sequence
<220> FEATURE:
<223> OTHER INFORMATION: Probe sequence for image calibration with
      medium sensitivity

<400> SEQUENCE: 131
ttttctaagt catgttgttg aagaattttt tt                                32

<210> SEQ ID NO 132
<211> LENGTH: 34
<212> TYPE: DNA
<213> ORGANISM: Artificial Sequence
<220> FEATURE:
<223> OTHER INFORMATION: Probe sequence for negative control

<400> SEQUENCE: 132 tttttttctac tacctatgct gattcactct tttt                             34
```